US011518723B2

(12) United States Patent
Yang et al.

(10) Patent No.: US 11,518,723 B2
(45) Date of Patent: Dec. 6, 2022

(54) FUSED RING COMPOUND, HIGH POLYMER, MIXTURE, COMPOSITION AND ORGANIC ELECTRONIC COMPONENT

(71) Applicant: GUANGZHOU CHINARAY OPTOELECTRONIC MATERIALS LTD., Guangdong (CN)

(72) Inventors: Xi Yang, Guangdong (CN); Junyou Pan, Guangdong (CN)

(73) Assignee: GUANGZHOU CHINARAY OPTOELECTRONIC MATERIALS LTD., Guangdong (CN)

( * ) Notice: Subject to any disclaimer, the term of this patent is extended or adjusted under 35 U.S.C. 154(b) by 739 days.

(21) Appl. No.: 16/463,439

(22) PCT Filed: Nov. 23, 2017

(86) PCT No.: PCT/CN2017/112706
§ 371 (c)(1),
(2) Date: May 23, 2019

(87) PCT Pub. No.: WO2018/095385
PCT Pub. Date: May 31, 2018

(65) Prior Publication Data
US 2021/0114954 A1 Apr. 22, 2021

(30) Foreign Application Priority Data
Nov. 23, 2016 (CN) .......................... 201611051633.0

(51) Int. Cl.
C07C 15/62 (2006.01)
C09K 11/06 (2006.01)
(Continued)

(52) U.S. Cl.
CPC .............. C07C 15/62 (2013.01); C09K 11/06 (2013.01); H01L 51/0054 (2013.01);
(Continued)

(58) Field of Classification Search
None
See application file for complete search history.

(56) References Cited

U.S. PATENT DOCUMENTS 3,567,450 A 3/1971 Brantly et al.
3,615,404 A 10/1971 Price et al.
(Continued)

FOREIGN PATENT DOCUMENTS

CN 1583691 A 2/2005
CN 1842510 A1 10/2006
(Continued)

OTHER PUBLICATIONS

International Search Report received in PCT/CN2017/112706, dated Feb. 2, 2018.
(Continued)

Primary Examiner — Michael Lebentritt
(74) Attorney, Agent, or Firm — PV IP PC; Wei Te Chung; Ude Lu

(57) ABSTRACT

A fused ring compound and applications thereof in organic electronic components, particularly in organic electroluminescent diodes; an organic electronic component comprising the fused ring compound, and applications thereof in organic electroluminescent diodes and in display and lighting technologies; and a formulation comprising the fused ring compound, and applications thereof in the preparation of organic electronic components. By optimizing the component structure, good component performance can be achieved, and especially, a high-performance OLED component can be implemented, which provide good material and preparation technology choices for full-color display and lighting applications.

18 Claims, 1 Drawing Sheet

(51) Int. Cl.
 H01L 51/00 (2006.01)
 H01L 51/50 (2006.01)
(52) U.S. Cl.
 CPC ...... H01L 51/0069 (2013.01); H01L 51/0072 (2013.01); H01L 51/0073 (2013.01); H01L 51/0074 (2013.01); *C09K 2211/1011* (2013.01); *C09K 2211/1033* (2013.01); *C09K 2211/1037* (2013.01); *C09K 2211/1044* (2013.01); *C09K 2211/1059* (2013.01); *H01L 51/5056* (2013.01)

(56) References Cited

U.S. PATENT DOCUMENTS

| | | | |
|---|---|---|---|
| 4,720,432 | A | 1/1988 | VanSlyke et al. |
| 4,769,292 | A | 9/1988 | Tang et al. |
| 5,061,569 | A | 10/1991 | VanSlyke et al. |
| 5,121,029 | A | 6/1992 | Hosokawa et al. |
| 5,130,603 | A | 7/1992 | Tokailin et al. |
| 6,020,078 | A | 2/2000 | Chen et al. |
| 6,251,531 | B1 | 6/2001 | Enokida et al. |
| 7,098,297 | B2* | 8/2006 | Pei ............ C08G 73/0627 428/917 |
| 7,233,019 | B2 | 6/2007 | Lonkin et al. |
| 7,250,532 | B2 | 7/2007 | Iwakuma et al. |
| 9,017,825 | B2 | 4/2015 | Heil et al. |
| 9,219,234 | B2 | 12/2015 | Kubota et al. |
| 9,373,792 | B2 | 6/2016 | Kawamura et al. |
| 9,660,198 | B2 | 5/2017 | Nakagawa et al. |
| 9,660,199 | B2 | 5/2017 | Shizu et al. |
| 9,882,144 | B2* | 1/2018 | Kawamura ........ C07D 417/14 |
| 10,454,038 | B2 | 10/2019 | Nakagawa et al. |
| 11,302,872 | B2* | 4/2022 | Zeng ............... H01L 51/0072 |
| 2006/0210830 | A1 | 9/2006 | Funahashi et al. |
| 2006/0222886 | A1 | 10/2006 | Kwong et al. |
| 2007/0092753 | A1 | 4/2007 | Begley et al. |
| 2007/0252517 | A1 | 11/2007 | Owczarczyk et al. |
| 2008/0113101 | A1 | 5/2008 | Inoue et al. |
| 2009/0110956 | A1* | 4/2009 | Begley ............... H01L 51/0054 428/690 |
| 2009/0134784 | A1 | 5/2009 | Lin et al. |
| 2011/0248250 | A1* | 10/2011 | D'Andrade ........... C07C 15/30 257/40 |
| 2012/0217869 | A1 | 8/2012 | Adachi et al. |
| 2012/0223295 | A1* | 9/2012 | Inoue .................. C09K 11/06 548/440 |
| 2014/0183463 | A1 | 7/2014 | Lee et al. |
| 2015/0141642 | A1 | 5/2015 | Adachi et al. |
| 2015/0287928 | A1 | 10/2015 | Kubota et al. |
| 2017/0084843 | A1* | 3/2017 | Yun .................... H01L 51/0059 |
| 2017/0365801 | A1* | 12/2017 | Margulies ........... H01L 51/0085 |
| 2019/0248804 | A1* | 8/2019 | Wolleb ............... H01L 51/0054 |
| 2019/0330152 | A1* | 10/2019 | Yang .................. C07D 403/10 |
| 2020/0223857 | A1* | 7/2020 | He .................... H01L 51/0072 |
| 2021/0043843 | A1* | 2/2021 | Kim ................... C07D 401/14 |
| 2021/0280795 | A1* | 9/2021 | Cui ................... H01L 51/0072 |

FOREIGN PATENT DOCUMENTS

| | | |
|---|---|---|
| CN | 1914293 B | 12/2010 |
| CN | 103483332 A | 1/2014 |
| CN | 102448945 B | 1/2016 |
| DE | 102005058557 A1 | 6/2007 |
| EP | 1957606 A1 | 8/2008 |
| JP | 1996053397 A | 3/1997 |
| JP | 2913116 B2 | 6/1999 |
| KR | 1020060006760 A | 1/2006 |
| TW | 201309696 A | 3/2013 |
| TW | 201309778 A | 3/2013 |
| TW | 201343874 A | 11/2013 |
| TW | 201350558 A | 12/2013 |
| WO | 2001021729 A1 | 3/2001 |
| WO | 2004013073 A1 | 2/2004 |
| WO | 2004016575 A1 | 2/2004 |
| WO | 2004018587 A1 | 3/2004 |
| WO | 2006000388 A1 | 1/2006 |
| WO | 2006000389 A1 | 1/2006 |
| WO | 2006058737 A1 | 6/2006 |
| WO | 2006122630 A1 | 11/2006 |
| WO | 2007065549 A1 | 6/2007 |
| WO | 2007115610 A1 | 10/2007 |
| WO | 2007140847 A1 | 12/2007 |
| WO | 2008006449 A1 | 1/2008 |
| WO | 2010067893 A1 | 6/2010 |
| WO | 2010135519 A1 | 11/2010 |
| WO | 2011110277 A1 | 9/2011 |
| WO | 2013133359 A1 | 9/2013 |
| WO | 2013154064 A1 | 10/2013 |

OTHER PUBLICATIONS

Chemical Abstracts Service, Columbus, Hoio, US Database Regisstry online, Database Accession No. 1633048-16-4, 2014.
Feng, et al., 'Influence of Substituent Position of Thermal Properties, Photoluminescence and Morphology of Pyrene-Fluorene Derivatives', *Journal of Molecule Structure*, 1086 (2015), pp. 216-222.
Tang, et al., Alternating Pyrene-Fluorene Linear Copolymers: Influence of Non-Conjugated and Conjugated Pyrene on Thermal and Optoelectronic Properties, *Synthetic Metals*, 174 (2013), pp. 33-41.
Endo et al., "Thermally Activated Delayed Fluorescence from $Sn^{4+}$—Porphyrin Complexes and Their Application to Organic Light-Emitting Diodes — A Novel Mechanism for Electroluminescence", Adv. Mater., vol. 21, (2009), pp. 4802-4806.
Li et al., Highly Efficient Organic Light-Emitting Diode Based on a Hidden Thermally Activated Delayed Fluorescence Channel in a Heptazine Derivative, Adv. Mater., vol. 25, (2013), pp. 1-5.
Dias et al., "Triplet Harvesting with 100% Efficiency by Way of Thermally Activated Delayed Fluorescence in Charge Transfer OLEO Emitters", Adv. Mater., vol. 25, (2013), pp. 3707-3714.
Mehes et al., "Enhanced Electroluminescence Efficiency in a Spiro-Acridine Derivative through Thermally Activated Delayed Fluorescence", Angew. Chem. Int. Ed., vol. 51, (2012), pp. 11311-11315.
Endo et al., "Efficient up-conversion of triplet excitons into a singlet state and its application for organic light emitting diodes", Appl. Phys. Lett., vol. 98, (2011), pp. 083302-1-083302-3.
Lee et al., "High-efficiency organic light-emitting diodes utilizing thermally activated delayed fluorescence from triazine-based donor-acceptor hybrid molecules", Appl. Phys. Lett., vol. 101, (2012), pp. 093306-1-093306-4.
Nakagawa et al., "Electroluminescence based on thermally activated delayed fluorescence generated by a spirobifluorene donor-acceptor structure" Chem. Commun., vol. 48, (2012), pp. 9580-9582.
Tanaka et al., "Efficient green thermally activated delayed fluorescence (TADF) from a phenoxazinetriphenyltriazine (PXZ-TRZ) derivative", Chem. Commun., vol. 48, (2012), pp. 11392-11394.
Nasu et al., "A highly luminescent spiro-anthracenone-based organic light-emitting diode exhibiting thermally activated delayed fluorescence", Chem. Commun., vol. 48, (2013), pp. 1-3.
Komino et al., "Suppression of Efficiency Roll-Off Characteristics in Thermally Activated Delayed Fluorescence Based Organic Light-Emitting Diodes Using Randomly Oriented Host Molecules", Chem. Mater., vol. 25, (2013), pp. 3038-3047.
Tanaka et al., "Twisted Intramolecular Charge Transfer State for Long-Wavelength Thermally Activated Delayed Fluorescence", Chem. Mater., vol. 25, (2013), pp. 3766-3771.
Zhang et al., "Design of Efficient Thermally Activated Delayed Fluorescence Materials for Pure Blue Organic Light Emitting Diodes", J. Am. Chem. Soc., vol. 134, (2012), p. 14706-14709.
Lee et al., "Oxadiazole- and triazole-based highly-efficient thermally activated delayed fluorescence emitters for organic light-emitting diodes", J. Mater. Chem. C, vol. 1, (2013), pp. 1-6.
Ishimatsu, "Solvent Effect on Thermally Activated Delayed Fluorescence by 1,2,3,5-Tetrakis(carbazol-9-yl)-4,6-dicyanobenzene", J. Phys. Chem. A, vol. 117, (2013), pp. 5607-5612.

(56) References Cited

OTHER PUBLICATIONS

Goushi et al., "Organic light-emitting diodes employing efficient reverse intersystem crossing fortriplet-to-singlet state conversion", Nature Photonics, vol. 6, (Apr. 2012), pp. 253-258.
Uoyama et al., "Highly efficient organic light-emitting diodes from delayed fluorescence", Nature, vol. 492, (Dec. 2012), pp. 234-238.
Kipphan (Handbook of Print Media: Technologies and Production Methods), ISBN 3-540-67326-1, Chapter 1.3, pp. 40-67, Chapter 1.5, pp. 117-144, Chapter 5.5, pp. 711-730.
Bulovic et al. "Transparent light-emitting devices" Nature, vol. 380, (1996) p. 29.
Gu et al., "Transparent organic light emitting devices" Appl. Phys. Lett. vol. 68, No. 19, (1996), pp. 2606-2608.

\* cited by examiner

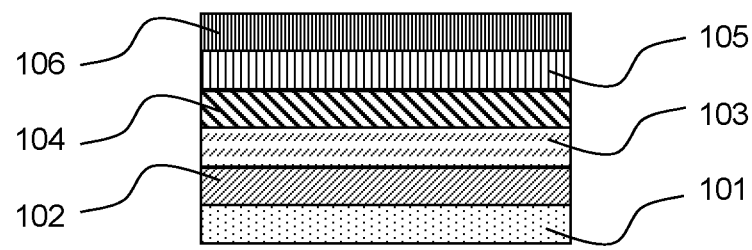

FUSED RING COMPOUND, HIGH POLYMER, MIXTURE, COMPOSITION AND ORGANIC ELECTRONIC COMPONENT

CROSS-REFERENCE TO RELATED APPLICATIONS

The present application is a national stage for International Application PCT/CN2017/112706, filed on Nov. 23, 2017, which claims priority benefit of Chinese Patent Application No. 201611051633.0 filed on Nov. 23, 2016, and entitled "Fused ring compound and application thereof in organic electronic device", the entire contents of both applications are incorporated herein for all purposes.

TECHNICAL FIELD

The present disclosure relates to the field of organic electroluminescence technology, and in particular to a fused ring compound, a polymer, a mixture, a formulation, and an application thereof in the field of organic electroluminescence.

BACKGROUND

Organic light-emitting diodes (OLEDs) have great potential for applications in optoelectronic devices such as flat panel displays and lighting, due to the synthetic diversity, relatively low manufacturing costs, and excellent optical and electrical properties of organic semiconductive materials.

Organic electroluminescence refers to the phenomenon of converting electrical energy into light energy using an organic substance. An organic electroluminescent element utilizing the phenomenon of organic electroluminescence generally is a structure which has an anode, a cathode and a layer containing an organic substance between the anode and cathode. In order to improve the efficiency and lifetime of the organic electroluminescent element, the organic substance layer has a multilayer structure, and each layer contains different organic substance. Specifically, a hole injection layer, a hole transport layer, a light emitting layer, an electron transport layer, an electron injection layer, and the like can be included. In such an electroluminescent element, if a voltage is applied between the two electrodes, holes are injected from the anode into the organic substance layer, electrons are injected from the cathode into the organic substance layer, and when the injected holes meet the electrons, excitons forms, and light emits when the excitons transits back to the ground state. This organic electroluminescent element has the properties of self-luminescence, high brightness, high efficiency, low driving voltage, wide viewing angle, high contrast, high responsiveness and the like.

In order to improve the luminous efficiency of the organic electroluminescent element, various light-emitting material systems based on fluorescence and phosphorescence have been developed, but the development of excellent blue light-emitting material, regardless of fluorescent materials or phosphorescent materials, is a great challenge. In general, at present, the organic light-emitting diodes using blue fluorescent materials are more reliable. However, most of the current blue fluorescent materials have too broad emission spectra and poor color purity, which is not conducive to high-end display, and the synthesis of such fluorescent materials is complicated which is not conducive to mass production. At the same time, the OLED of such blue fluorescent materials needs to be further improved on the stability thereof. Therefore, the development of a blue fluorescent material with narrow-band emission spectrum and good stability is needed, on one hand, for obtaining a blue light-emitting device having a longer life and a higher efficiency, and on the other hand, for the improvement of the color gamut so as to improve the display effect.

The traditional light emitting layer of the blue organic electroluminescent element uses host-guest doping structure. The present blue light-emitting host material is based on anthracene fused ring derivatives, for example, in the patents CN1914293B, CN102448945B, US2015287928A1, etc. However, these compounds have problems of insufficient luminous efficiency and brightness, and poor lifetime of the device. As a traditional blue light-emitting guest compound, an aryl vinylamine compound may be used, see WO 04/013073, WO 04/016575 and WO 04/018587. However, these compounds have poor thermal stability and easily decompose, resulting in poor lifetime of the device, which is currently the main shortcoming in the industry. Furthermore, these compounds have poor color purity and it is difficult to achieve deep blue luminescence. In addition, an organic electroluminescent element using a pyrene compound having an aromatic amine substituent group is disclosed in patents such as U.S. Pat. No. 7,233,019, KR 2006-0006760, and the like, but it is difficult to realize the deep blue luminescence due to the low color purity of blue light. Thus, there is a problem in the full color display that reflects the natural colors.

Therefore, there is still a need for further improvements in materials, particularly in light-emitting compounds, especially in blue light-emitting compounds, so that the blue light-emitting materials have deep blue luminescence and thermal stability, exhibit good efficiency and lifetime in the organic electroluminescent element, and the device is allowed to easily repeat the manufacturing and operation thereof, and is simple in material synthesis.

SUMMARY

Based on the foregoing description, an object of the present disclosure is to provide a fused ring compound, a polymer, a mixture, a formulation, and an application thereof in the field of organic electroluminescence.

A specific technical solution is described as below.

The present disclosure provides a fused ring compound represented by general formula (I):

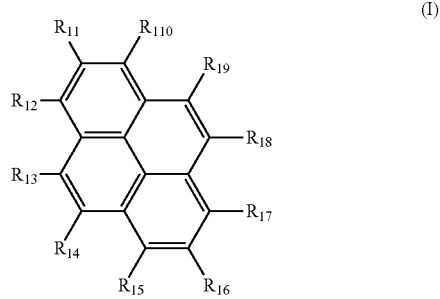

wherein each of $R_{11}$-$R_{19}$ and $R_{110}$ is independently selected from the group consisting of H, a linear alkyl containing 1 to 20 C atoms, linear alkoxy containing 1 to 20 C atoms or linear thioalkoxy group containing 1 to 20 C atoms, a branched or cyclic alkyl containing 3 to 20 C atoms, branched or cyclic alkoxy containing 3 to 20 C atoms or branched or cyclic thioalkoxy group containing 3 to 20 C atoms, a substituted or unsubstituted silyl group, a substituted keto group having 1 to 20 C atoms, an alkoxycarbonyl group containing 2 to 20 C atoms, an aryloxycarbonyl group containing 7 to 20 C atom, a cyano group (—CN), a carbamoyl group (—C(=O)NH$_2$), a haloformyl group, a formyl group (—C(=O)—H), an isocyano group, isocyanate, thiocyanate, isothiocyanate, a hydroxyl group, a nitro group, CF$_3$, Cl, Br, F, a crosslinkable group, a substituted or unsubstituted aromatic ring system containing 5 to 40 ring atoms or substituted or unsubstituted heteroaromatic ring system containing 5 to 40 ring atoms, an aryloxy group containing 5 to 40 ring atoms or heteroaryloxy group containing 5 to 40 ring atoms, or a combination of these groups; and at least one of $R_{11}$-$R_{19}$ and $R_{110}$ has a structure represented by general formula (II):

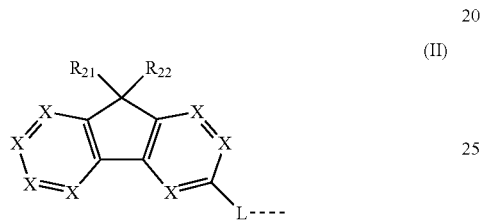

(II)

wherein

X is CR$_{23}$, and two or more Xs are the same or different;

each of $R_{21}$-$R_{23}$ is independently selected from the group consisting of H, a linear alkyl containing 1 to 20 C atoms, linear alkoxy containing 1 to 20 C atoms or linear thioalkoxy group containing 1 to 20 C atoms, a branched or cyclic alkyl containing 3 to 20 C atoms, a branched or cyclic alkoxy containing 3 to 20 C atoms or a branched or cyclic thioalkoxy group containing 3 to 20 C atoms, a substituted or unsubstituted silyl group, a substituted keto group containing 1 to 20 C atoms, an alkoxycarbonyl group containing 2 to 20 C atoms, an aryloxycarbonyl group containing 7 to 20 C atom, a cyano group (—CN), a carbamoyl group (—C(=O)NH$_2$), a haloformyl group, a formyl group (—C(=O)—H), an isocyano group, isocyanate, thiocyanate, isothiocyanate, a hydroxyl group, a nitro group, CF$_3$, Cl, Br, F, a crosslinkable group, a substituted or unsubstituted aromatic ring system containing 5 to 40 ring atoms or substituted or unsubstituted heteroaromatic ring system containing 5 to 40 ring atoms, an aryloxy group containing 5 to 40 ring atoms or heteroaryloxy group containing 5 to 40 ring atoms, or a combination of these groups;

L represents a single bond or a linking group, and the linking group is a substituted or unsubstituted aromatic ring system containing 5 to 40 ring atoms or substituted or unsubstituted heteroaromatic ring system containing 5 to 40 ring atoms, an aryloxy group containing 5 to 40 ring atoms or heteroaryloxy group containing 5 to 40 ring atoms, or a combination of these groups;

L is linked to the fused ring of the general formula (I).

In some embodiments, $R_{11}$, $R_{13}$, $R_{14}$, $R_{16}$, $R_{18}$ and $R_{19}$ are H, and at least one of $R_{12}$, $R_{15}$, $R_{17}$ and $R_{110}$ has one of the structures represented by general formulas (II-1)-(II-17):

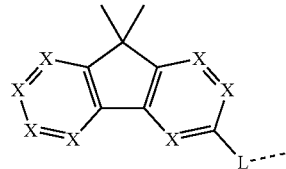

(II-1)

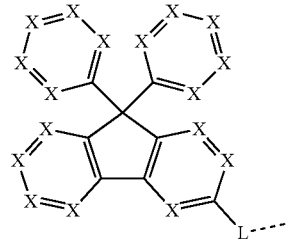

(II-2)

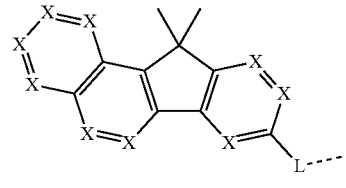

(II-3)

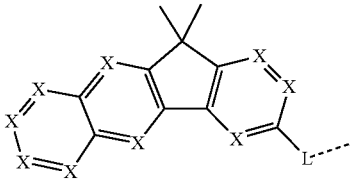

(II-4)

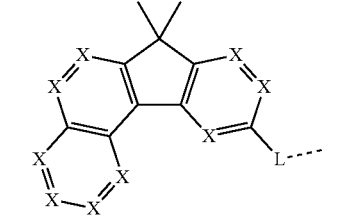

(II-5)

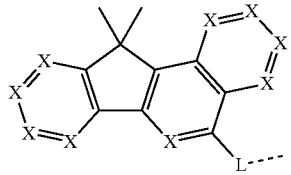

(II-6)

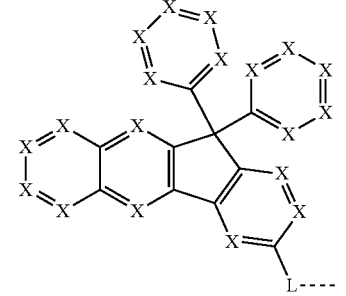

(II-7)

-continued

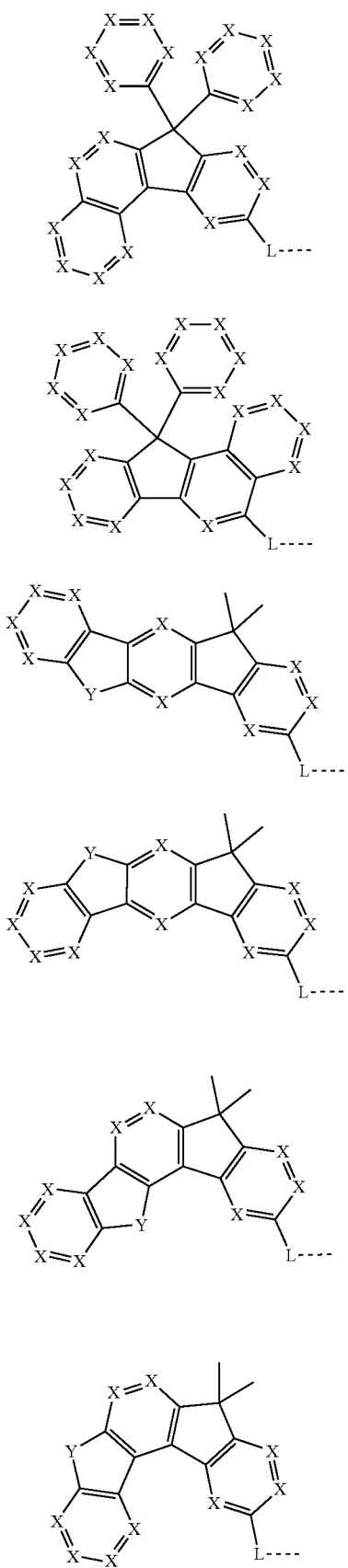

(II-8)
(II-9)
(II-10)
(II-11)
(II-12)
(II-13)

-continued

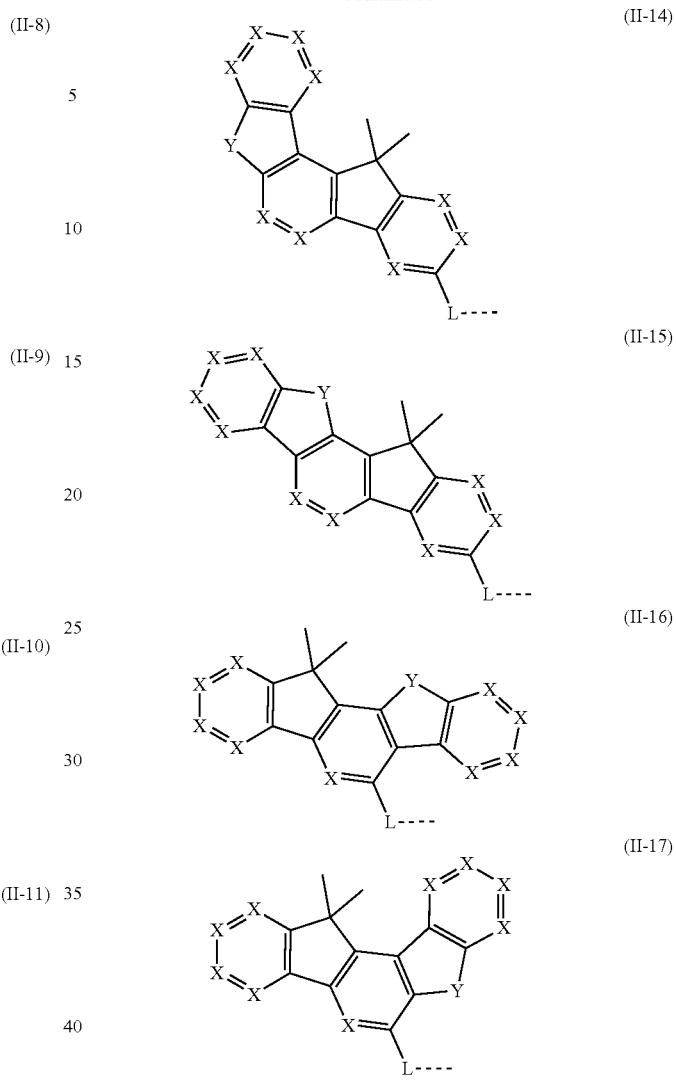

(II-14)
(II-15)
(II-16)
(II-17)

wherein
Y is selected from $CR_{25}R_{26}$, $NR_{27}$, O or S;
$R_{25}$-$R_{27}$ are selected from the group consisting of H, a linear alkyl containing 1 to 20 C atoms, linear alkoxy containing 1 to 20 C atoms or linear thioalkoxy group containing 1 to 20 C atoms, a branched or cyclic alkyl containing 3 to 20 C atoms, branched or cyclic alkoxy containing 3 to 20 C atoms or branched or cyclic thioalkoxy group containing 3 to 20 C atoms, a substituted or unsubstituted silyl group, a substituted keto group containing 1 to 20 C atoms, an alkoxycarbonyl group containing 2 to 20 C atoms, an aryloxycarbonyl group containing 7 to 20 C atom, a cyano group (—CN), a carbamoyl group (—C(=O)NH$_2$), a haloformyl group, a formyl group (—C(=O)—H), an isocyano group, isocyanate, thiocyanate, isothiocyanate, a hydroxyl group, a nitro group, $CF_3$, Cl, Br, F, a crosslinkable group, a substituted or unsubstituted aromatic ring system containing 5 to 40 ring atoms or a substituted or unsubstituted heteroaromatic ring system containing 5 to 40 ring atoms, an aryloxy group containing 5 to 40 ring atoms or heteroaryloxy group containing 5 to 40 ring atoms, or a combination of these groups.

In some embodiments, in the aforementioned fused ring compound, at least one of $R_{12}$, $R_{15}$, $R_{17}$ and $R_{110}$ is one selected from structures represented by the general formulas (II-1)-(II-17), and the rest of $R_{12}$, $R_{15}$, $R_{17}$ and $R_{110}$ is selected from group consisting of H, methyl, ethyl, n-propyl, isopropyl, cyclopropyl, n-butyl, isobutyl, sec-butyl, tert-butyl, cyclobutyl, methylbutyl, n-pentyl, sec-pentyl, cyclopentyl, n-hexyl, cyclohexyl, n-heptyl, cycloheptyl, n-octyl, cyclooctyl, ethylhexyl, trifluoromethyl, pentafluoroethyl, trifluoroethyl, vinyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, octynyl, methoxy, trifluoromethoxy, ethoxy, n-propoxy, isopropoxy, n-butoxy, isobutoxy, sec-butoxy, tert-butoxy, methylbutoxy, trimethylsilane, and the following aromatic structures:

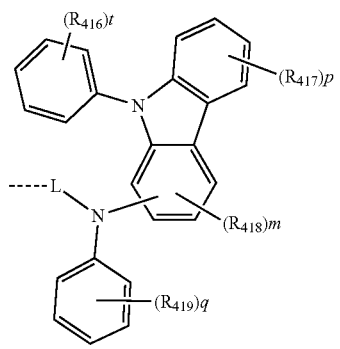

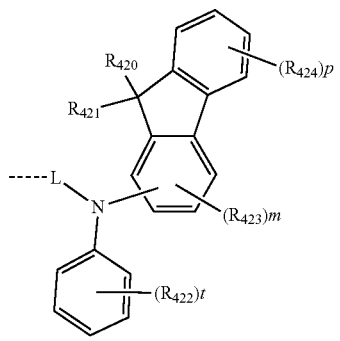

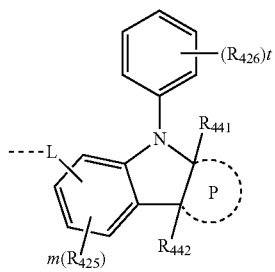

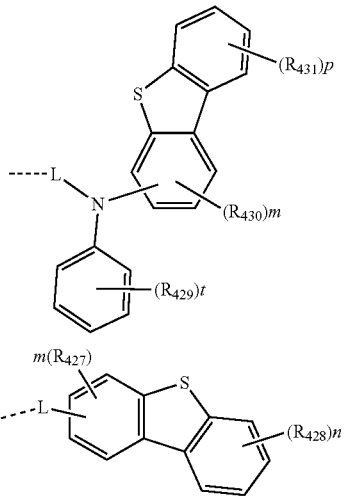

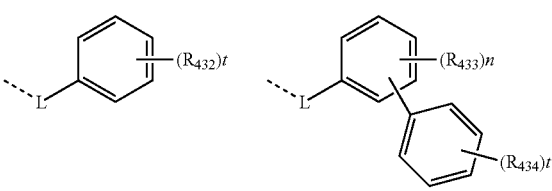

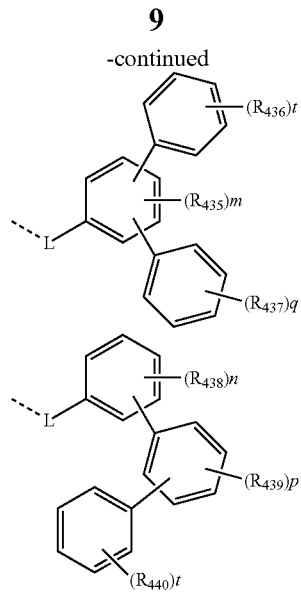

wherein $R_{41}$-$R_{49}$ and $R_{410}$-$R_{440}$ are selected from the group consisting of H, a linear alkyl containing 1 to 20 C atoms, linear alkoxy containing 1 to 20 C atoms or linear thioalkoxy group containing 1 to 20 C atoms, a branched or cyclic alkyl containing 3 to 20 C atoms, branched or cyclic alkoxy containing 3 to 20 C atoms or branched or cyclic thioalkoxy group containing 3 to 20 C atoms, a substituted or unsubstituted silyl group, a substituted keto group containing 1 to 20 C atoms, an alkoxycarbonyl group containing 2 to 20 C atoms, an aryloxycarbonyl group containing 7 to 20 C atom, a cyano group (—CN), a carbamoyl group (—C(=O)NH$_2$), a haloformyl group, a formyl group (—C(=O)—H), an isocyano group, isocyanate, thiocyanate, isothiocyanate, a hydroxyl group, a nitro group, CF$_3$, Cl, Br, F, a crosslinkable group, a substituted or unsubstituted aromatic ring system containing 5 to 40 ring atoms or a substituted or unsubstituted heteroaromatic ring system containing 5 to 40 ring atoms, an aryloxy group containing 5 to 40 ring atoms or heteroaryloxy group containing 5 to 40 ring atoms, or a combination of these groups, wherein one or more groups of $R_{41}$-$R_{49}$ and $R_{410}$-$R_{440}$ can form a monocyclic or polycyclic aliphatic or aromatic ring system with each other and/or with a ring bonded to said groups.

m is an integer of 0 to 3, each of n, p and s is independently an integer of 0 to 4, and each of t and q is independently an integer of 0 to 5;

P is a saturated naphthene containing 3 to 8 C atoms;

L represents a single bond or a linking group, and the linking group can be a substituted or unsubstituted aromatic ring system containing 5 to 40 ring atoms or substituted or unsubstituted heteroaromatic ring system containing 5 to 40 ring atoms, an aryloxy group containing 5 to 40 ring atoms or heteroaryloxy group containing 5 to 40 ring atoms, or a combination of these groups;

L is linked to the fused ring of the general formula (I).

The present disclosure further provides a polymer having a repeating unit comprising a group formed by the above fused ring compounds losing at least one hydrogen atom.

The present disclosure still further provides a mixture comprising the fused ring compound or the polymer as described above, and a second organic functional material. The second organic functional material may be at least one selected from the group consisting of: a hole (also called electron hole) injection or transport material (HIM/HTM), a hole blocking material (HBM), an electron injection or transport material (EIM/ETM), an electron blocking material (EBM), an organic matrix material (Host), a singlet emitter (fluorescent emitter), a triplet emitter (phosphorescent emitter), a thermally activated delayed fluorescent material (TADF material) and an organic dye.

The present disclosure further provides a formulation comprising the fused ring compound or the polymer as described above, and an organic solvent.

Another object of the present disclosure is to provide an organic electronic device comprising the fused ring compound or the polymer as described above.

The organic electronic device may be selected from the group consisting of an organic light-emitting diode (OLED), an organic photovoltaic cell (OPV), an organic light-emitting electrochemical cell (OLEEC), an organic field effect transistor (OFET), an organic light-emitting field effect transistor, an organic laser, an organic spintronic device, an organic sensor, and an organic plasmon emitting diode.

In some embodiments, the organic electronic device is an organic electroluminescent device, the organic electronic device comprises a light emitting layer comprising the fused ring compound or the polymer as described above.

Advantageous Effects

The fused ring compound described above has fluorescence emission at a short light emission wavelength, and light-emission spectrum with a narrow half-peak width, so that this substance has a deep blue fluorescence emission, and with high luminous efficiency. The organic electroluminescent element prepared with the fused ring compound as a guest has deep blue color coordinates, high luminous efficiency, and long device lifetime.

BRIEF DESCRIPTION OF THE DRAWINGS

FIG. 1 is a structural schematic diagram of an organic electroluminescent device provided by an embodiment of the disclosure;

In the FIGURE, a substrate is denoted by 101, an anode is denoted by 102, a hole injection layer (HIL) or hole transport layer (HTL) is denoted by 103, a light emitting layer is denoted by 104, an electron injection layer (EIL) or electron transport layer (ETL) is denoted by 105, and a cathode is denoted by 106.

DETAILED DESCRIPTION OF THE DISCLOSURE

In order to facilitate the understanding of the present disclosure, the present disclosure will be described more fully hereinafter with reference to the related accompanying drawings. Preferable embodiments are presented in the drawings. However, the present disclosure may be embodied in many different forms and is not limited to the embodiments described herein. Rather, these embodiments are provided so that the understanding of the disclosure of the present disclosure will be more thorough.

All technical and scientific terms used herein have the same meaning as commonly understood by the skilled person in the art to which this disclosure belongs, unless otherwise defined. The terms used in the specification of the disclosure herein are for the purpose of describing specific embodiments only and are not intended to limit the present disclosure. The term "and/or" used herein includes any and all combinations of one or more of the related listed items.

In the present disclosure, Host material and Matrix material have the same meaning and they are interchangeable.

In the present disclosure, the metal organic clathrate, metal organic complexe, and organometallic complexe have the same meaning and are interchangeable.

In the present disclosure, formulation, printing ink, ink and inks have the same meaning and can be used interchangeably.

The present disclosure provides a fused ring compound represented by general formula (I):

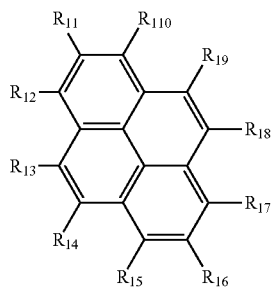

wherein, each of $R_{11}$-$R_{19}$ and $R_{110}$ is independently selected from the group consisting of H, a linear alkyl containing 1 to 20 C atoms, linear alkoxy containing 1 to 20 C atoms or linear thioalkoxy group containing 1 to 20 C atoms, a branched or cyclic alkyl containing 3 to 20 C atoms, branched or cyclic alkoxy containing 3 to 20 C atoms or branched or cyclic thioalkoxy group containing 3 to 20 C atoms, a substituted or unsubstituted silyl group, a substituted keto group containing 1 to 20 C atoms, an alkoxycarbonyl group containing 2 to 20 C atoms, an aryloxycarbonyl group containing 7 to 20 C atom, a cyano group (—CN), a carbamoyl group (—C(=O)NH$_2$), a haloformyl group, a formyl group (—C(=O)—H), an isocyano group, isocyanate, thiocyanate, isothiocyanate, a hydroxyl group, a nitro group, CF$_3$, Cl, Br, F, a crosslinkable group, a substituted or unsubstituted aromatic ring system containing 5 to 40 ring atoms or substituted or unsubstituted heteroaromatic ring system containing 5 to 40 ring atoms, an aryloxy group containing 5 to 40 ring atoms or heteroaryloxy group containing 5 to 40 ring atoms, or a combination of these groups, wherein one or more groups of $R_{11}$-$R_{19}$ and $R_{110}$ can form a monocyclic or polycyclic aliphatic or aromatic ring system with each other and/or with a ring bonded to said groups;

And, at least one of the $R_{11}$-$R_{19}$ and $R_{110}$ has a structure represented by the general formula (II):

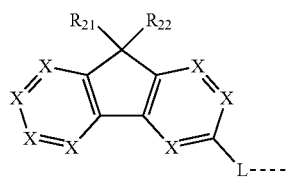

wherein

X is $CR_{23}$, and two or more Xs can be the same or different.

each of $R_{21}$-$R_{23}$ is independently selected from the group consisting of H, a linear alkyl containing 1 to 20 C atoms, linear alkoxy containing 1 to 20 C atoms or linear thioalkoxy group containing 1 to 20 C atoms, a branched or cyclic alkyl containing 3 to 20 C atoms, branched or cyclic alkoxy containing 3 to 20 C atoms or branched or cyclic thioalkoxy group containing 3 to 20 C atoms, a substituted or unsubstituted silyl group, a substituted keto group containing 1 to 20 C atoms, an alkoxycarbonyl group containing 2 to 20 C atoms, an aryloxycarbonyl group containing 7 to 20 C atom, a cyano group (—CN), a carbamoyl group (—C(=O)NH$_2$), a haloformyl group, a formyl group (—C(=O)—H), an isocyano group, isocyanate, thiocyanate, isothiocyanate, a hydroxyl group, a nitro group, CF$_3$, Cl, Br, F, a crosslinkable group, a substituted or unsubstituted aromatic ring system containing 5 to 40 ring atoms or substituted or unsubstituted heteroaromatic ring system containing 5 to 40 ring atoms, an aryloxy group containing 5 to 40 ring atoms or heteroaryloxy group containing 5 to 40 ring atoms, or a combination of these groups, wherein one or more groups of $R_{21}$-$R_{23}$ can form a monocyclic or polycyclic aliphatic or aromatic ring system with each other and/or a the ring bonded to said groups.

L represents a single bond or a linking group. The linking group can be a substituted or unsubstituted aromatic ring system containing 5 to 40 ring atoms or substituted or unsubstituted heteroaromatic ring system containing 5 to 40 ring atoms, an aryloxy group containing 5 to 40 ring atoms or heteroaryloxy group containing 5 to 40 ring atoms, or a combination of these groups, wherein one or more groups can form a monocyclic or polycyclic aliphatic or aromatic ring system with each other and/or with a ring bonded to said groups.

The dotted line indicates a single bond linked to the fused ring of the general formula (I).

In certain embodiments, each of $R_{11}$-$R_{19}$ and $R_{110}$ is independently H, a linear alkyl, alkoxy or thioalkoxy group containing 1 to 10 C atoms, a branched or cyclic alkyl, alkoxy or thioalkoxy group containing 3 to 10 C atoms, a substituted or unsubstituted silyl group, a substituted keto group containing 1 to 10 C atoms, an alkoxycarbonyl group containing 2 to 10 C atoms, an aryloxycarbonyl group containing 7 to 10 C atom, a cyano group (—CN), a carbamoyl group (—C(=O)NH$_2$), a haloformyl group, a formyl group (—C(=O)—H), an isocyano group, isocyanate, thiocyanate, isothiocyanate, a hydroxyl group, a nitro group, CF$_3$, Cl, Br, F, a crosslinkable group, a substituted or unsubstituted aromatic or heteroaromatic ring system containing 5 to 20 ring atoms, an aryloxy or heteroaryloxy group containing 5 to 20 ring atoms, or a combination of these systems, wherein one or more groups of $R_{11}$-$R_{19}$ and $R_{110}$ can form a monocyclic or polycyclic aliphatic or aromatic ring system with each other and/or with a ring bonded to said groups.

In some other preferred embodiments, each of $R_{21}$-$R_{23}$ is independently selected from the group consisting of H, a linear alkyl containing 1 to 10 C atoms, linear alkoxy containing 1 to 10 C atoms or linear thioalkoxy group containing 1 to 10 C atoms, a branched or cyclic alkyl containing 3 to 10 C atoms, branched or cyclic alkoxy containing 3 to 10 C atoms or branched or cyclic thioalkoxy group containing 3 to 10 C atoms, a substituted or unsubstituted silyl group, a substituted keto group containing 1 to 10 C atoms, an alkoxycarbonyl group containing 2 to 10 C atoms, an aryloxycarbonyl group containing 7 to 10 C atom, a cyano group (—CN), a carbamoyl group (—C(=O)NH$_2$), a haloformyl group, a formyl group (—C(=O)—H), an isocyano group, isocyanate, thiocyanate, isothiocyanate, a hydroxyl group, a nitro group, CF$_3$, Cl, Br, F, a crosslinkable group, a substituted or unsubstituted aromatic ring system containing 5 to 20 ring atoms or substituted or unsubstituted heteroaromatic ring system containing 5 to 20 ring atoms, an aryloxy group containing 5 to 20 ring atoms or heteroaryloxy group containing 5 to 20 ring atoms, or a combination of these groups, wherein one or more groups of R$_{21}$-R$_{23}$ can form a monocyclic or polycyclic aliphatic or aromatic ring system with each other and/or with a ring bonded to said groups.

In an embodiment, L is a single bond.

In another embodiment, L is a substituted or unsubstituted aromatic ring system containing 5 to 20 ring atoms or substituted or unsubstituted heteroaromatic ring system containing 5 to 20 ring atoms, an aryloxy group containing 5 to 20 ring atoms or heteroaryloxy group containing 5 to 20 ring atoms, or a combination of these groups, wherein one or more groups can form a monocyclic or polycyclic aliphatic or aromatic ring system with each other and/or with a ring bonded to said groups.

In some embodiments, L is a substituted or unsubstituted aromatic ring system containing 5 to 15 ring atoms or substituted or unsubstituted heteroaromatic ring system containing 5 to 15 ring atoms, an aryloxy group containing 5 to 15 ring atoms or heteroaryloxy group containing 5 to 15 ring atoms, or a combination of these groups, wherein one or more groups can form a monocyclic or polycyclic aliphatic or aromatic ring system with each other and/or with a ring bonded to said groups.

In some embodiments, L is a substituted or unsubstituted aromatic ring system containing 5 to 10 ring atoms or substituted or unsubstituted heteroaromatic ring system containing 5 to 10 ring atoms, an aryloxy group containing 5 to 10 ring atoms or heteroaryloxy group containing 5 to 10 ring atoms, or a combination of these groups, wherein one or more groups can form a monocyclic or polycyclic aliphatic or aromatic ring system with each other and/or with a ring bonded to said groups.

In one embodiment, the ring system of the aromatic ring system of the present disclosure contains 5 to 15 carbon atoms, further, the ring system of the aromatic ring system of the present disclosure contains 5 to 10 carbon atoms. The ring system of the heteroaromatic ring system contains 2 to 15 carbon atoms, further, the ring system of the heteroaromatic ring system contains 2 to 10 carbon atoms, and the heteroaromatic ring system contains at least one heteroatom, and the carbon atom and heteroatom of the heteroaromatic ring system comprise at least 4 atoms in total. Especially, the heteroatom is selected from Si, N, P, O, S and/or Ge, particularly selected from Si, N, P, O and/or S, and even more particularly selected from N, O or S.

The aromatic ring system or aromatic group of the present disclosure described above refers to a hydrocarbyl group comprising at least one aromatic ring, including a monocyclic group and a polycyclic ring system. The heteroaromatic ring system or heteroaromatic group described above refers to a hydrocarbyl group (containing a heteroatom) comprising at least one heteroaromatic ring, including a monocyclic group and a polycyclic ring system. The polycyclic ring may have two or more rings, wherein two carbon atoms are shared by two adjacent rings, i.e., a fused ring. At least one ring in such polycyclic ring is aromatic or heteroaromatic. For the purpose of the present disclosure, the aromatic or heteroaromatic ring systems not only include aromatic or heteroaromatic systems, but also have a plurality of aryl groups or heteroaryl groups spaced by short non-aromatic units (<10% of non-H atoms, preferably less than 5% of non-H atoms, such as C, N or O atoms). Therefore, systems such as 9,9'-spirobifluorene, 9,9-diarylfluorene, triarylamine, diaryl ether and the like are also considered to be aromatic ring systems for the purpose of this disclosure.

Specifically, examples of the aromatic group include: benzene, naphthalene, anthracene, phenanthrene, perylene, tetracene, pyrene, benzopyrene, triphenylene, acenaphthene, fluorene, spirofluorene and derivatives thereof.

Specifically, examples of the heteroaromatic group include: furan, benzofuran, dibenzofuran, thiophene, benzothiophene, dibenzothiophene, pyrrole, pyrazole, triazole, imidazole, oxazole, oxadiazole, thiazole, tetrazole, indole, carbazole, pyrroloimidazole, pyrrolopyrrole, thienopyrrole, thienothiophene, furopyrrole, furofuran, thienofuran, benzisoxazole, benzisothiazole, benzimidazole, pyridine, pyrazine, pyridazine, pyrimidine, triazine, quinoline, isoquinoline, cinnoline, quinoxaline, phenanthridine, perimidine, quinazoline, quinazolinone, and derivatives thereof.

In one embodiment, the linking group L in the general formula (II) may comprise one or more combinations of the following structural groups:

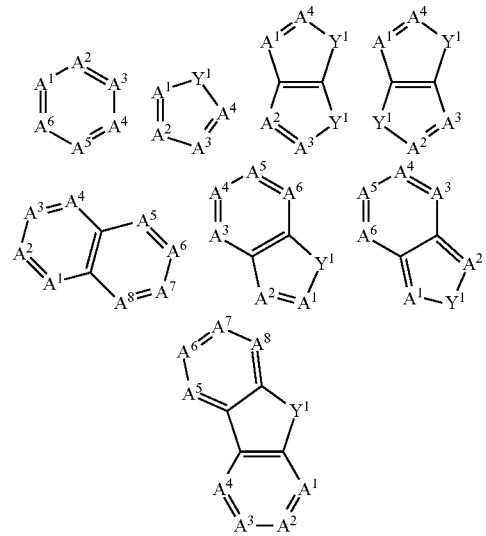

wherein each of A$^1$, A$^2$, A$^3$, A$^4$, A$^5$, A$^6$, A$^7$ and A$^8$ is independently selected from CR$^3$ or N;

Y$^1$ is selected from CR$^4$R$^5$, SiR$^4$R$^5$, NR$^3$, C(=O), S or O;

R$^3$, R$^4$, and R$^5$ are selected from the group consisting of H, a linear alkyl containing 1 to 20 C atoms, linear alkoxy containing 1 to 20 C atoms or linear thioalkoxy group containing 1 to 20 C atoms, a branched or cyclic alkyl containing 3 to 20 C atoms, branched or cyclic alkoxy containing 3 to 20 C atoms or branched or cyclic thioalkoxy group containing 3 to 20 C atoms, a substituted or unsubstituted silyl group, a substituted keto group containing 1 to 20 C atoms, an alkoxycarbonyl group containing 2 to 20 C atoms, an aryloxycarbonyl group containing 7 to 20 C atom, a cyano group (—CN), a carbamoyl group (—C(=O)NH$_2$), a haloformyl group, a formyl group (—C(=O)—H), an isocyano group, isocyanate, thiocyanate, isothiocyanate, a hydroxyl group, a nitro group, CF$_3$, Cl, Br, F, a crosslinkable group, a substituted or unsubstituted aromatic ring system containing 5 to 40 ring atoms or substituted or unsubstituted heteroaromatic ring system containing 5 to 40 ring atoms, an aryloxy group containing 5 to 40 ring atoms or heteroaryloxy group containing 5 to 40 ring atoms, or a combination of these groups, wherein one or more groups of $R^3$, $R^4$, and $R^5$ may form a monocyclic or polycyclic aliphatic or aromatic ring system with each other and/or with a ring bonded to said groups.

In another embodiment, the linking group L in the general formula (II) is one selected from the following structural groups, wherein the H in the ring may be arbitrarily substituted:

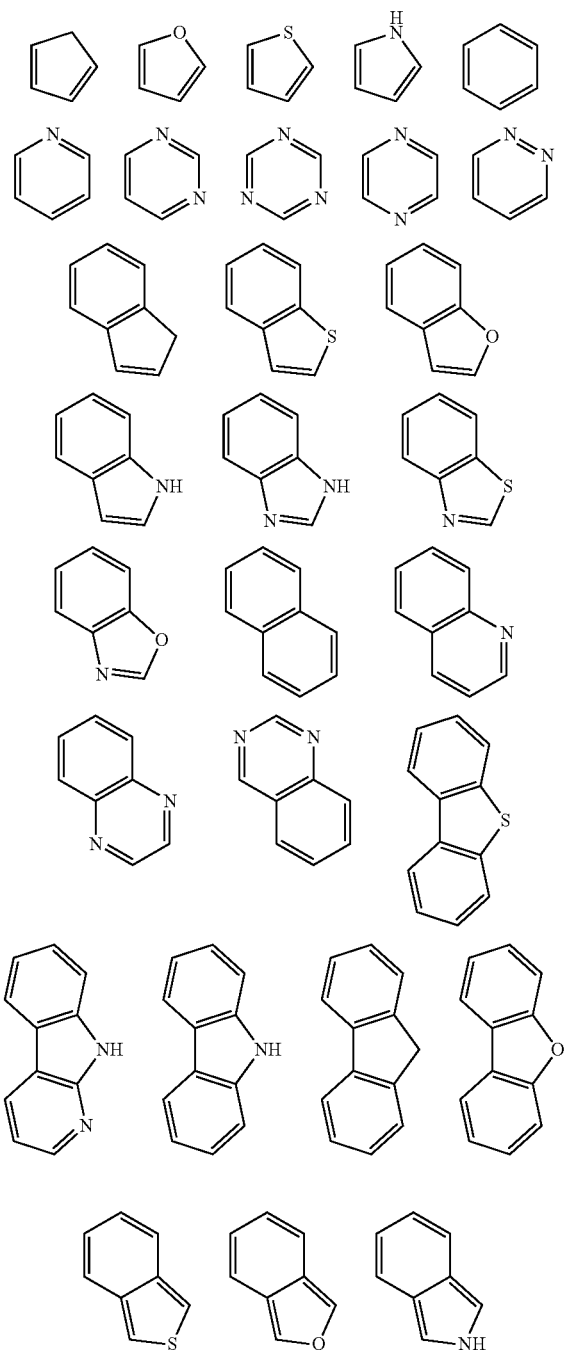

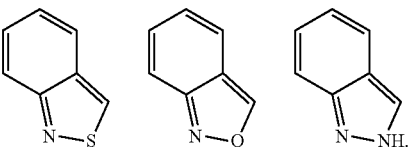

According to the fused ring compound of the present disclosure, in some of these embodiments, $R_{11}$, $R_{13}$, $R_{14}$, $R_{16}$, $R_{18}$ and $R_{19}$ are all H, and at least one of $R_{12}$, $R_{15}$, $R_{17}$ and $R_{110}$ has one of the structures represented by general formula (II-1) to general formula (II-17):

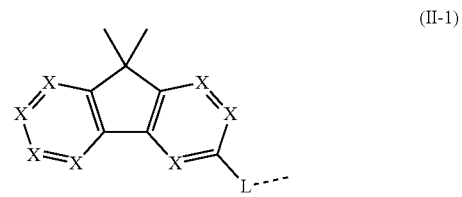

(II-1)

(II-2)

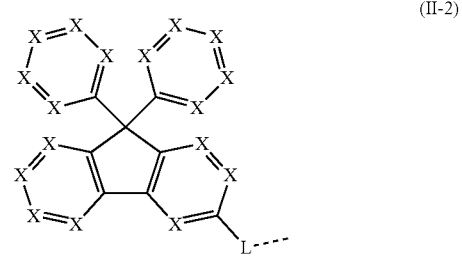

(II-3)

(II-4)

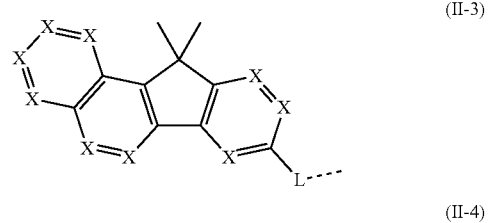

(II-5)

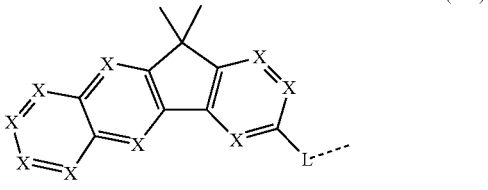

(II-6)

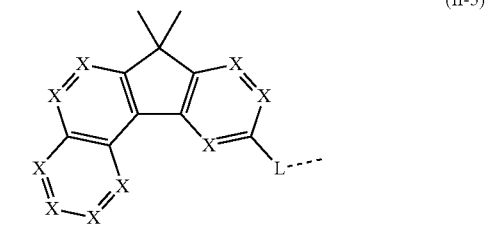

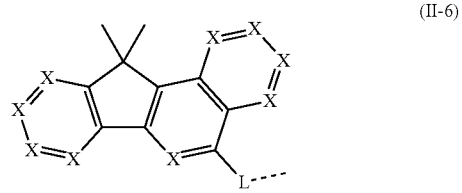

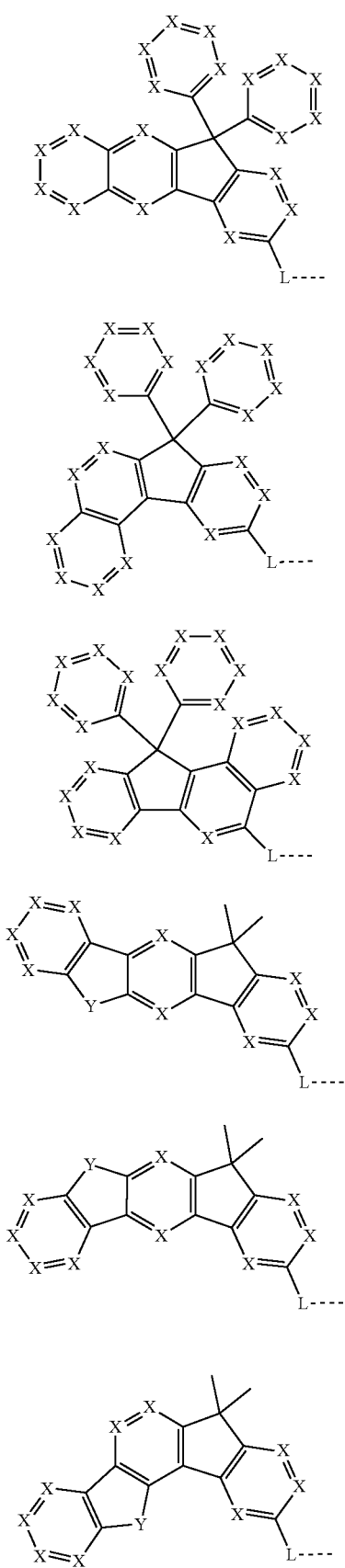

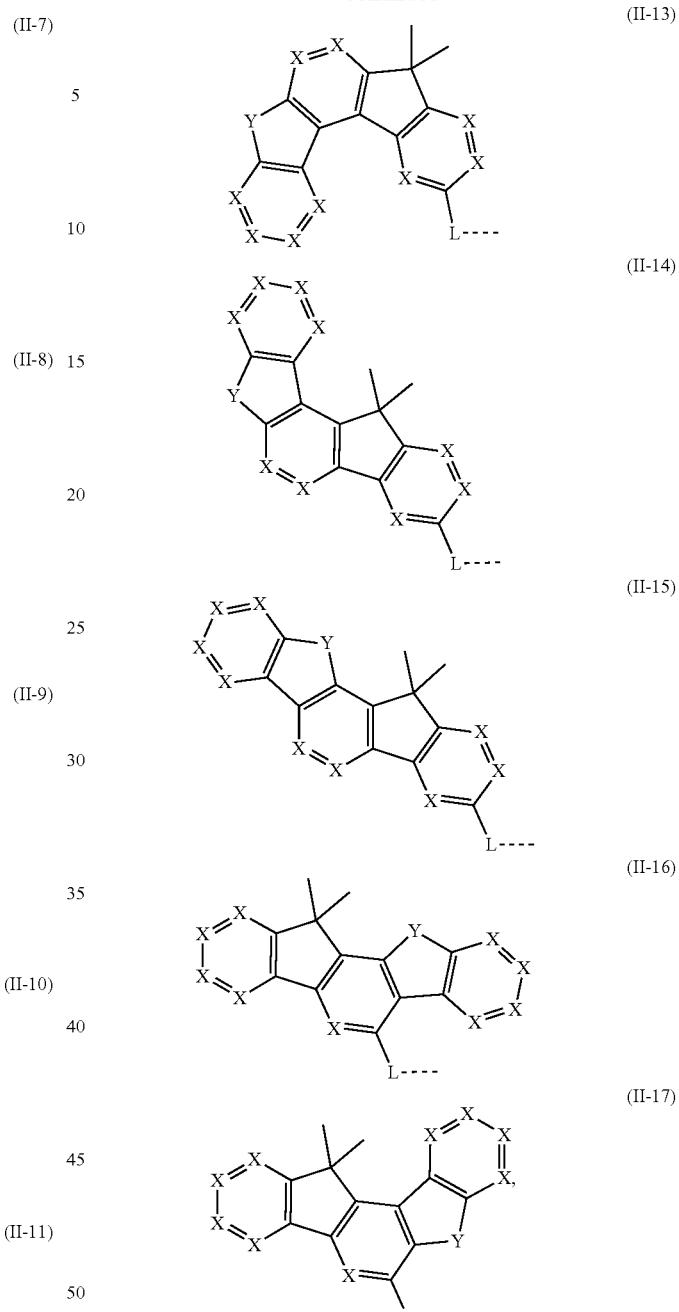

wherein

X is selected from CR$_{24}$ or N;

Y is selected from CR$_{25}$R$_{26}$, NR$_{27}$, O or S;

each of R$_{24}$-R$_{27}$ is independently selected from the group consisting of H, a linear alkyl containing 1 to 20 C atoms, linear alkoxy containing 1 to 20 C atoms or linear thioalkoxy group containing 1 to 20 C atoms, a branched or cyclic alkyl containing 3 to 20 C atoms, branched or cyclic alkoxy containing 3 to 20 C atoms or branched or cyclic thioalkoxy group containing 3 to 20 C atoms, a substituted or unsubstituted silyl group, a substituted keto group containing 1 to 20 C atoms, an alkoxycarbonyl group containing 2 to 20 C atoms, an aryloxycarbonyl group containing 7 to 20 C atom, a cyano group (—CN), a carbamoyl group (—C(=O)NH$_2$), a haloformyl group, a formyl group (—C(=O)—H), an isocyano group, isocyanate, thiocyanate, isothiocyanate, a hydroxyl group, a nitro group, $CF_3$, Cl, Br, F, a crosslinkable group, a substituted or unsubstituted aromatic ring system containing 5 to 40 ring atoms or substituted or unsubstituted heteroaromatic ring system containing 5 to 40 ring atoms, an aryloxy group containing 5 to 40 ring atoms or heteroaryloxy group containing 5 to 40 ring atoms, or a combination of these groups, wherein one or more groups of $R_{24}$-$R_{27}$ can form a monocyclic or polycyclic aliphatic or aromatic ring system with each other and/or with a ring bonded to said groups.

In a further embodiment, $R_{24}$-$R_{27}$ are selected from the group consisting of H, a linear alkyl containing 1 to 10 C atoms, linear alkoxy containing 1 to 10 C atoms or linear thioalkoxy group containing 1 to 10 C atoms, a branched or cyclic alkyl containing 3 to 10 C atoms, branched or cyclic alkoxy containing 3 to 10 C atoms or branched or cyclic thioalkoxy group containing 3 to 10 C atoms, a substituted or unsubstituted silyl group, a substituted keto group containing 1 to 10 C atoms, an alkoxycarbonyl group containing 2 to 10 C atoms, an aryloxycarbonyl group containing 7 to 10 C atom, a cyano group (—CN), a carbamoyl group (—C(=O)NH$_2$), a haloformyl group, a formyl group (—C(=O)—H), an isocyano group, isocyanate, thiocyanate, isothiocyanate, a hydroxyl group, a nitro group, $CF_3$, Cl, Br, F, a crosslinkable group, a substituted or unsubstituted aromatic ring system containing 5 to 20 ring atoms or substituted or unsubstituted heteroaromatic ring system containing 5 to 20 ring atoms, an aryloxy group containing 5 to 20 ring atoms or heteroaryloxy group containing 5 to 20 ring atoms, or a combination of these groups, wherein one or more groups of $R_{24}$-$R_{27}$ can form a monocyclic or polycyclic aliphatic or aromatic ring system with each other and/or with a ring bonded to said groups.

L represents a single bond or a linking group as defined in the above general formula (II).

According to the fused ring compound of the present disclosure, in some of the embodiments, in the fused ring compound, only one of the four substitution positions of $R_{12}$, $R_{15}$, $R_{17}$ and $R_{110}$ is selected from structures represented by the general formulas (II-1)-(II-17);

In other embodiments, in the fused ring compound of the present disclosure, two of the four substitution positions of $R_{12}$, $R_{15}$, $R_{17}$ and $R_{110}$ are independently selected from structures represented by the general formulas (II-1)-(II-17);

In other embodiments, in the fused ring compound of the present disclosure, three of the four substitution positions of $R_{12}$, $R_{15}$, $R_{17}$ and $R_{110}$ are independently selected from structures represented by the general formulas (II-1)-(II-17);

In other embodiments, in the fused ring compound of the present disclosure, four of the four substitution positions of $R_{12}$, $R_{15}$, $R_{17}$ and $R_{110}$ are all independently selected from structures represented by the general formulas (II-1)-(II-17);

In other embodiments, in the fused ring compound of the present disclosure, $R_{15}$ and $R_{110}$ are all independently selected from structures represented by the general formulas (II-1)-(II-17);

In other embodiments, in the fused ring compound of the present disclosure, $R_{12}$, and $R_{17}$ are independently selected from the group consisting of a linear alkyl containing 1 to 20 C atoms, a branched or cyclic alkyl containing 3 to 20 C atoms, a substituted or unsubstituted aromatic ring system containing 5 to 40 ring atoms or substituted or unsubstituted heteroaromatic ring system containing 5 to 40 ring atoms, or a combination of these groups.

In some of the embodiments, in the fused ring compound of the present disclosure, at least one of the four substitution positions of $R_{12}$, $R_{15}$, $R_{17}$ and $R_{110}$ is selected from structures represented by the general formulas (II-1)-(II-17), and the remaining positions are selected from group consisting of H, methyl, ethyl, n-propyl, isopropyl, cyclopropyl, n-butyl, isobutyl, sec-butyl, tert-butyl, cyclobutyl, methylbutyl, n-pentyl, sec-pentyl, cyclopentyl, n-hexyl, cyclohexyl, n-heptyl, cycloheptyl, n-octyl, cyclooctyl, ethylhexyl, trifluoromethyl, pentafluoroethyl, trifluoroethyl, vinyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, octynyl, methoxy, trifluoromethoxy, ethoxy, n-propoxy, isopropoxy, n-butoxy, isobutoxy, sec-butoxy, tert-butoxy, methylbutoxy, trimethylsilane, and the following aromatic structures:

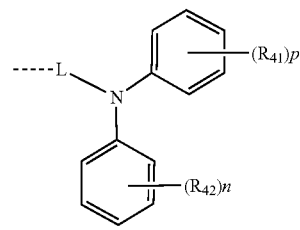

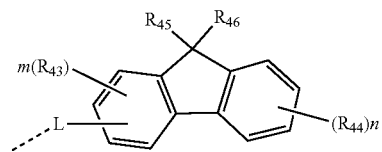

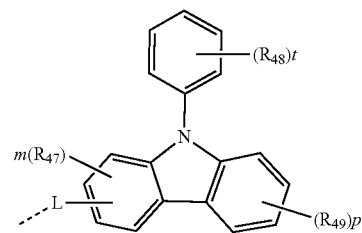

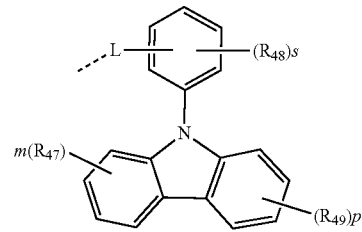

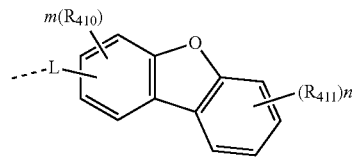

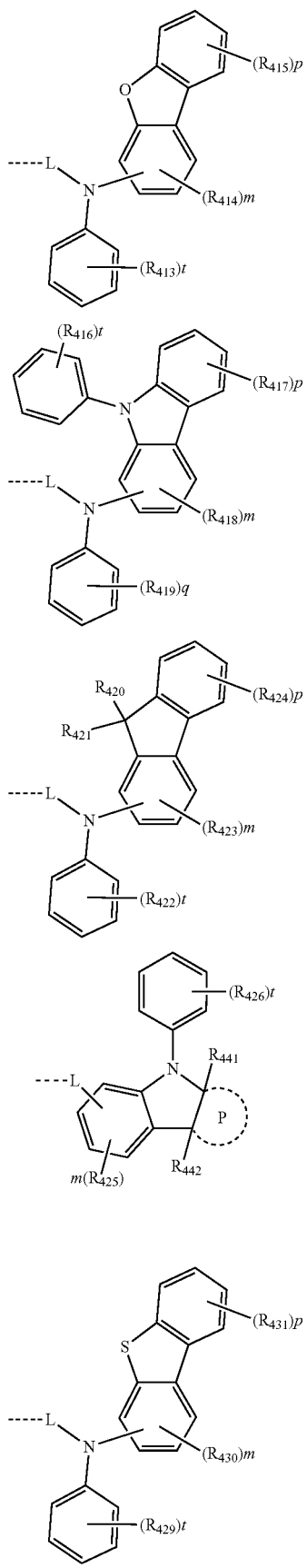

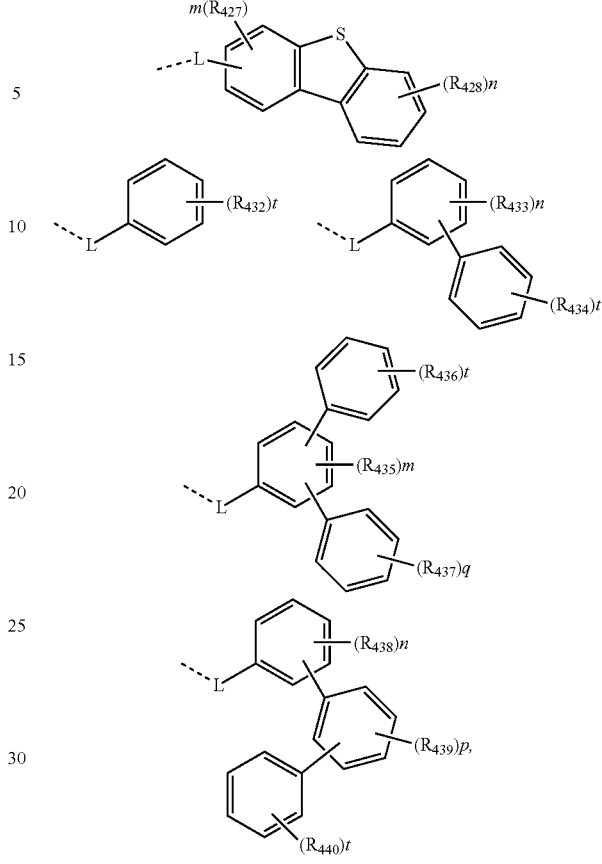

wherein $R_{41}$-$R_{49}$ and $R_{410}$-$R_{442}$ are selected from group consisting of H, a linear alkyl containing 1 to 20 C atoms, linear alkoxy containing 1 to 20 C atoms or linear thioalkoxy group containing 1 to 20 C atoms, a branched or cyclic alkyl containing 3 to 20 C atoms, branched or cyclic alkoxy containing 3 to 20 C atoms or branched or cyclic thioalkoxy group containing 3 to 20 C atoms, a substituted or unsubstituted silyl group, a substituted keto group containing 1 to 20 C atoms, an alkoxycarbonyl group containing 2 to 20 C atoms, an aryloxycarbonyl group containing 7 to 20 C atom, a cyano group (—CN), a carbamoyl group (—C(=O)NH$_2$), a haloformyl group, a formyl group (—C(=O)—H), an isocyano group, isocyanate, thiocyanate, isothiocyanate, a hydroxyl group, a nitro group, CF$_3$, Cl, Br, F, a crosslinkable group, a substituted or unsubstituted aromatic ring system containing 5 to 40 ring atoms or substituted or unsubstituted heteroaromatic ring system containing 5 to 40 ring atoms, an aryloxy group containing 5 to 40 ring atoms or heteroaryloxy group containing 5 to 40 ring atoms, or a combination of these groups.

Particularly, $R_{41}$-$R_{49}$ and $R_{410}$-$R_{440}$ are selected from group consisting of H, a linear alkyl containing 1 to 10 C atoms, linear alkoxy containing 1 to 10 C atoms or linear thioalkoxy group containing 1 to 10 C atoms, a branched or cyclic alkyl containing 3 to 10 C atoms, branched or cyclic alkoxy containing 3 to 10 C atoms or branched or cyclic thioalkoxy group containing 3 to 10 C atoms, a substituted or unsubstituted silyl group, a substituted keto group containing 1 to 10 C atoms, an alkoxycarbonyl group containing 2 to 10 C atoms, an aryloxycarbonyl group containing 7 to 10 C atom, a cyano group (—CN), a carbamoyl group (—C(═O)NH₂), a haloformyl group, a formyl group (—C(═O)—H), an isocyano group, isocyanate, thiocyanate, isothiocyanate, a hydroxyl group, a nitro group, CF₃, Cl, Br, F, a crosslinkable group, a substituted or unsubstituted aromatic ring system containing 5 to 20 ring atoms or substituted or unsubstituted heteroaromatic ring system containing 5 to 20 ring atoms, an aryloxy group containing 5 to 20 ring atoms or heteroaryloxy group containing 5 to 20 ring atoms, or a combination of these groups, wherein one or more of the groups can form a monocyclic or polycyclic aliphatic or aromatic ring system with each other and/or with the ring bonded to said groups.

m is an integer of 0 to 3, each of n, p and s is independently an integer of 0 to 4, and each of t and q is independently an integer of 0 to 5.

P is a saturated naphthene containing 3 to 8 C atoms;

L represents a single bond or a linking group as defined in above chemical formula (II).

The dotted line indicates the single bond linked to the fused ring of the general formula (III).

In an embodiment, at least part of H in the fused ring compound of the present disclosure is substituted by deuterium, further, 10% H is substituted by deuterium, still further, 20% H is substituted by deuterium, even further, 30% H is substituted by deuterium, particularly, 40% H is substituted by deuterium.

The specific example of the fused ring compound according to the present disclosure is as follows, but is not limited thereto:

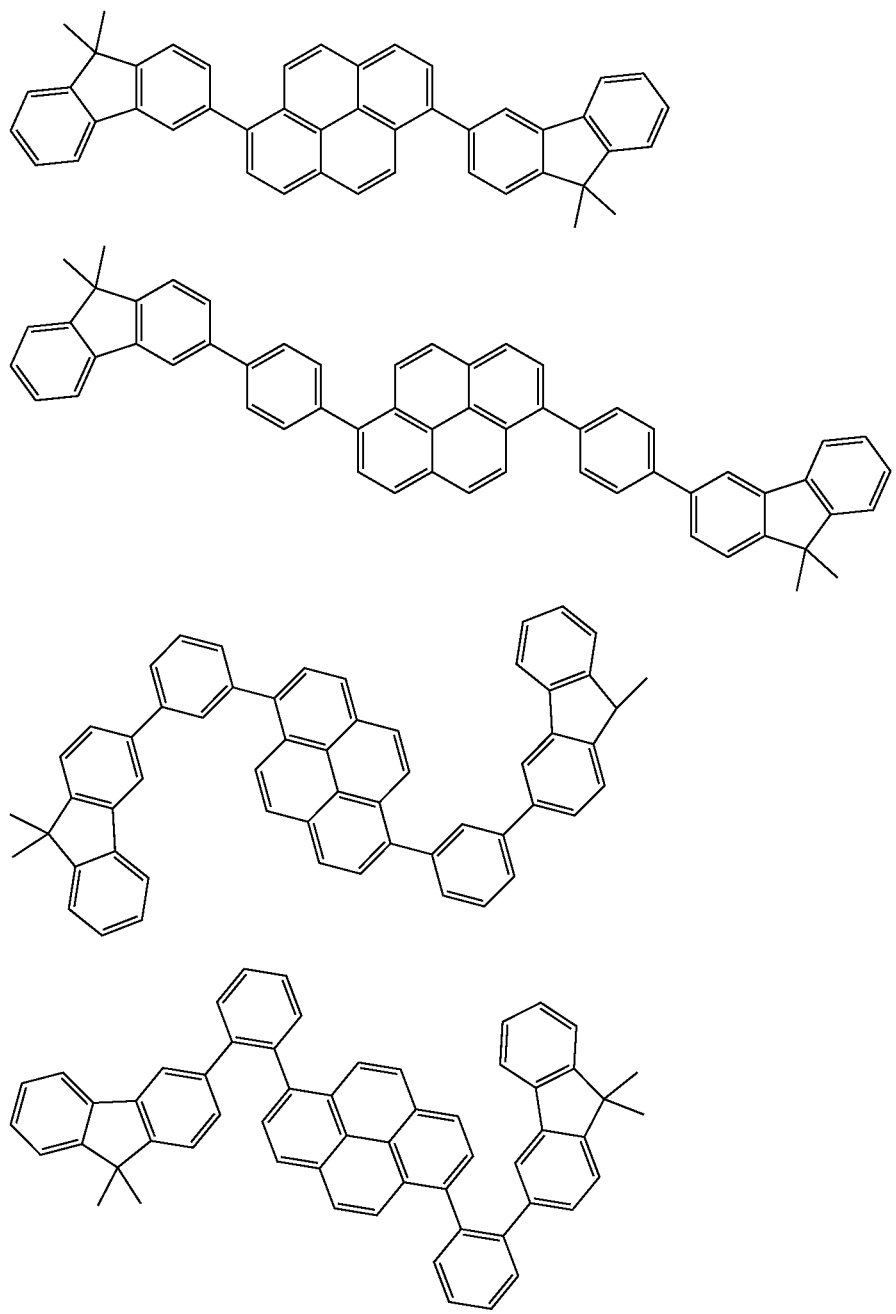

-continued
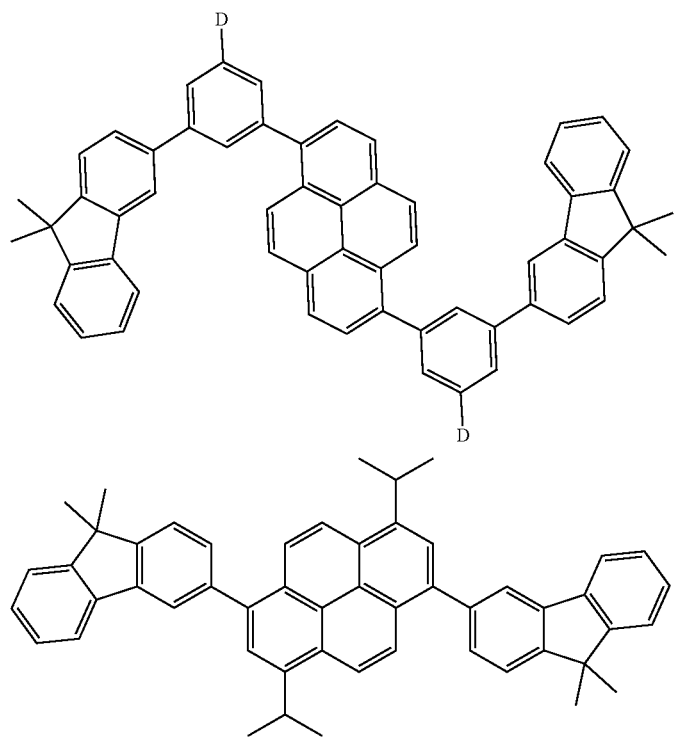
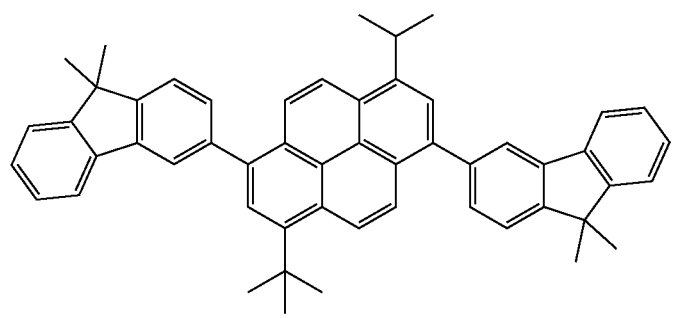
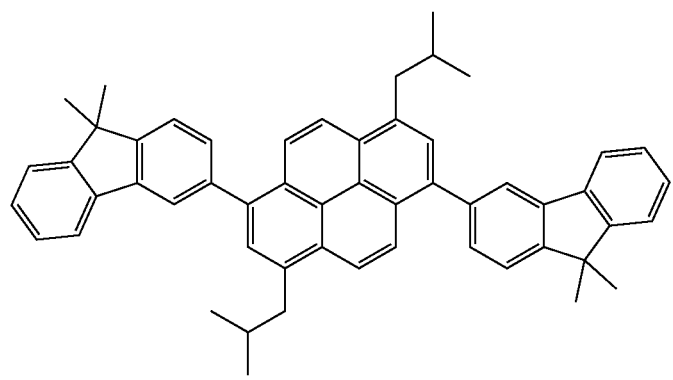

-continued
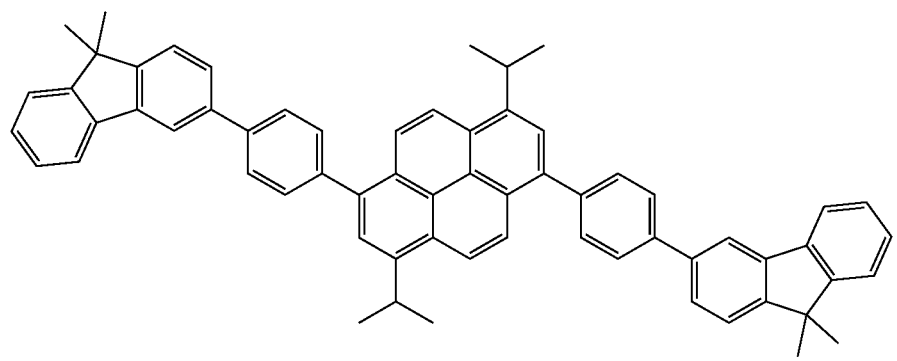
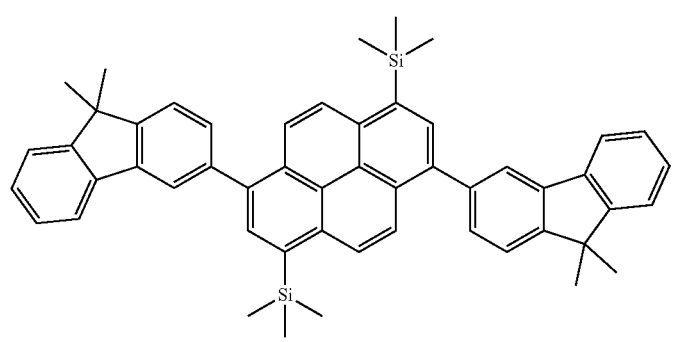
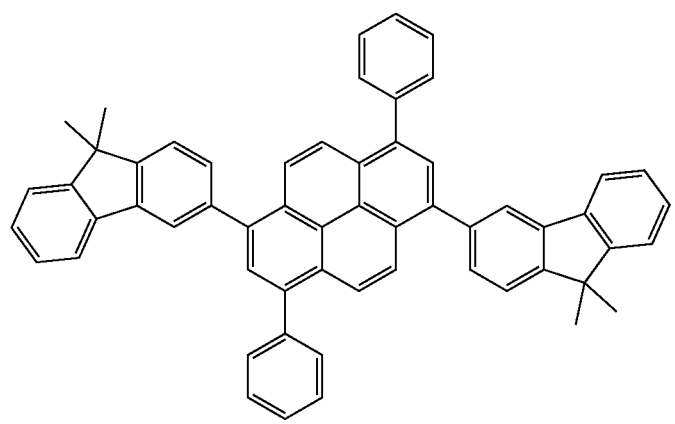
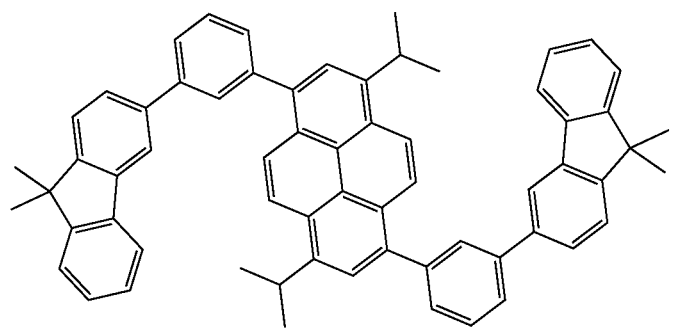

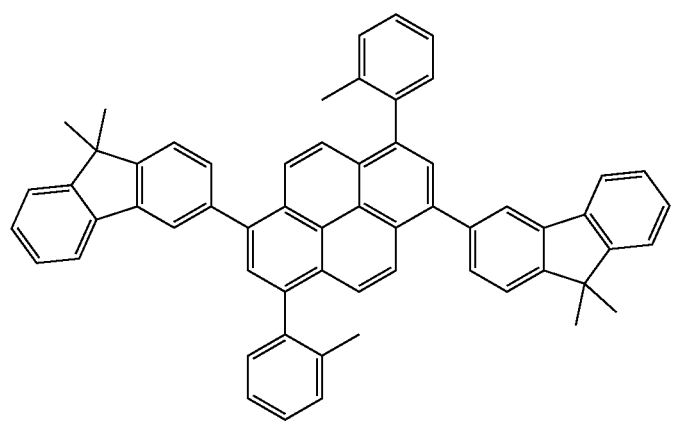
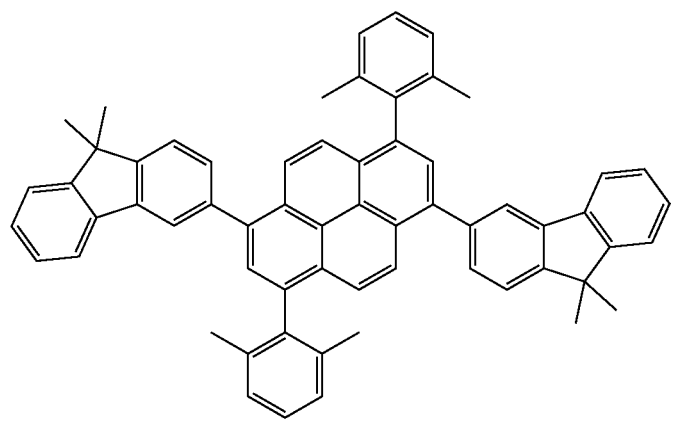
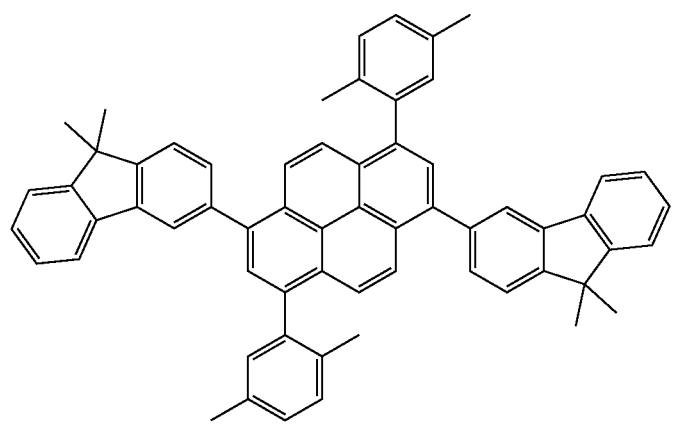

-continued
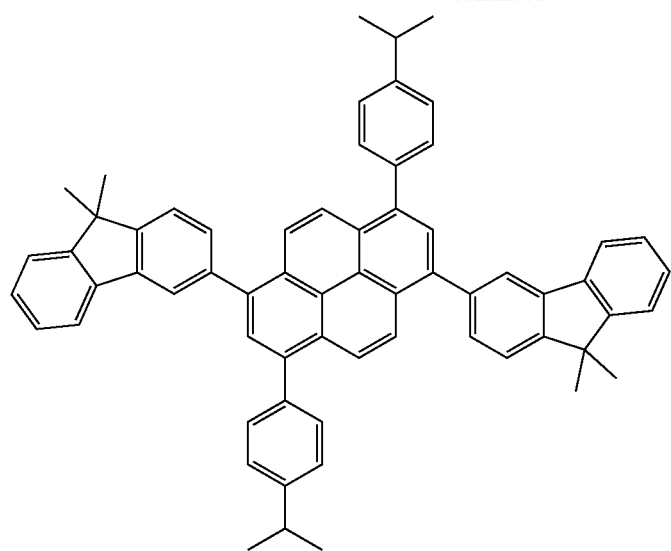
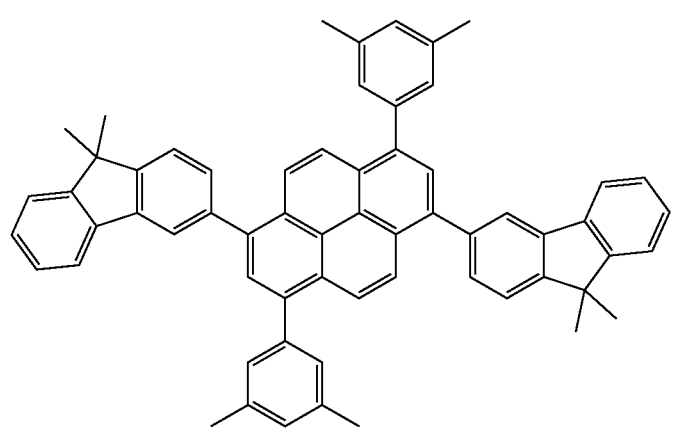
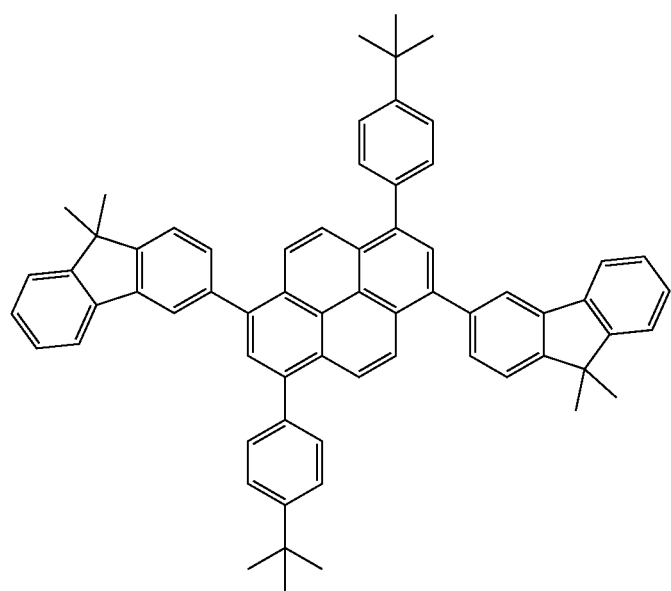

-continued
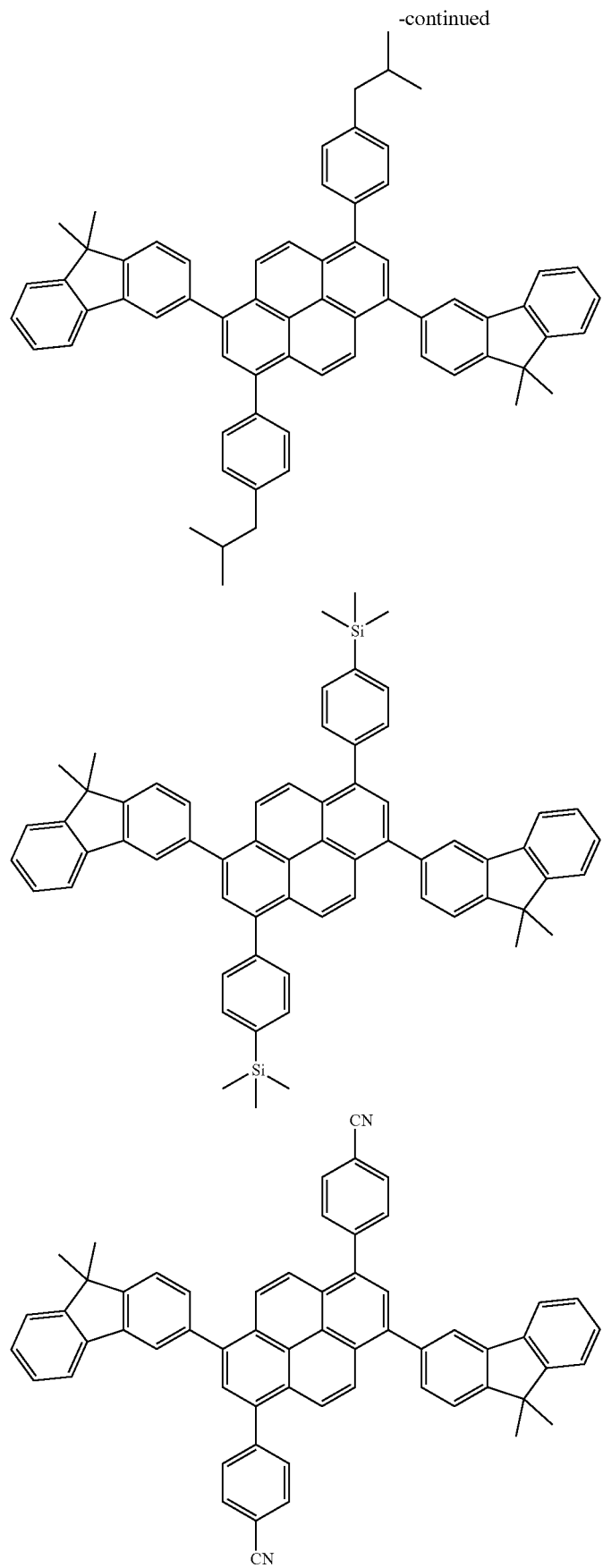

-continued
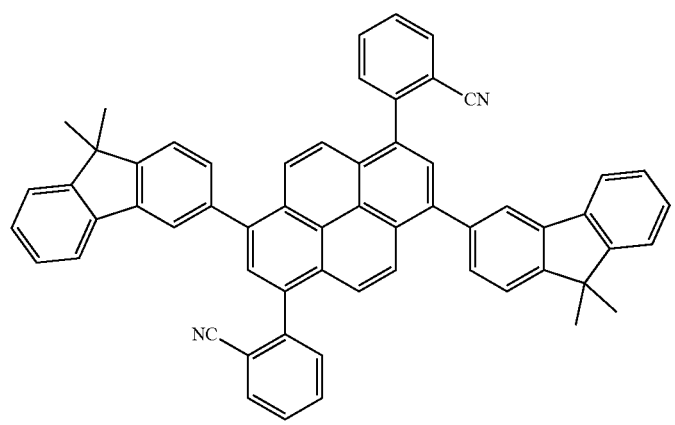
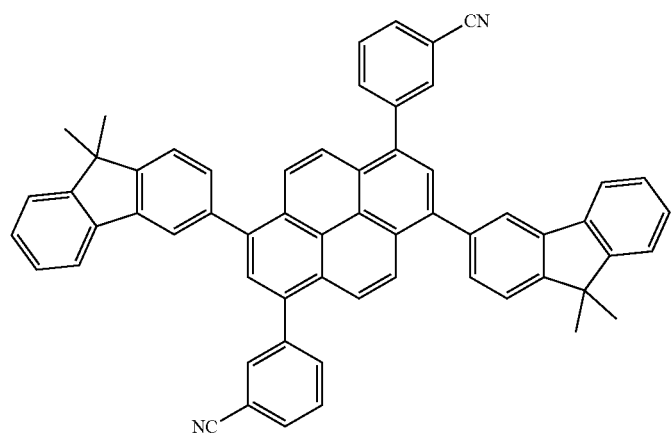
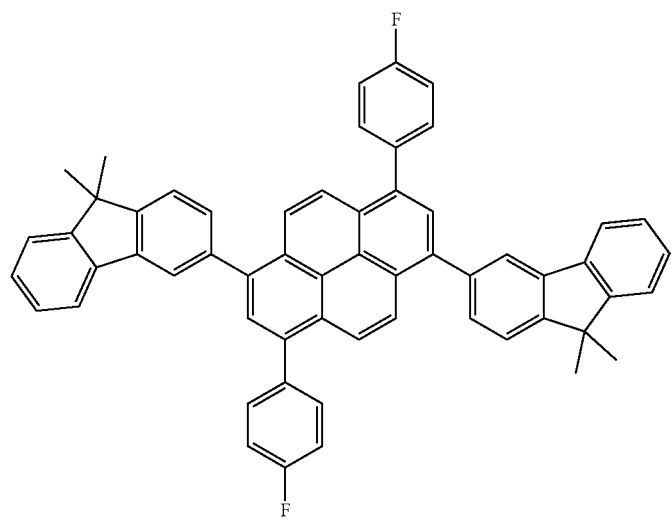

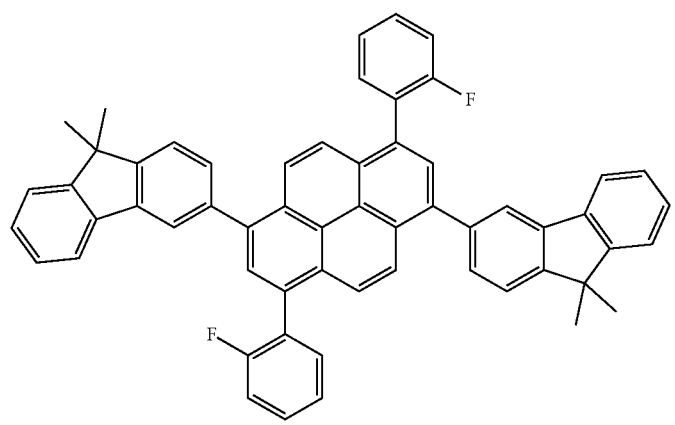
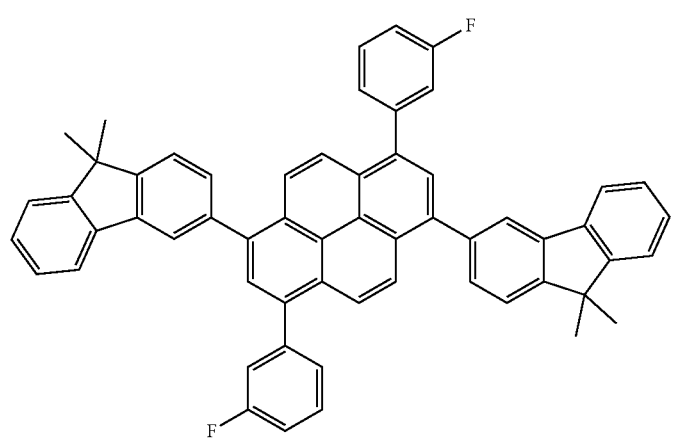
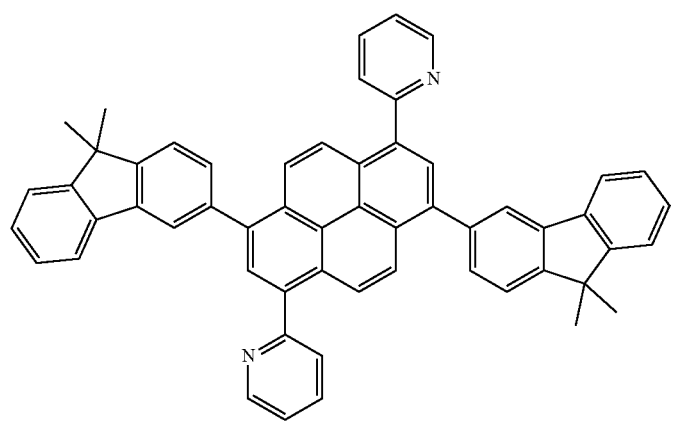

-continued
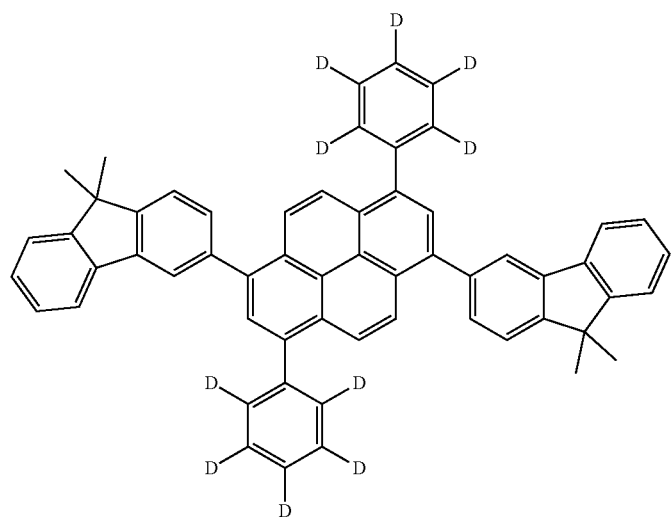
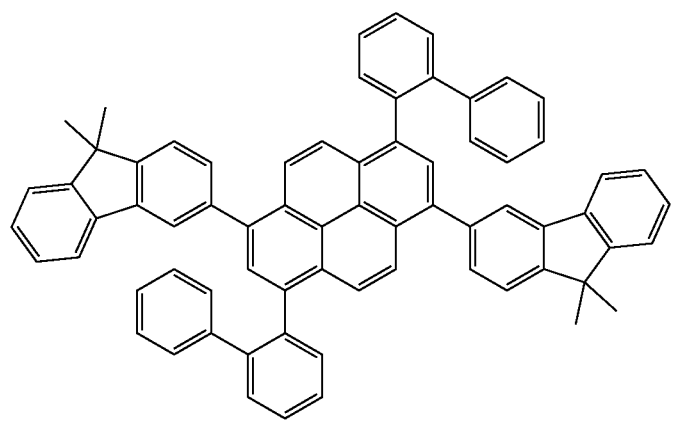
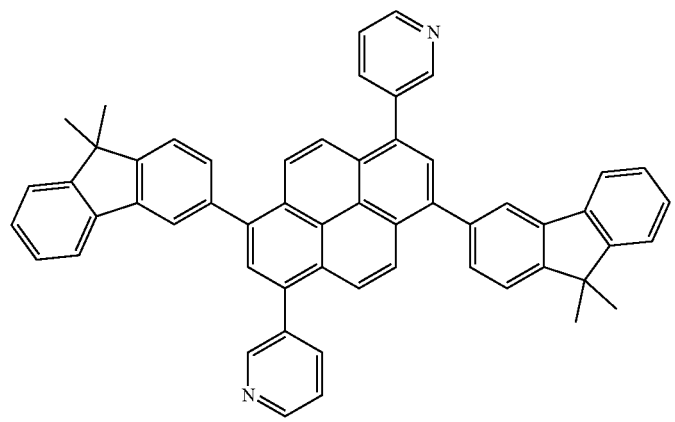

-continued
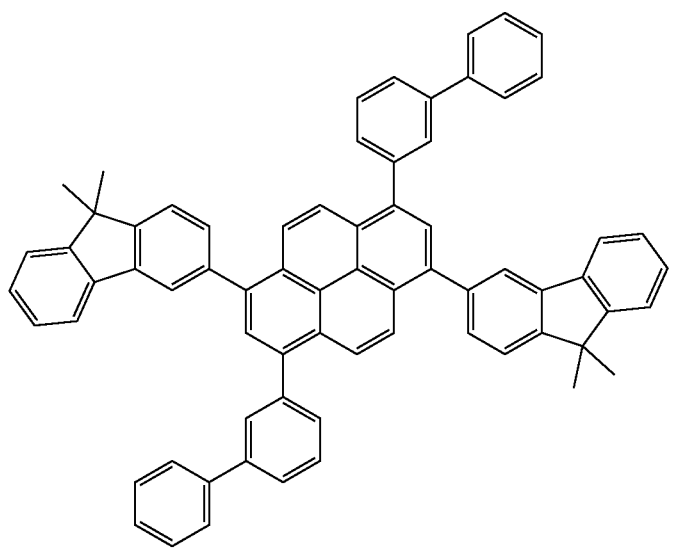
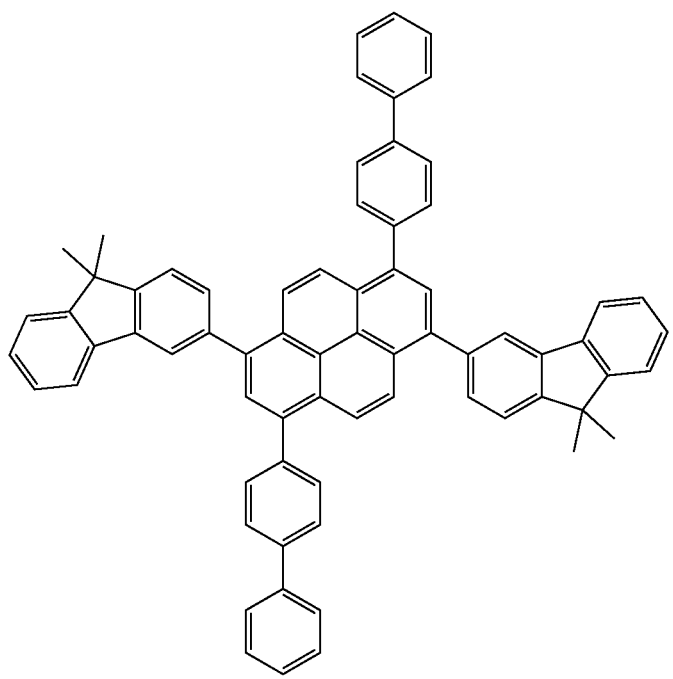

-continued
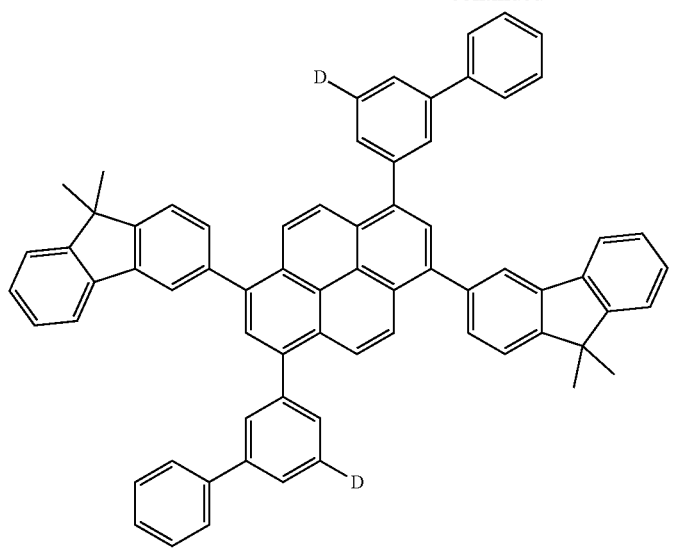
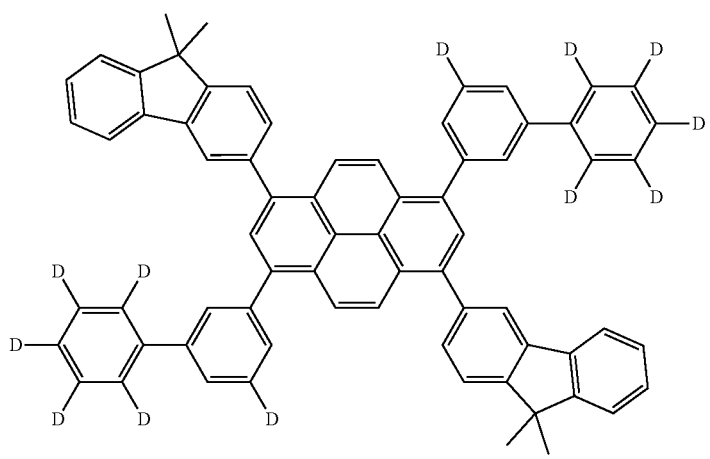
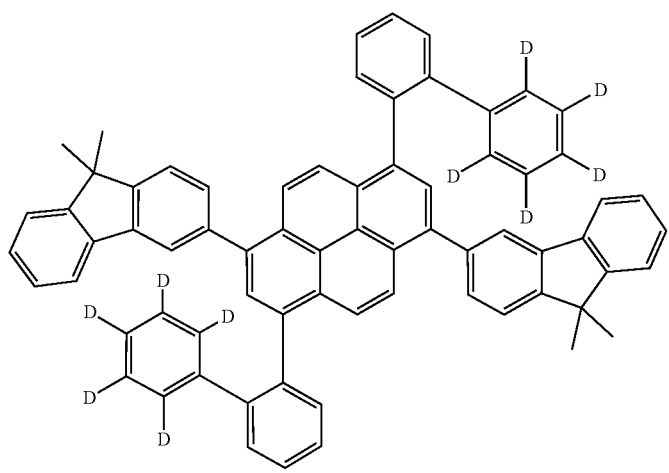

-continued
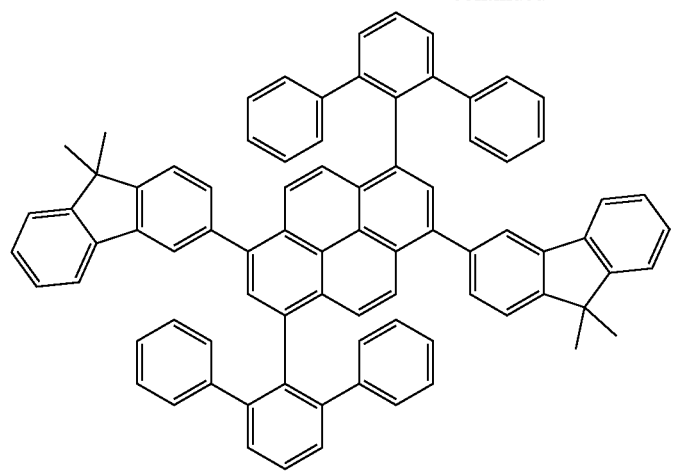
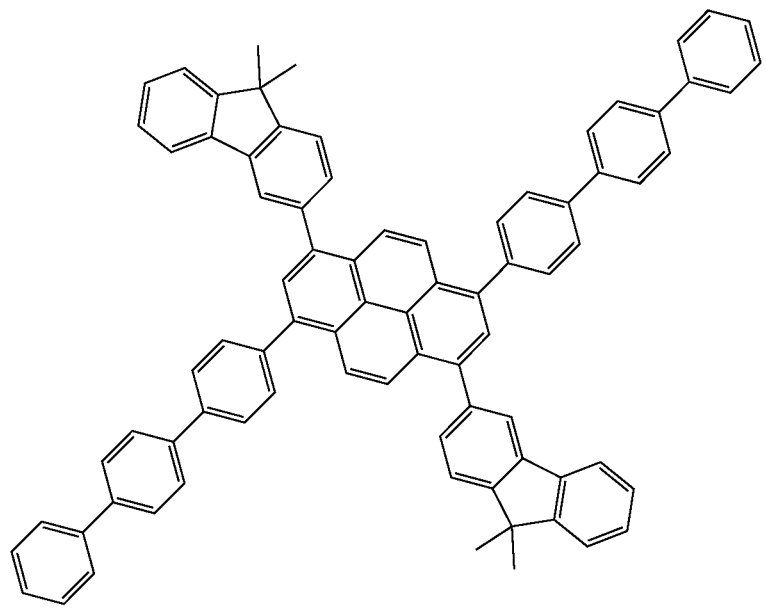
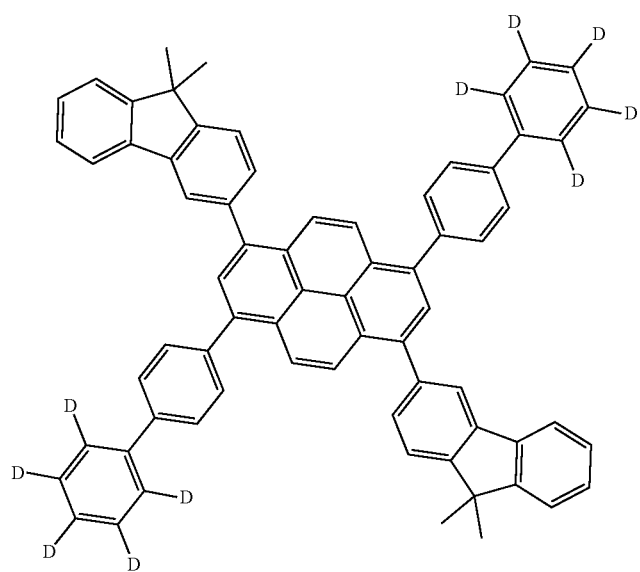

-continued
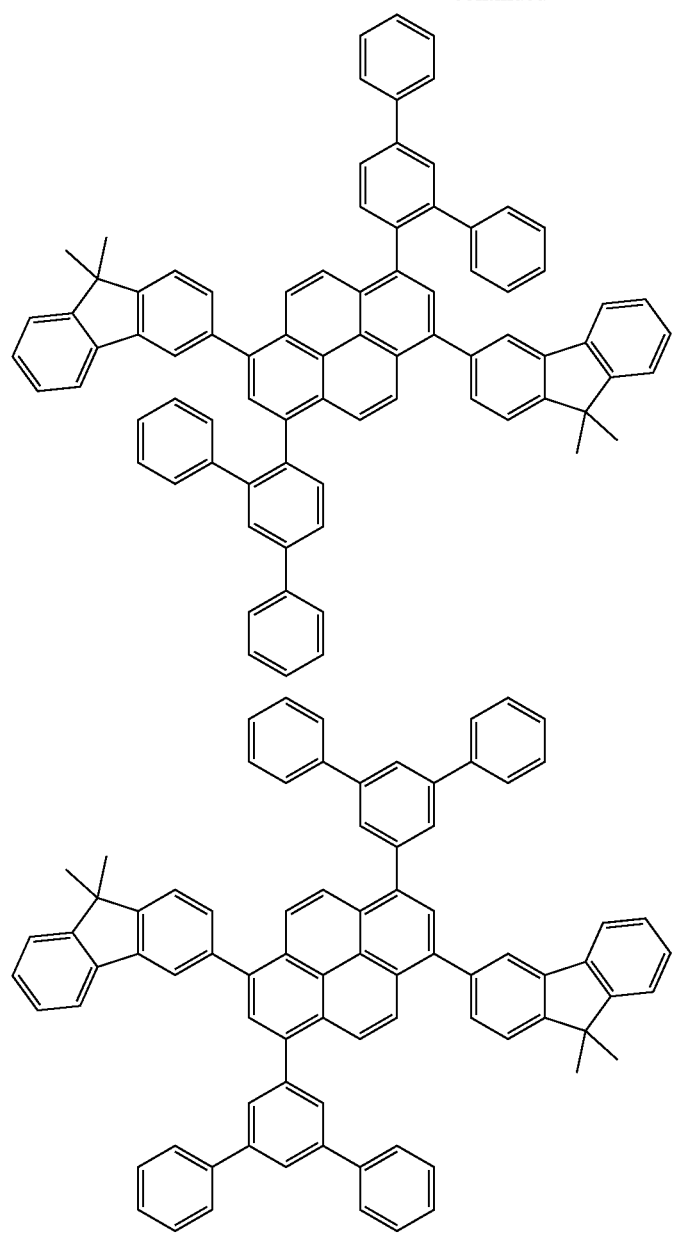
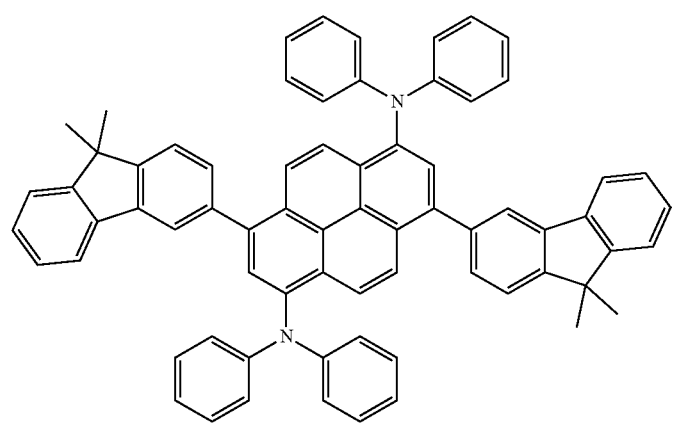

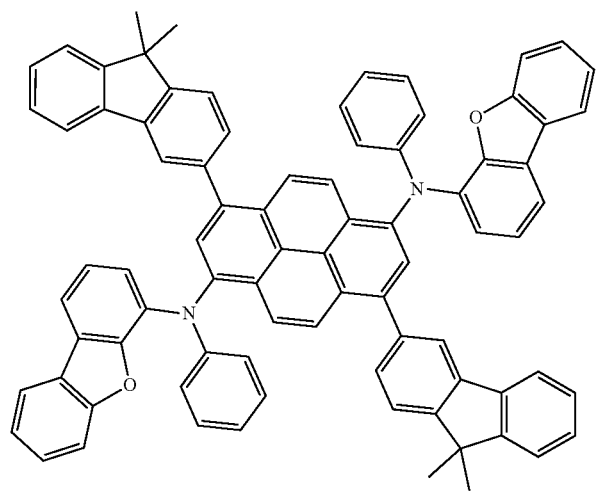
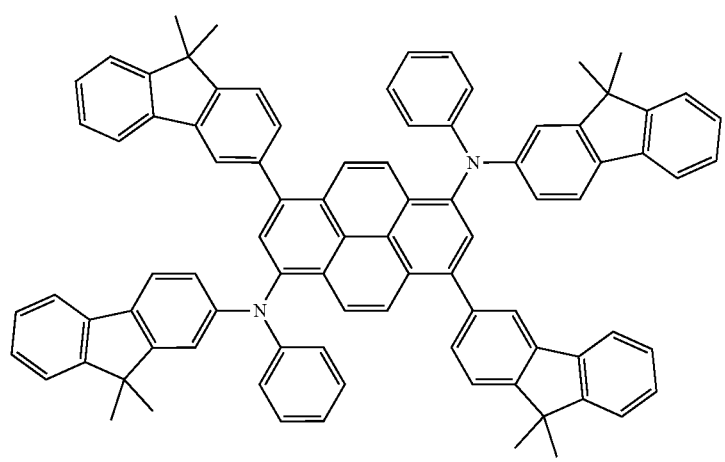
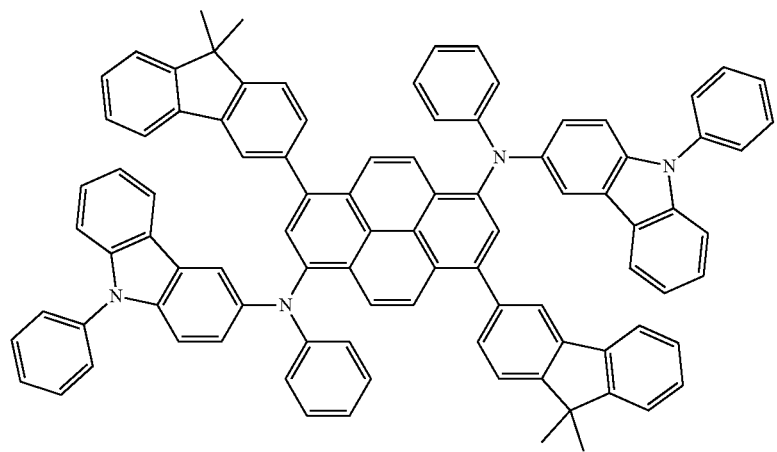

-continued
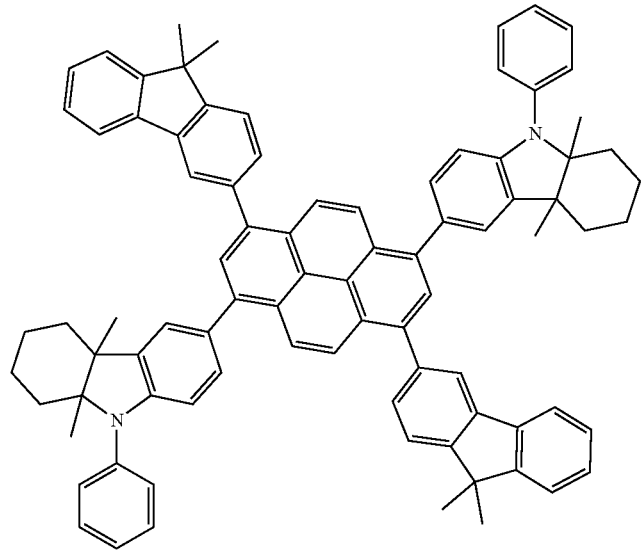
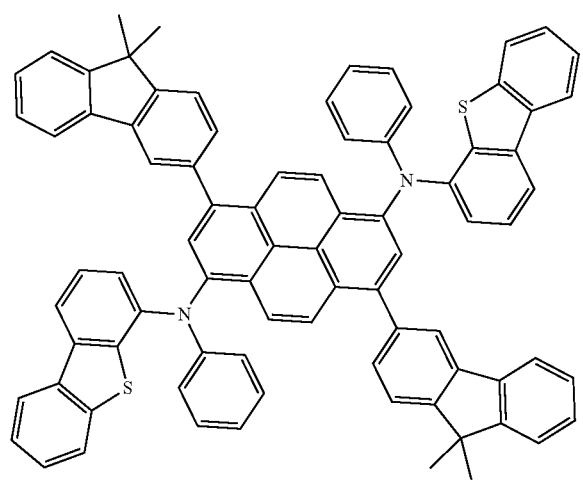
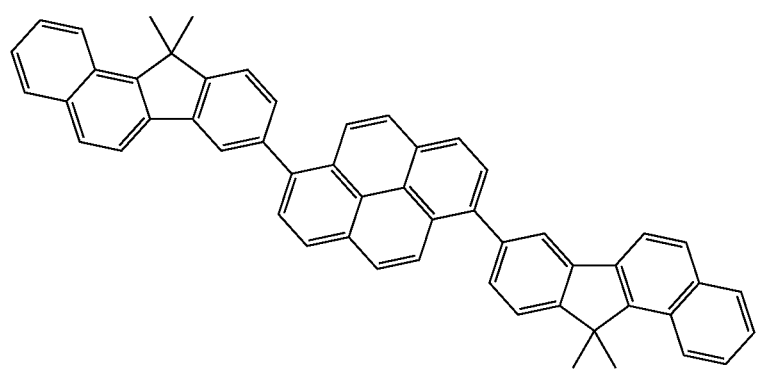

-continued
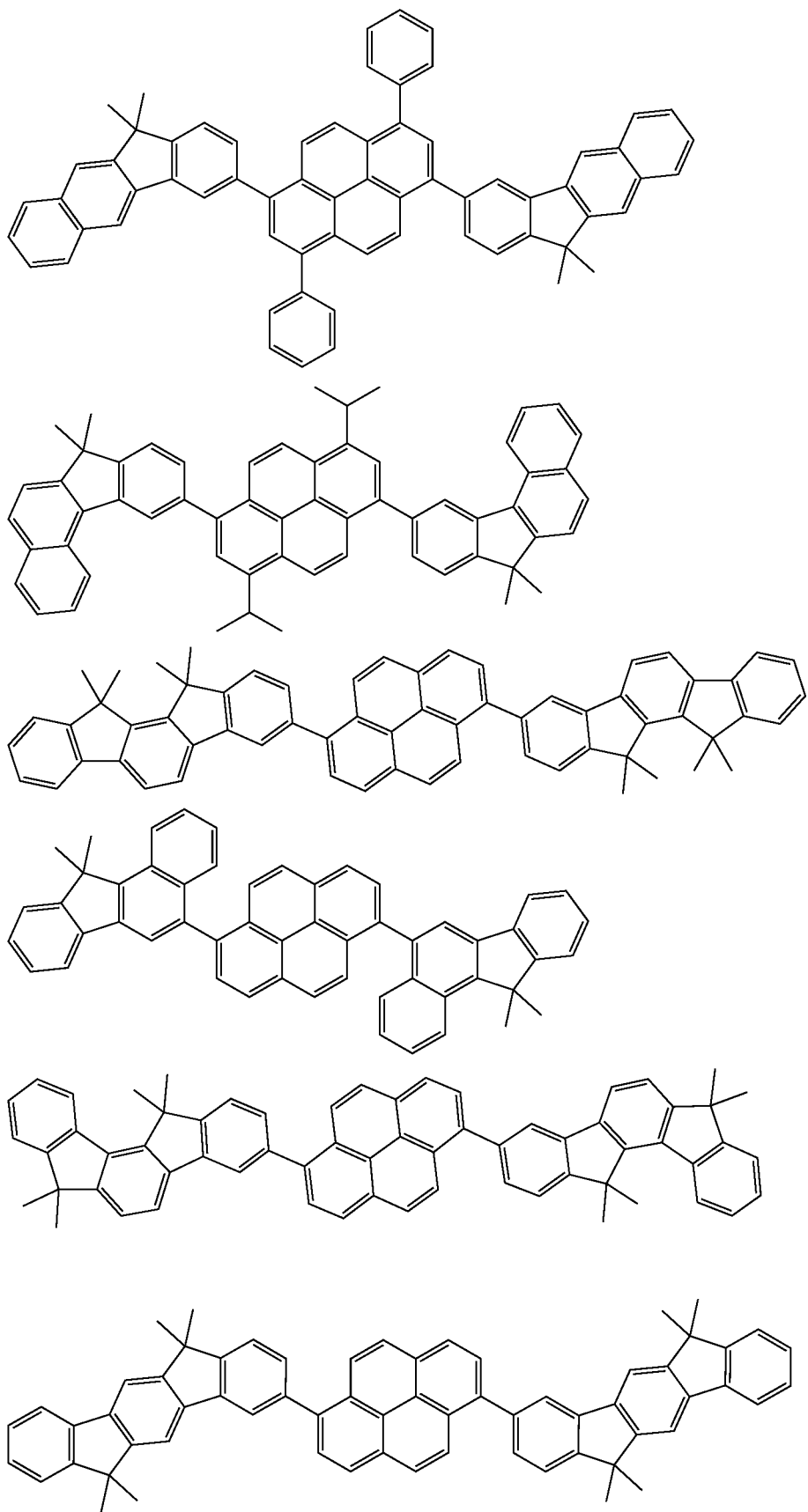

-continued
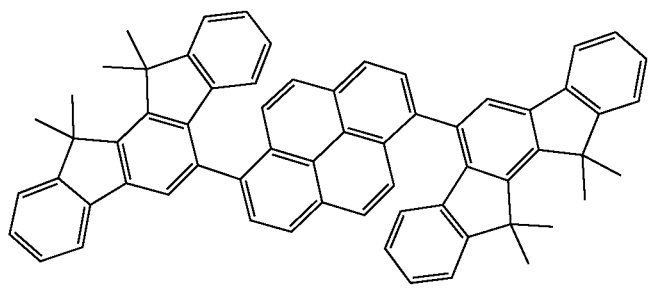
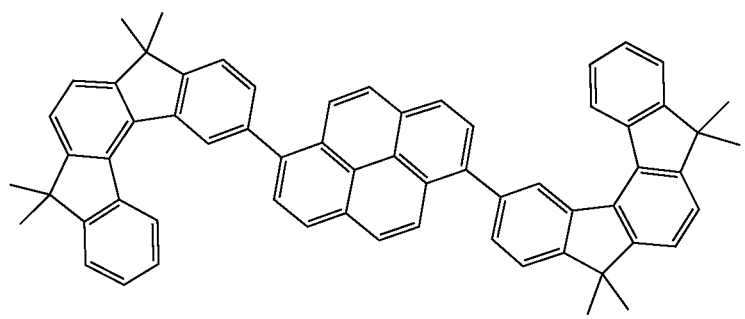
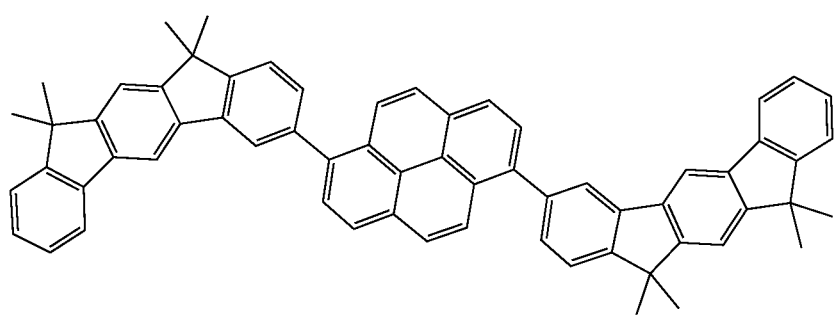
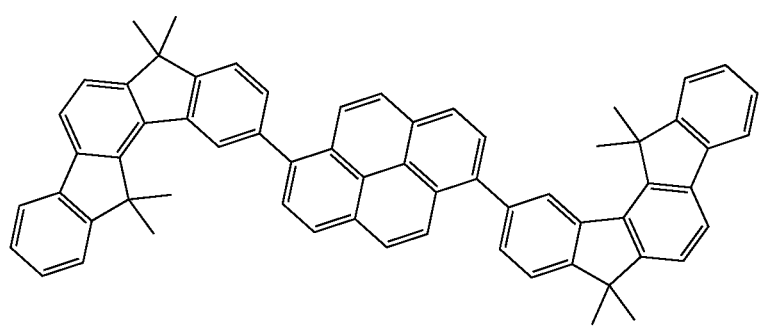
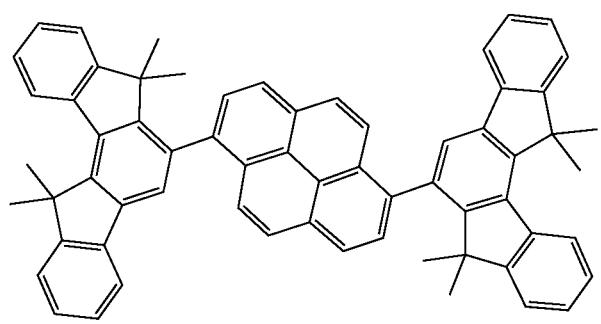

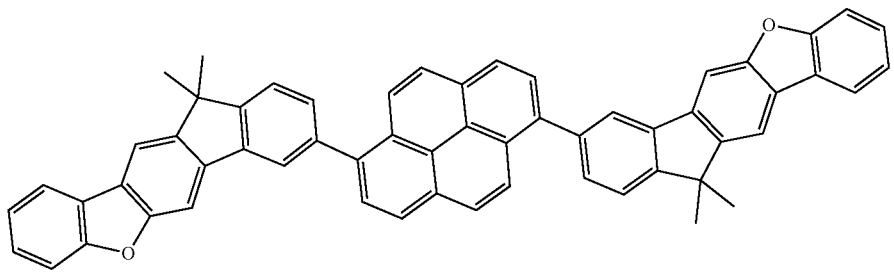
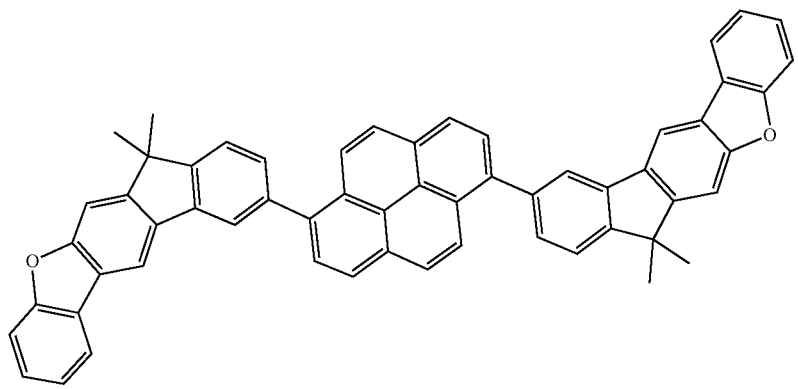
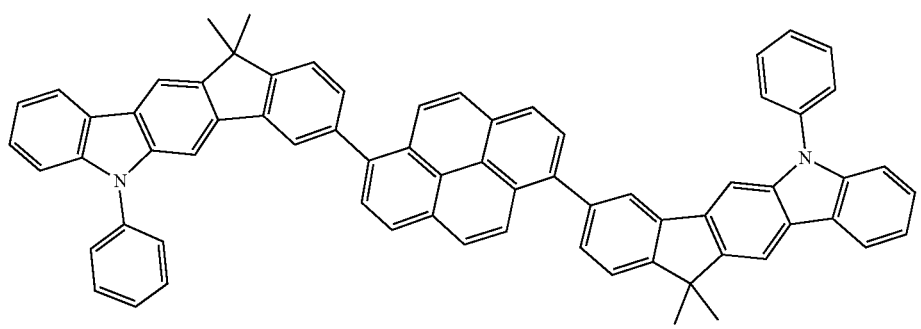
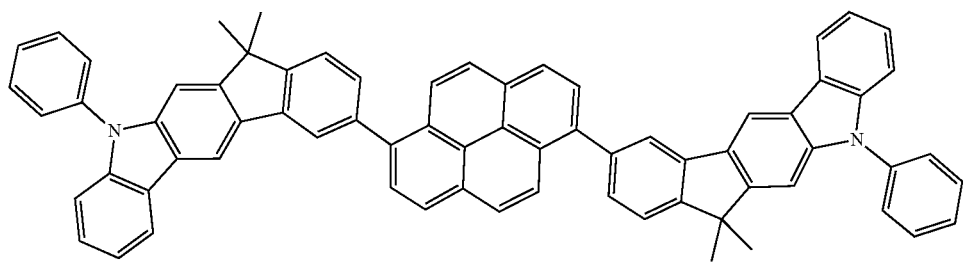
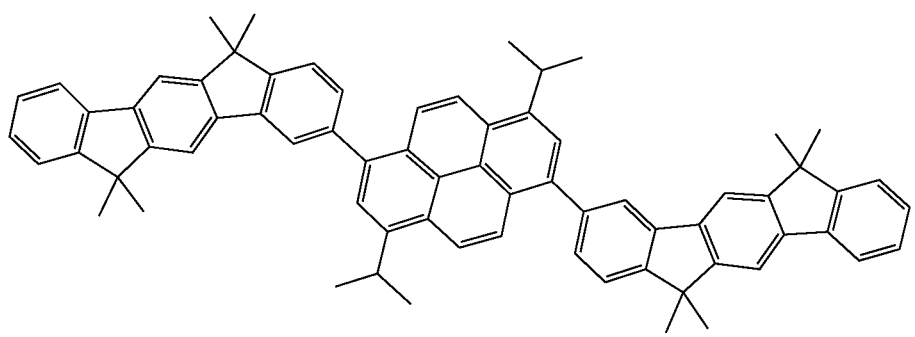

-continued
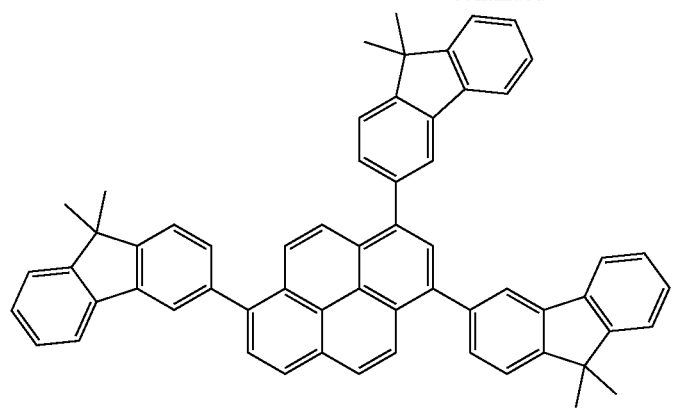
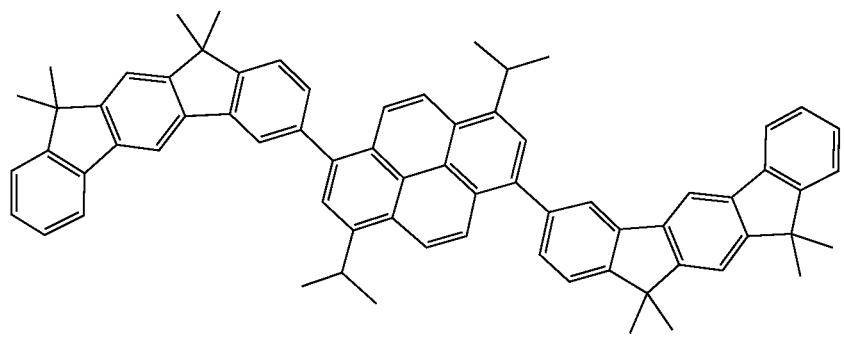
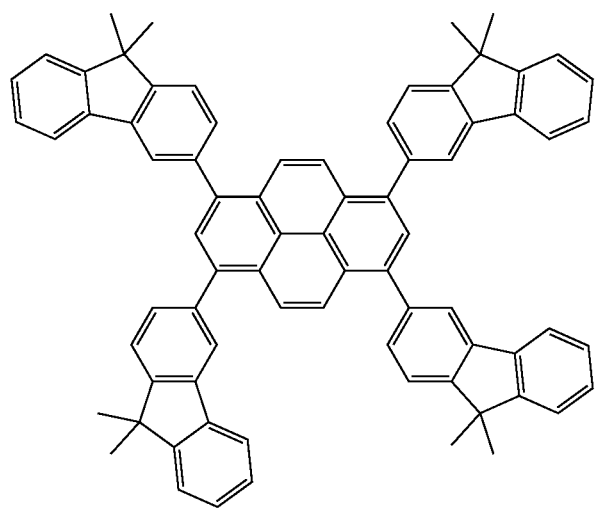
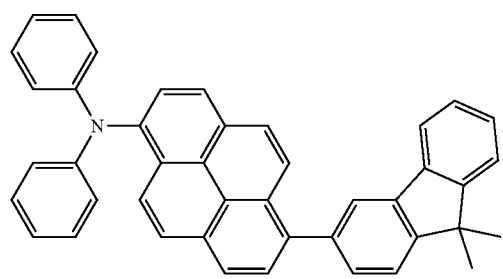

-continued
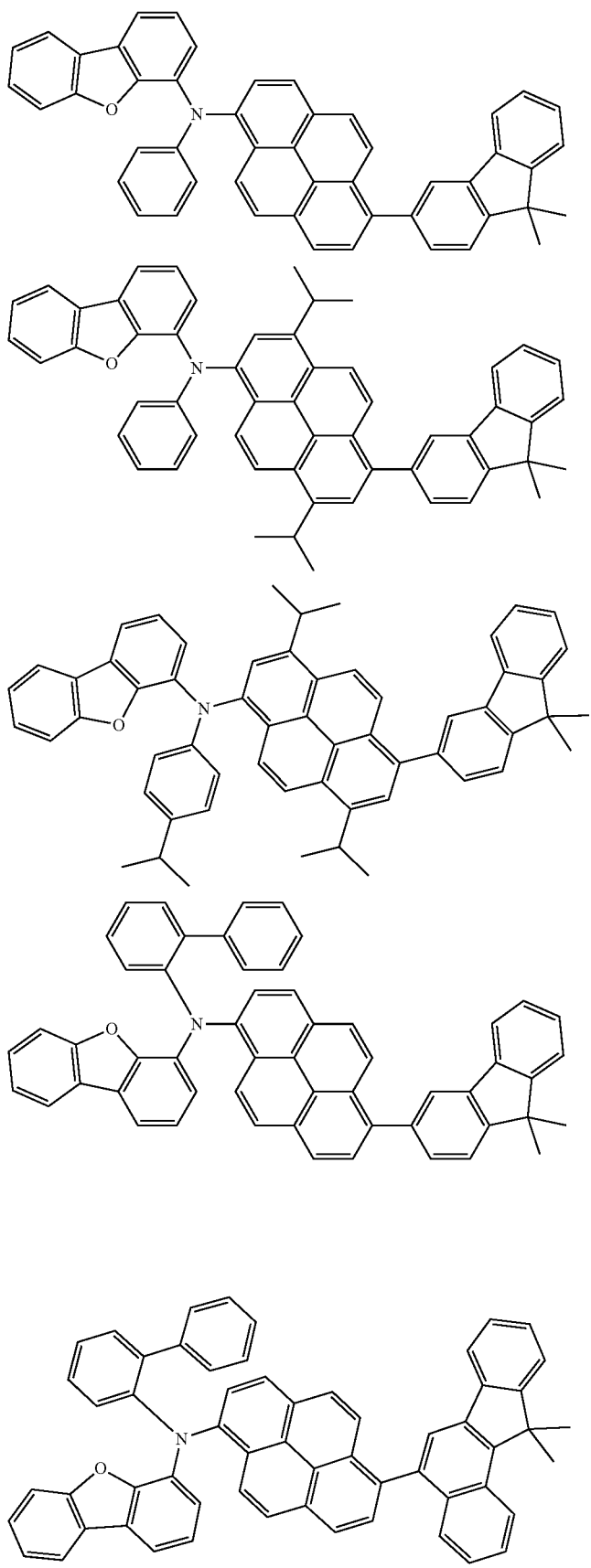

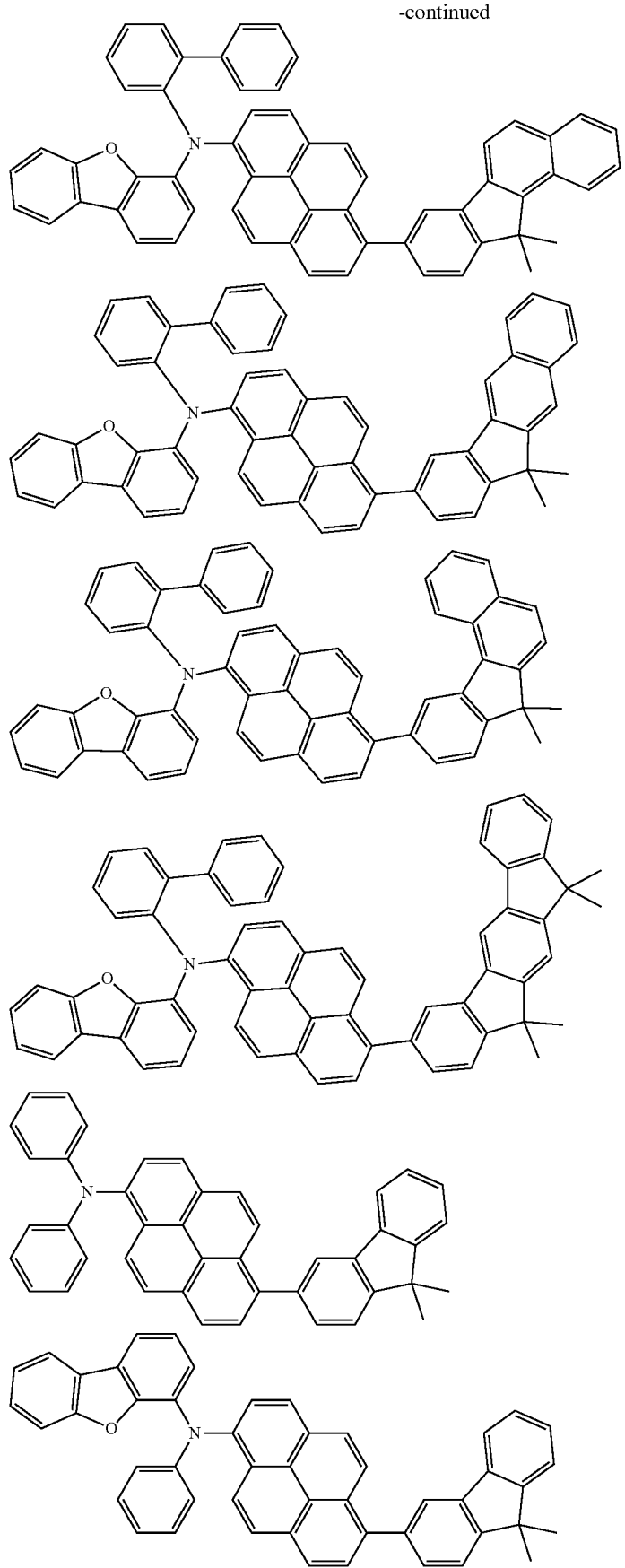

-continued
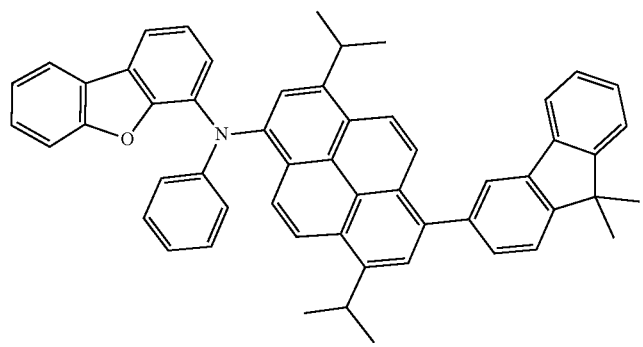
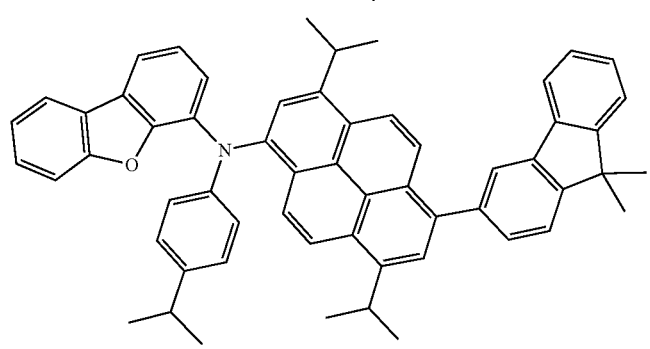
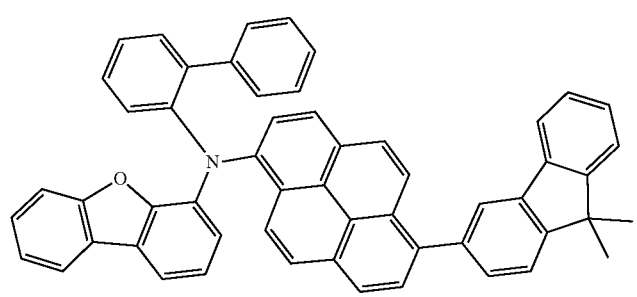
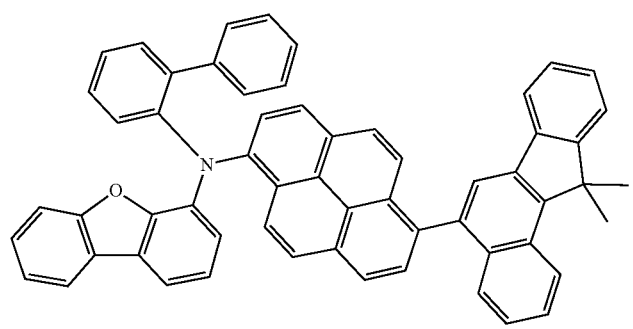
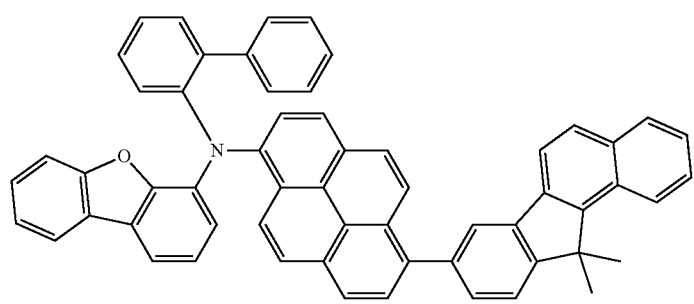

-continued

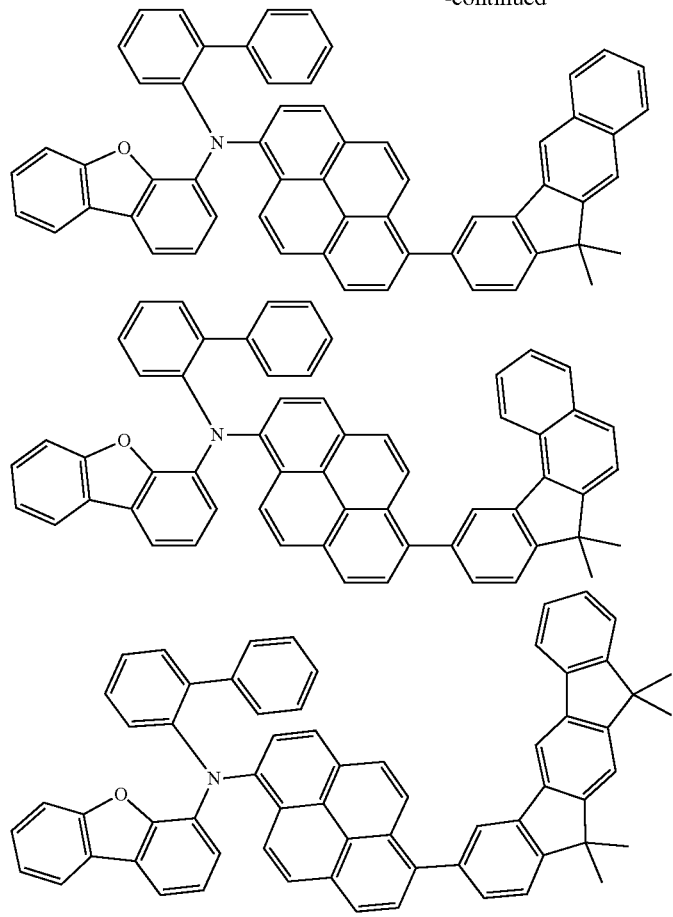

The present disclosure also relates to a method for synthesizing the fused ring compound, wherein the reaction is carried out using a raw material containing reactive groups. These active raw materials comprise at least one leaving group, for example, bromine, iodine, boric acid or borate ester. Appropriate reactions for forming C-C linkage are well known to those skilled in the art and described in the literatures, and particularly appropriate and preferred coupling reactions are SUZUKI, STILLE and HECK coupling reactions.

The present disclosure also further relates to a polymer, and the polymer has a repeating unit comprising a group formed by the fused ring compounds losing at least one hydrogen atom or deuterium atom. In certain embodiments, the polymer is a non-conjugated polymer, wherein the group formed by the fused ring compound losing at least one hydrogen atom or one deuterium atom is on a side chain of the polymer. In another preferred embodiment, the polymer is a conjugated polymer.

The present disclosure also provides a mixture comprising the fused ring compound and a second organic functional material, or comprising the polymer and a second organic functional material. The second organic functional material may be at least one selected from the group consisting of a hole (also called electron hole) injection or transport material (HIM/HTM), a hole blocking material (HBM), electron injection or transport material (EIM/ETM), an electron blocking material (EBM), an organic matrix material (Host), a singlet emitter (fluorescent emitter), a triplet emitter (phosphorescent emitter), a thermally activated delayed fluorescent material (TADF material) and an organic dye, and various organic functional materials are described in detail, for example, in WO2010135519A1, US20090134784A1, and WO 2011110277A1, the entire disclosure of which is incorporated by reference herein.

In some embodiment, the second organic functional material is a fluorescent host material (or a singlet matrix material). In this embodiment, the fused ring compound can be used as a guest, and the fused ring compound of the mixture is present at a weight percentage ≤15 wt %, further, the fused ring compound of the mixture is present at a weight percentage ≤12 wt %, still further, the fused ring compound of the mixture is present at a weight percentage ≤9 wt %, still further, the fused ring compound of the mixture is present at a weight percentage ≤8 wt %, even further, the fused ring compound of the mixture is present at a weight percentage ≤7 wt %.

In some embodiments, the second organic functional material is a fluorescent emitter (or a singlet emitter) and fluorescent host material. In this embodiment, the fused ring compound can be used as an auxiliary light-emitting material and a weight ratio of the fused ring compound to the fluorescent emitter ranges from 1:2 to 2:1.

In certain embodiments, the second functional material is a TADF material.

In other embodiments, the second organic functional material is a HTM material.

The HTM, singlet matrix materials, singlet emitters and TADF materials are described in more detail below, but are not limited thereto.

1, HIM/HTM/EBM

Suitable organic HIM/HTM materials may be selected from compounds having the following structural units: phthalocyanine, porphyrin, amine, aromatic amine, biphenyl triarylamine, thiophene, fused thiophene such as dithienothiophene and thiophthene, pyrrole, aniline, carbazole, indolocarbazole and derivatives thereof. In addition, suitable HIM also comprises self-assembled monomer such as a compound containing phosphonic acid and sliane derivatives, a metal complex and a cross-linking compound. The electron blocking layer (EBL) is used to block electrons from adjacent functional layers, particularly light emitting layers. In contrast to a light-emitting device without a blocking layer, the presence of EBL usually results in an increase in luminous efficiency. The electron blocking material (EBM) of the electron blocking layer (EBL) requires a higher LUMO than that of the adjacent functional layer, such as the light emitting layer. In a preferred embodiment, the HBM has a greater energy level of excited state than that of the adjacent light emitting layer, such as a singlet or triplet level, depending on the emitter. Meanwhile, the EBM has a hole transport function. HIM/HTM materials, which typically have high LUMO levels, can be used as EBM.

Examples of cyclic aromatic amine derivatives which can be applied as the HIM, HTM or EBM include (but are not limited to) the following general structures:

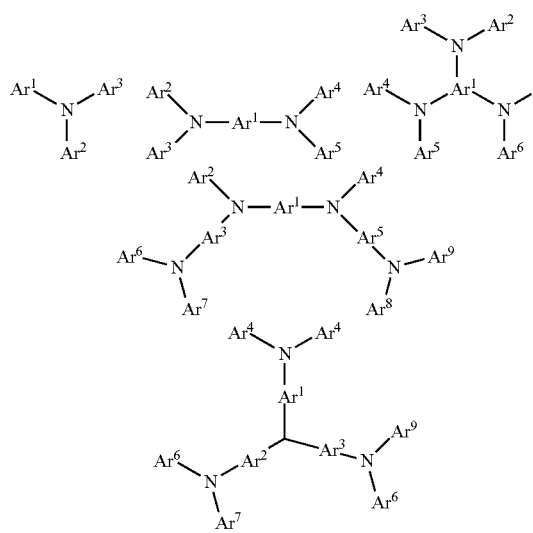

Each of $Ar^1$ to $Ar^9$ may be independently selected from the group consisting of cyclic aromatic hydrocarbon compound such as benzene, biphenyl, triphenyl, benzo, naphthalene, anthracene, phenalene, phenanthrene, fluorene, pyrene, chrysene, perylene, azulene; aromatic heterocycle compound such as dibenzothiophene, dibenzofuran, furan, thiophene, benzofuran, benzothiophene, carbazole, pyrazole, imidazole, triazole, isoxazole, thiazole, oxadiazole, oxytriazole, dioxazole, thiadiazole, pyridine, pyridazine, pyrimidine, pyrazine, triazine, oxazine, oxathiazine, oxadiazine, indole, benzimidazole, indazole, indolizine, benzoxazole, benzisoxazole, benzothiazole, quinoline, isoquinoline, cinnoline, quinazoline, quinoxaline, naphthalene, phthalein, pteridine, xanthene, acridine, phenazine, phenothiazine, phenoxazine, dibenzoselenophene, benzoselenophene, benzofuropyridine, indolocarbazole, pyridylindole, pyrrolodipyridine, furodipyridine, benzothieopyridine, thienopyridine, benzoselenophenepyridine and selenophenodipyridine; and groups containing 2 to 10 ring structures, which may be the same or different types of cyclic aromatic hydrocarbyl groups or aromatic heterocyclic groups, and linked to each other directly or through at least one of the following groups: such as oxygen atom, nitrogen atom, sulfur atom, silicon atom, phosphorus atom, boron atom, chain structure unit, and aliphatic ring group. Wherein, each Ar may be further substituted, the substituent may be selected from the group consisting of hydrogen, alkyl, alkoxy, amino, alkene, alkyne, aralkyl, heteroalkyl, aryl and heteroaryl.

In one aspect, $Ar^1$ to $Ar^9$ can be independently selected from the group consisting of:

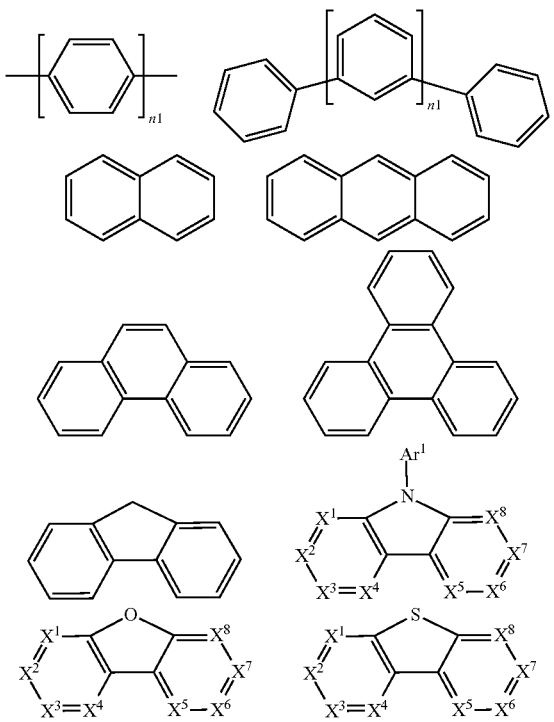

n1 is an integer of 1 to 20; $X^1$ to $X^8$ are CH or N; $Ar^1$ is as defined above.

Additional examples of cyclic aromatic amine derivative compounds may be found in U.S. Pat. Nos. 3,567,450, 4,720,432, 5,061,569, 3,615,404 and 5,061,569.

Examples of metal complexes that can be used as HTM or HIM include, but not limited to, the following general structures:

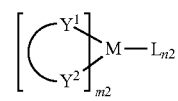

M is a metal, having an atomic weight greater than 40; $(Y^1-Y^2)$ is a bidentate ligand, wherein $Y^1$ and $Y^2$ are independently selected from the group consisting of C, N, O, P, and S; L is an auxiliary ligand; m2 is an integer from 1 to the maximum coordination number of the metal; m2+n2 is the maximum coordination number of the metal.

In one embodiment, $(Y^1\text{-}Y^2)$ may be a 2-phenylpyridine derivative.

In another embodiment, $(Y^1\text{-}Y^2)$ may be a carbene ligand.

In another embodiment, M may be selected from the group consisting of Ir, Pt, Os, and Zn.

In another aspect, the HOMO of the metal complex is greater than −5.5 eV (relative to the vacuum level).

Suitable examples that can be used as HIM/HTM compounds are listed in the table below:

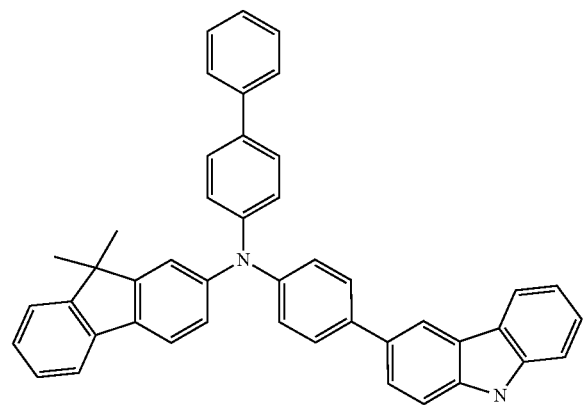

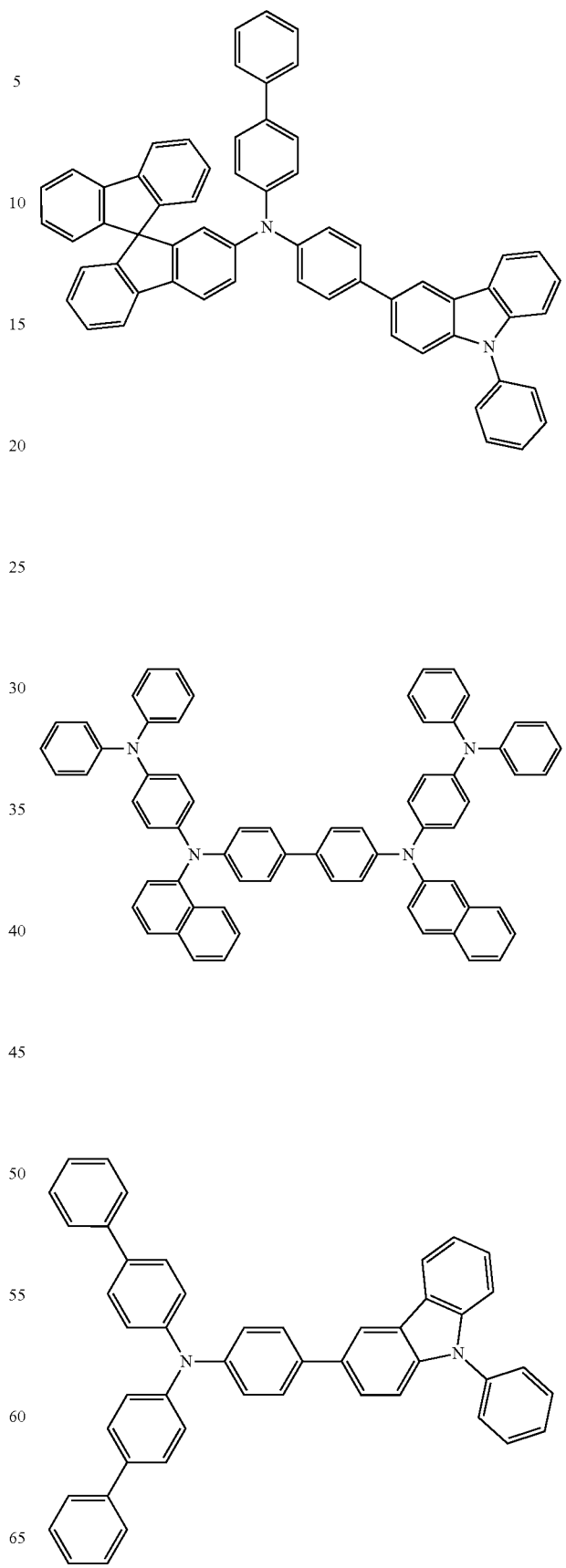

-continued

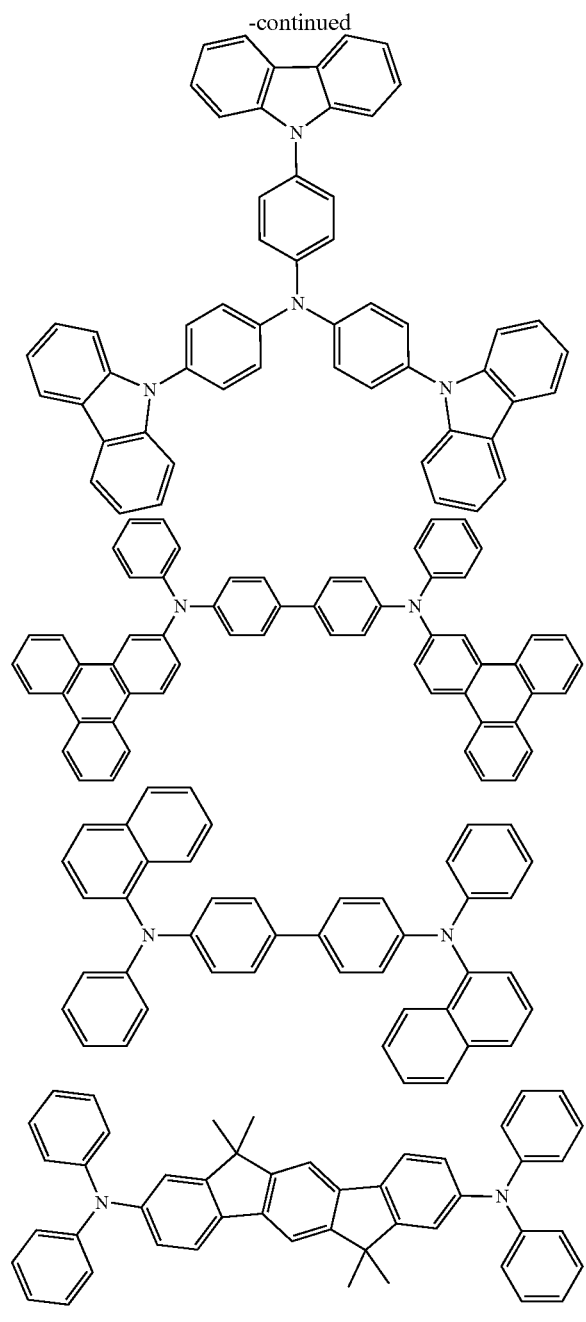

2. Singlet Host Material:

Examples of singlet host material are not particularly limited and any organic compound may be used as the host as long as its singlet state energy is greater than that of the emitter, especially the singlet emitter or fluorescent emitter.

Non-limiting examples of organic compounds used as singlet host materials may be selected from the group consisting of: compounds containing cyclic aromatic hydrocarbon groups, such as benzene, biphenyl, triphenyl, benzo, naphthalene, anthracene, phenalene, phenanthrene, fluorene, pyrene, chrysene, perylene, azulene; aromatic heterocyclic compounds, such as triphenylamine, dibenzothiophene, dibenzofuran, dibenzoselenophen, furan, thiophene, benzofuran, benzothiophene, benzoselenophene, carbazole, indolocarbazole, indolopyridine, pyrrolodipyridine, pyrazole, imidazole, triazole, isoxazole, thiazole, oxadiazole, oxatri-azole, dioxazole, thiadiazole, pyridine, pyridazine, pyrimidine, pyrazine, triazine, oxazine, oxathiazin, oxadiazine, indole, benzimidazole, indoxazine, bisbenzoxazole, isoxazole, benzothiazole, quinoline, isoquinoline, cinnoline, quinazoline, quinoxaline, naphthalene, phthalein, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and groups comprising 2 to 10 membered ring structures, which may be the same or different types of aromatic cyclic or aromatic heterocyclic groups and are linked to each other directly or by at least one of the following groups, such as oxygen atom, nitrogen atom, sulfur atom, silicon atom, phosphorus atom, boron atom, chain structure unit, and aliphatic rings.

In one embodiment, the singlet host material may be selected from compounds comprising at least one of the following groups:

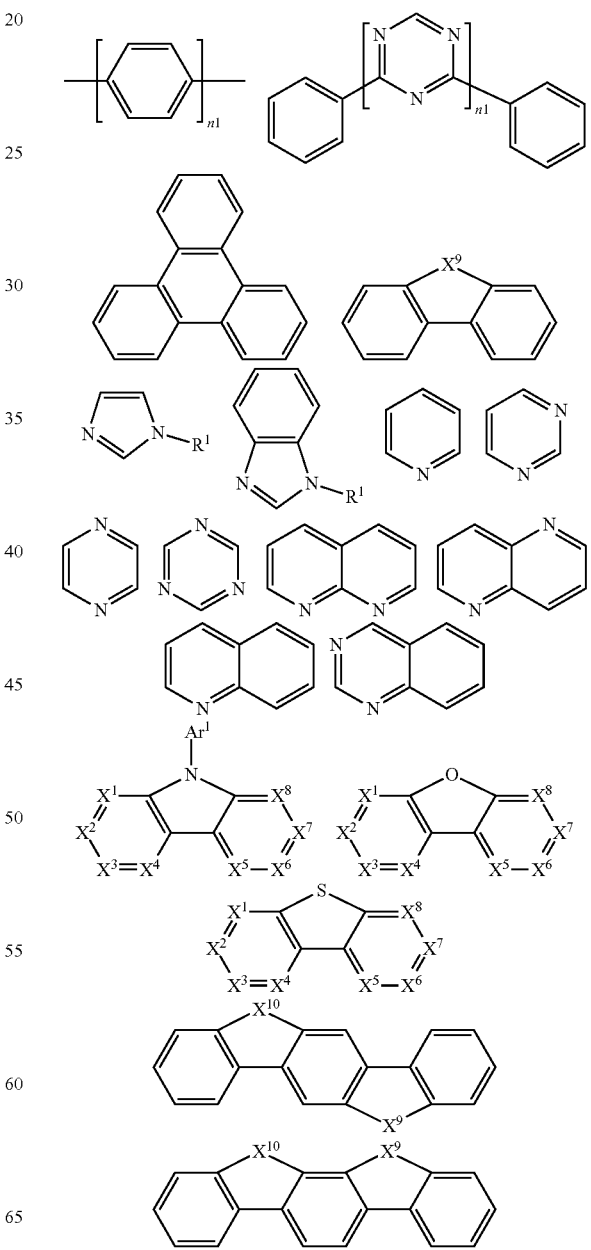

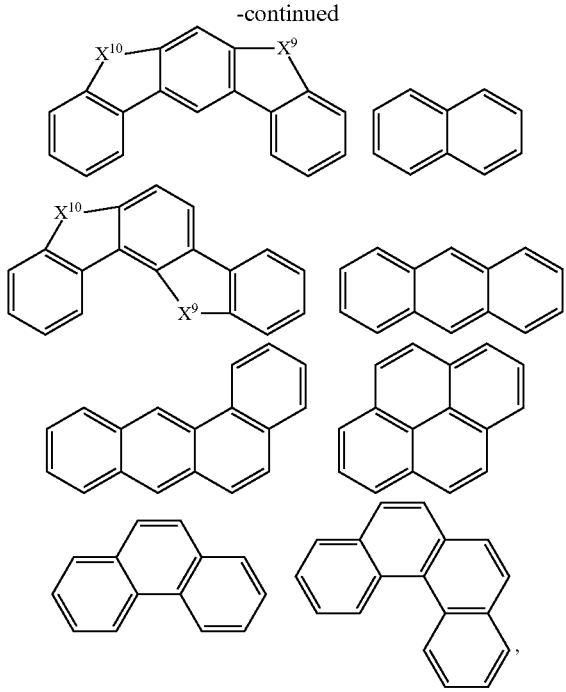

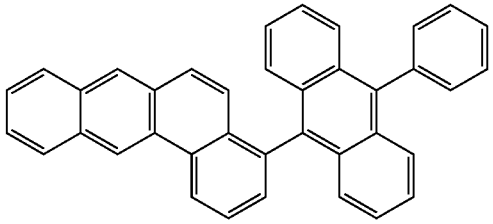

wherein, $R^1$ may be independently selected from the group consisting of hydrogen, alkyl, alkoxy, amino, alkene, alkyne, aralkyl, heteroalkyl, aryl and heteroaryl; $Ar^1$ is aryl or heteroaryl and has the same meaning as Ar defined in the HTM above; n1 is an integer from 0 to 20; $X^1$-$X^8$ is selected from CH or N; $X^9$ and $X^{10}$ are selected from $CR^1R^2$ or $NR^1$.

Some examples of anthracene-based singlet host material are listed in the table below:

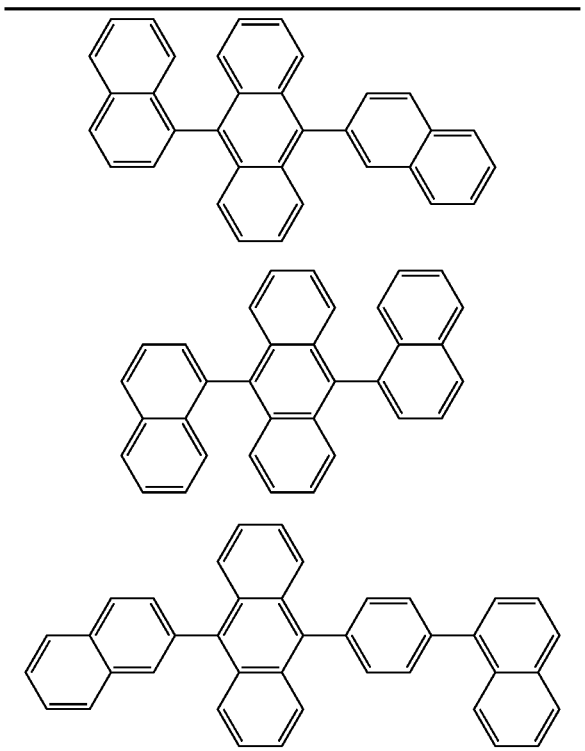

3. Singlet Emitter

The singlet emitter tends to have a longer conjugate π-electron system. To date, there have been many examples, such as, but not limited to, styrylamine and derivatives thereof disclosed in JP2913116B and WO2001021729A1, and indenofluorene and derivatives thereof disclosed in WO2008/006449 and WO2007/140847.

In some embodiments, the singlet emitter may be selected from the group consisting of monostyrylamines, distyrylamines, tristyrylamines, tetrastyrylamines, styrylphosphines, styryl ethers, and arylamines.

Mono styrylamine refers to a compound which comprises an unsubstituted or optionally substituted styryl group and at least one amine, most preferably an aromatic amine. Distyrylamine refers to a compound comprising two unsubstituted or optionally substituted styryl groups and at least one amine, most preferably an aromatic amine. Ternarystyrylamine refers to a compound which comprises three unsubstituted or optionally substituted styryl groups and at least one amine, most preferably an aromatic amine. Quaternarystyrylamine refers to a compound comprising four unsubstituted or optionally substituted styryl groups and at least one amine, most preferably an aromatic amine. Preferred styrene is stilbene, which may be further optionally substituted. The corresponding phosphines and ethers are defined similarly to amines. Aryl amine or aromatic amine refers to a compound comprising three unsubstituted or optionally substituted aromatic cyclic or heterocyclic systems directly attached to nitrogen. At least one of these aromatic cyclic or heterocyclic systems is preferably selected from fused ring systems and most preferably has at least 14 aromatic ring atoms. Among the preferred examples are aromatic anthramine, aromatic anthradiamine, aromatic pyrene amines, aromatic pyrene diamines, aromatic chrysene amines and aromatic chrysene diamine. Aromatic anthramine refers to a compound in which a diarylamino group is directly attached to anthracene, most preferably at position 9. Aromatic anthradiamine refers to a compound in which two diarylamino groups are directly attached to anthracene, most preferably at positions 9, 10. Aromatic pyrene amines, aromatic pyrene diamines, aromatic chrysene amines and aromatic chrysene diamine are similarly defined, wherein the diarylarylamino group is most preferably attached to position 1 or 1 and 6 of pyrene.

Examples of singlet emitter based on vinylamine and arylamine are also preferred examples which may be found in the following patent documents: WO 2006/000388, WO 2006/058737, WO 2006/000389, WO 2007/065549, WO 2007/115610, U.S. Pat. No. 7,250,532 B2, DE 102005058557 A1, CN 1583691 A, JP 08053397 A, U.S. Pat. No. 6,251,531 B1, US 2006/210830 A, EP 1957606 A1, and US 2008/0113101 A1, the whole contents of which are incorporated herein by reference.

Examples of singlet light emitters based on distyrylbenzene and its derivatives may be found in, for example, U.S. Pat. No. 5,121,029.

Especially, singlet emitters may be selected from the group consisting of: indenofluorene-amine and indenofluorene-diamine such as disclosed in WO 2006/122630, benzoindenofluorene-amine and benzoindenofluorene-diamine such as disclosed in WO 2008/006449, dibenzoindenofluorene-amine and dibenzoindenofluorene-diamine such as disclosed in WO2007/140847.

Other materials useful as singlet emitters include, but not limited to, polycyclic aromatic compounds, especially any one selected from the derivatives of the following compounds: anthracenes such as 9,10-di-naphthylanthracene, naphthalene, tetraphenyl, oxyanthene, phenanthrene, perylene such as 2,5,8,11-tetra-t-butylatedylene, indenoperylene, phenylenes such as 4,4'-(bis (9-ethyl-3-carbazovinylene)-1,1'-biphenyl, periflanthene, decacyclene, coronene, fluorene, spirobifluorene, arylpyren (e.g., US20060222886), arylenevinylene (e.g., U.S. Pat. Nos. 5,121,029, 5,130,603), cyclopentadiene such as tetraphenylcyclopentadiene, rubrene, coumarine, rhodamine, quinacridone, pyrane such as 4 (dicyanoethylene)-6-(4-dimethylaminostyryl-2-methyl)-4H-pyrane (DCM), thiapyran, bis (azinyl) imine-boron compounds (US 2007/0092753 A1), bis (azinyl) methene compounds, carbostyryl compounds, oxazone, benzoxazole, benzothiazole, benzimidazole, and diketopyrrolopyrrole. Examples of some singlet emitter materials may be found in the following patent documents: US 20070252517 A1, U.S. Pat. Nos. 4,769,292, 6,020,078, US 2007/0252517 A1, and US 2007/0252517 A1, the whole contents of which are incorporated herein by reference.

Some examples of suitable singlet emitters are listed in the table below:

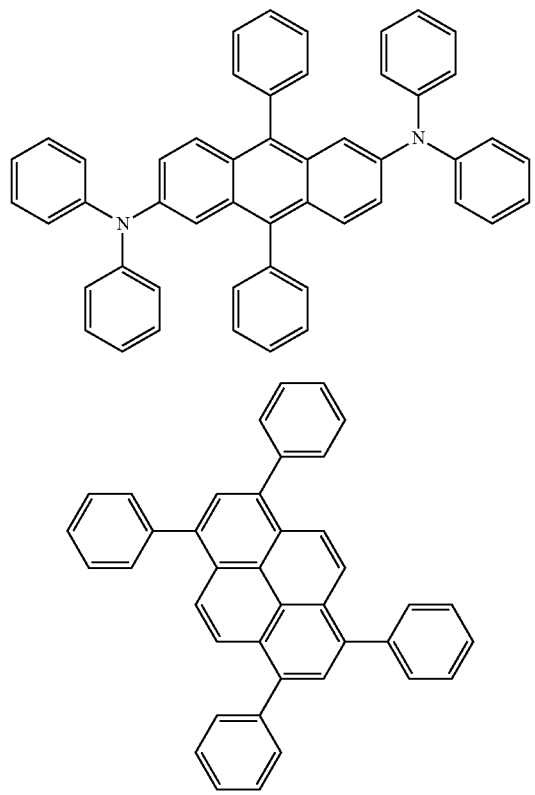

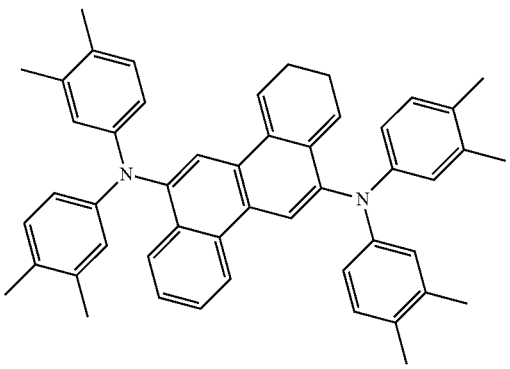

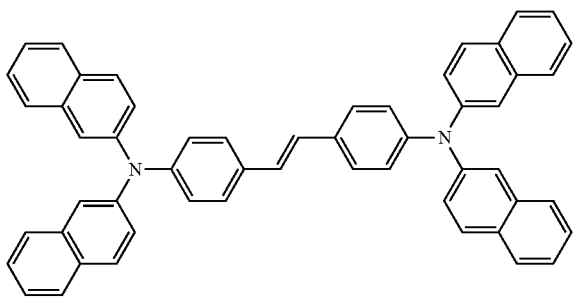 [SMILES: C(=C\c1ccc(N(c2ccc3ccccc3c2)c2ccc3ccccc3c2)cc1)/c1ccc(N(c2ccc3ccccc3c2)c2ccc3ccccc3c2)cc1]

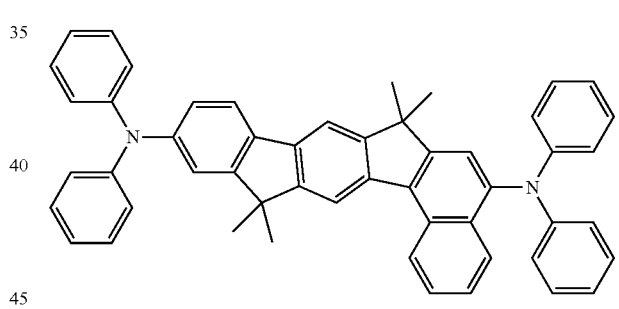

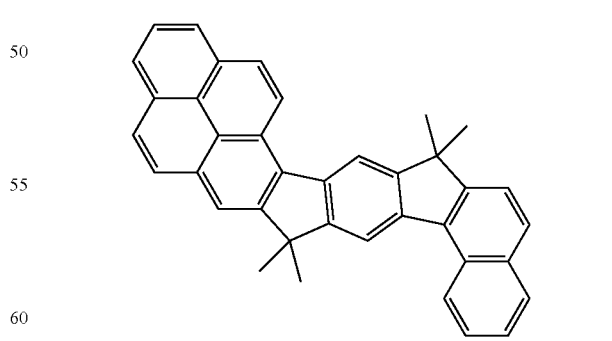

4. Thermally Activated Delayed Fluorescent Material (TADF):

Traditional organic fluorescent materials can only emit light using 25% singlet excitonic luminescence formed by electrical excitation, and the devices have relatively low internal quantum efficiency (up to 25%). The phosphorescent material enhances the intersystem crossing due to the strong spin-orbit coupling of the heavy atom center, the singlet exciton and the triplet exciton luminescence formed by the electric excitation can be effectively utilized, so that the internal quantum efficiency of the device can reach 100%. However, the phosphor materials are expensive, the material stability is poor, and the device efficiency roll-off is a serious problem, which limit its application in OLED. Thermally-activated delayed fluorescent materials are the third generation of organic light-emitting materials developed after organic fluorescent materials and organic phosphorescent materials. This type of material generally has a small singlet-triplet energy level difference (ΔEst), and triplet excitons can be converted to singlet excitons by intersystem crossing to emit light. This can make full use of the singlet excitons and triplet excitons formed under electric excitation. The device can achieve 100% quantum efficiency. At the same time, the material has a controllable structure, stable properties, a low cost without a precious metal, and has a promising prospect in the application of OLED field.

The TADF material needs to have a small singlet-triplet energy level difference, in one embodiment ΔEst <0.3 eV, further ΔEst <0.2 eV, and still further ΔEst <0.1 eV In some embodiments, TADF material has a small ΔEst, and in another embodiment, TADF material has good fluorescence quantum efficiency. Some TADF emitting materials can be found in the following patent documents or articles: CN103483332(A), TW201309696(A), TW201309778(A), TW201343874(A), TW201350558(A), US20120217869 (A1), WO2013133359(A1), WO2013154064 (A1), Adachi, et.al. Adv. Mater., 21, 2009, 4802, Adachi, et.al. Appl. Phys. Lett., 98, 2011, 083302, Adachi, et.al. App. Phys. Left., 101, 2012, 093306, Adachi, et.al. Chem. Commun., 48, 2012, 11392, Adachi, et.al. Nature Photonics, 6, 2012, 253, Adachi, et.al. Nature, 492, 2012, 234, Adachi, et.al. J. Am. Chem. Soc, 134, 2012, 14706, Adachi, et.al. Angew. Chem. It. Ed, 51, 2012, 11311, Adachi, et. al. Chem. Commun., 48, 2012, 9580, Adachi, et.al. Chem. Commun., 48, 2013, 10385, Adachi, et.al. Adv. Mater., 25, 2013, 3319, Adachi, et.al. Adv. Mater., 25, 2013, 3707, Adachi, et.al. Chem. Mater., 25, 2013, 3038, Adachi, et.al. Chem. Mater., 25, 2013, 3766, Adachi, et. Al. J. Mater. Chem. C., 1, 2013, 4599, Adachi, et.al. J. Phys. Chem. A., 117, 2013, 5607. The entire contents of the above listed patent or literature documents are hereby incorporated by reference.

Some examples of suitable TADF light-emitting materials are listed in the following table:

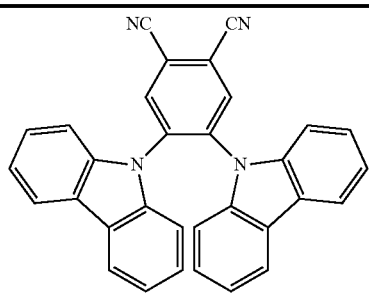

-continued

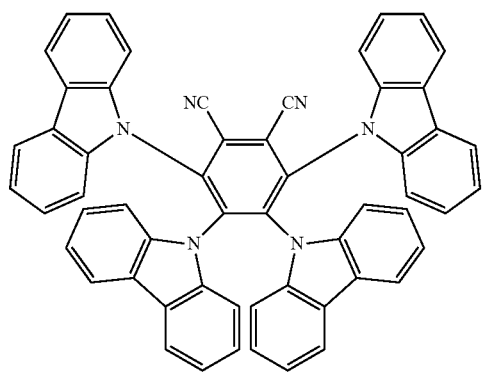 [SMILES: N#Cc1c(C#N)c(-n2c3ccccc3c3ccccc32)c(-n2c3ccccc3c3ccccc32)c(-n2c3ccccc3c3ccccc32)c1-n1c2ccccc2c2ccccc21]

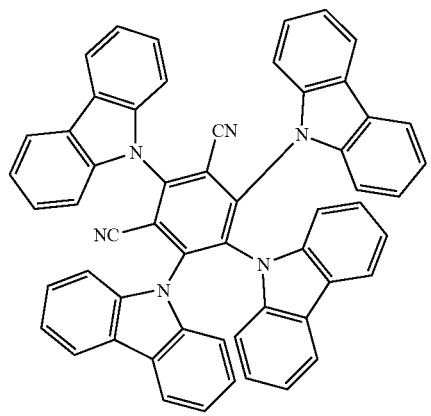 [SMILES: N#Cc1c(-n2c3ccccc3c3ccccc32)c(C#N)c(-n2c3ccccc3c3ccccc32)c(-n2c3ccccc3c3ccccc32)c1-n1c2ccccc2c2ccccc21]

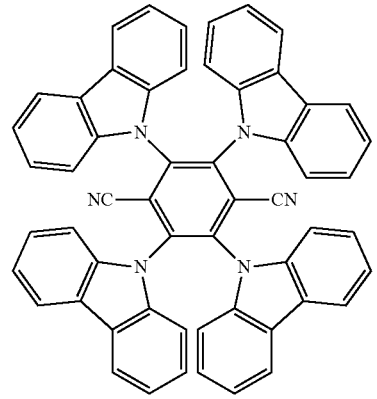 [SMILES: N#Cc1c(-n2c3ccccc3c3ccccc32)c(-n2c3ccccc3c3ccccc32)c(C#N)c(-n2c3ccccc3c3ccccc32)c1-n1c2ccccc2c2ccccc21]

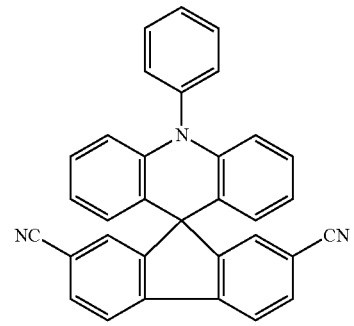 [SMILES: N#Cc1ccc2c(c1)C1(c3cc(C#N)ccc3-2)c2ccccc2N(c2ccccc2)c2ccccc21]

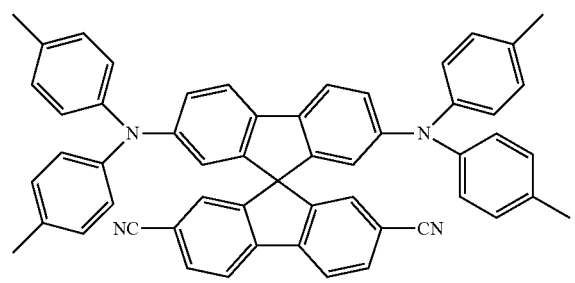
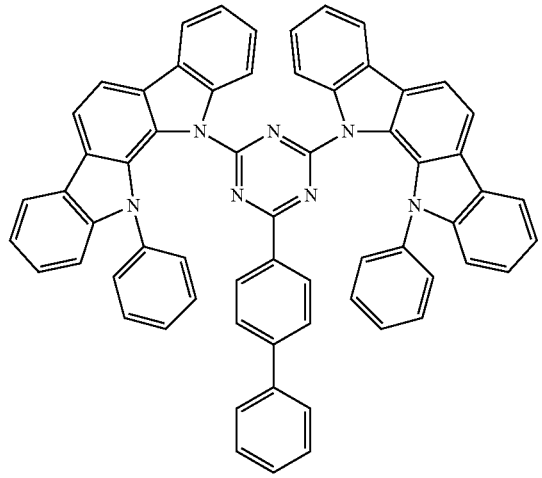
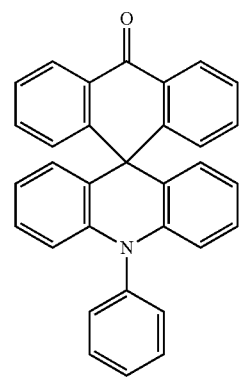 [SMILES: O=C1c2ccccc2C2(c3ccccc31)c1ccccc1N(c1ccccc1)c1ccccc12]
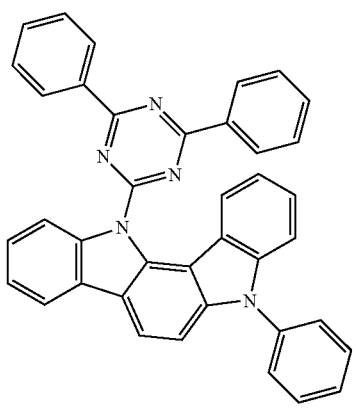
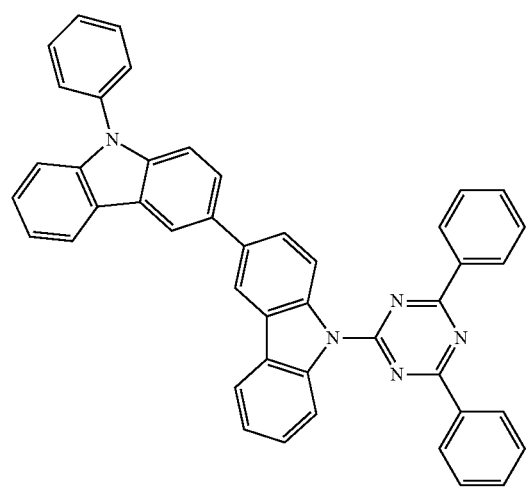 [SMILES: c1ccc(-c2nc(-c3ccccc3)nc(-n3c4ccccc4c4cc(-c5ccc6c(c5)c5ccccc5n6-c5ccccc5)ccc43)n2)cc1]
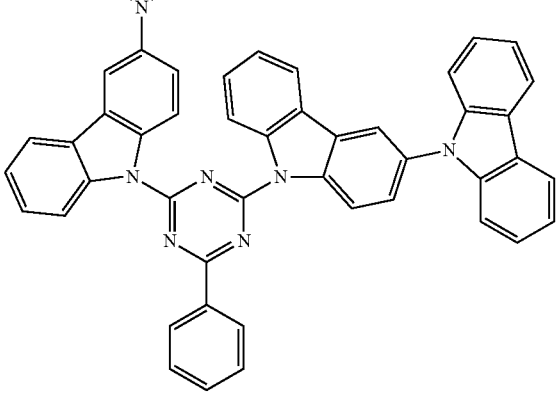
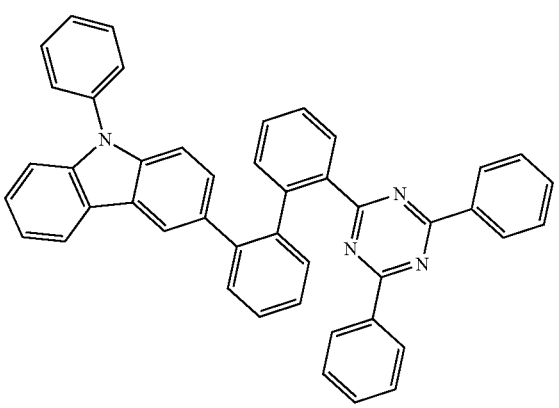 [SMILES: c1ccc(-c2nc(-c3ccccc3)nc(-c3ccccc3-c3ccccc3-c3ccc4c(c3)c3ccccc3n4-c3ccccc3)n2)cc1]
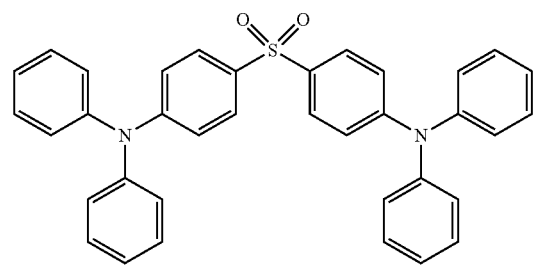 [SMILES: O=S(=O)(c1ccc(N(c2ccccc2)c2ccccc2)cc1)c1ccc(N(c2ccccc2)c2ccccc2)cc1]

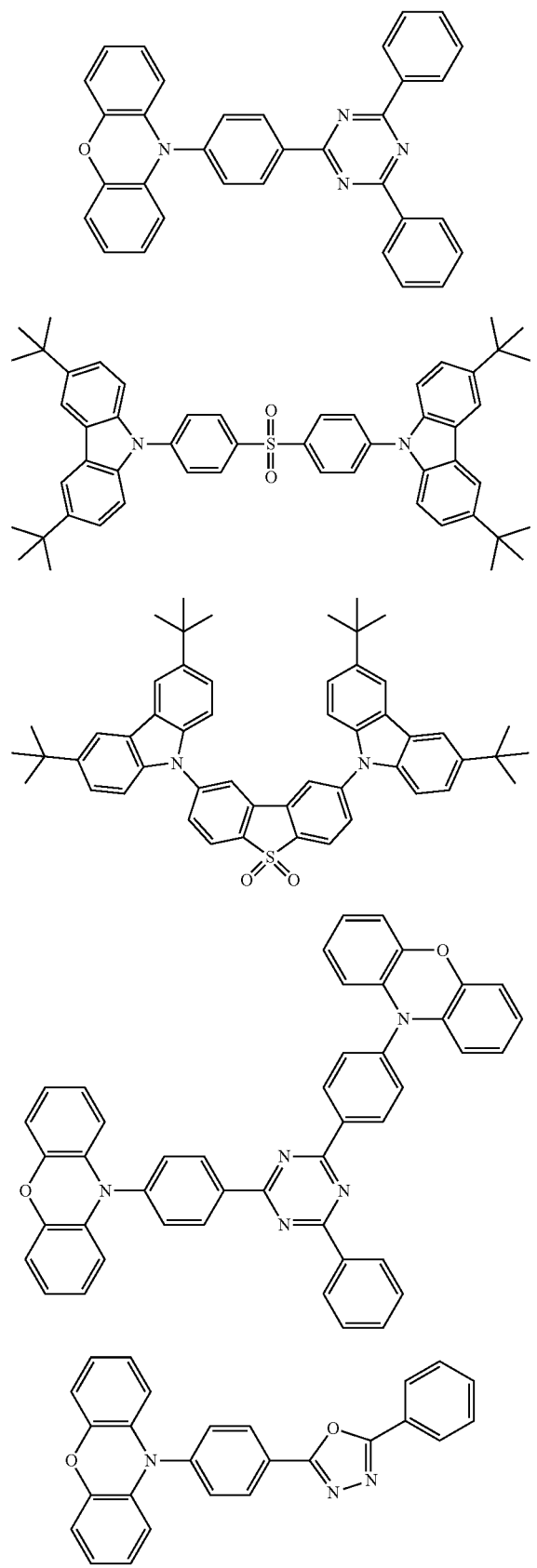
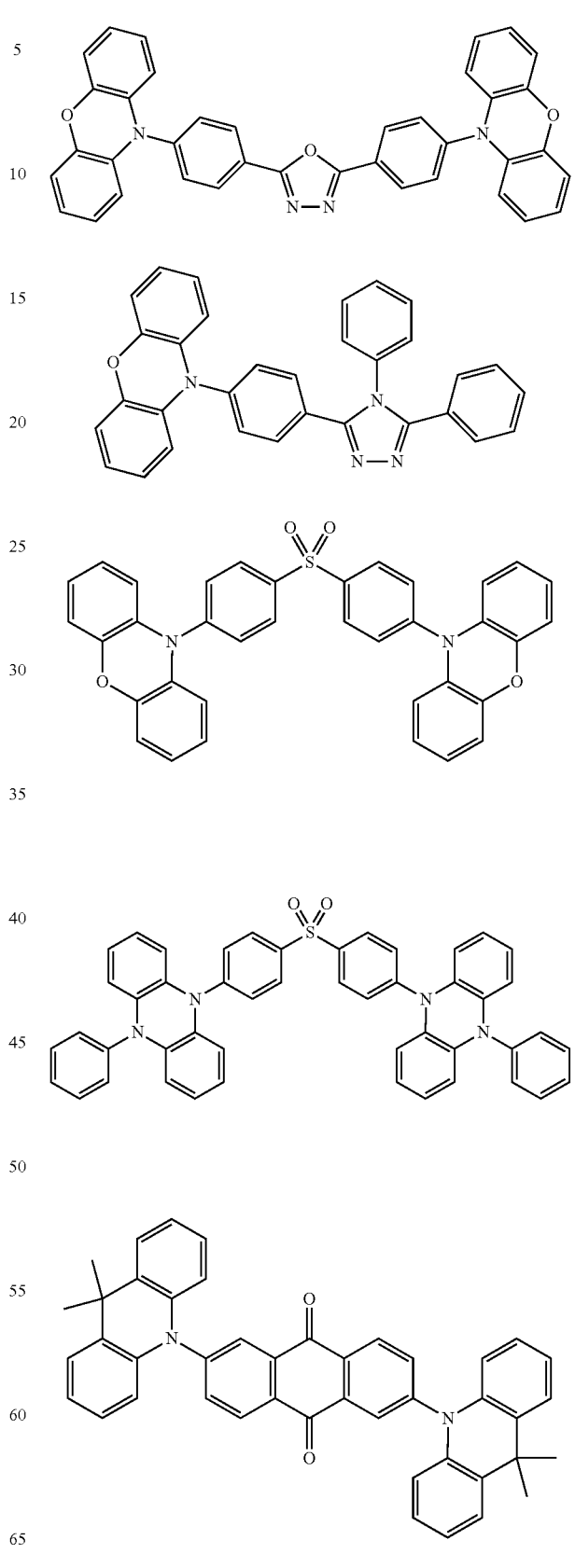

85
-continued
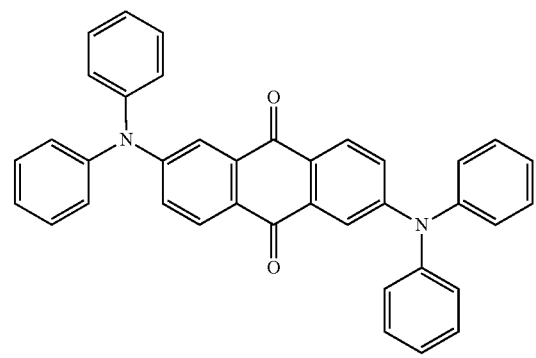 [SMILES: O=C1c2ccc(N(c3ccccc3)c3ccccc3)cc2C(=O)c2ccc(N(c3ccccc3)c3ccccc3)cc21]
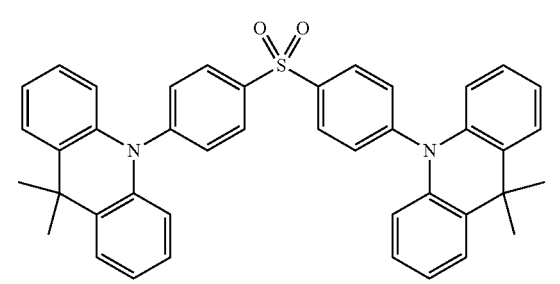
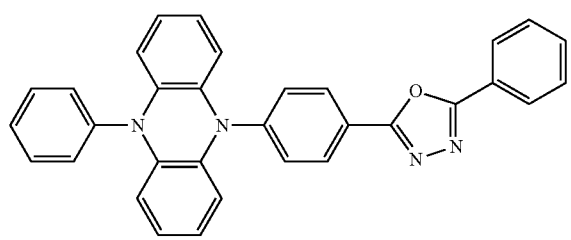 [SMILES: c1ccc(-c2nnc(-c3ccc(N4c5ccccc5N(c5ccccc5)c5ccccc54)cc3)o2)cc1]
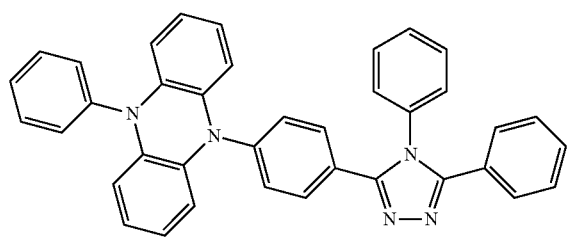 [SMILES: c1ccc(-c2nnc(-c3ccc(N4c5ccccc5N(c5ccccc5)c5ccccc54)cc3)n2-c2ccccc2)cc1]
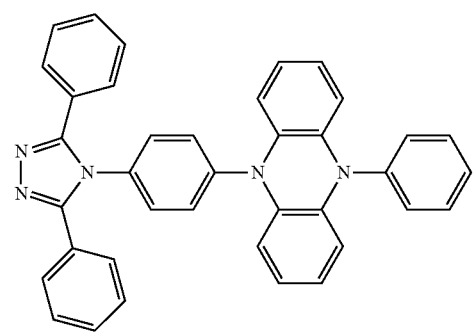 [SMILES: c1ccc(-c2nnc(-c3ccccc3)n2-c2ccc(N3c4ccccc4N(c4ccccc4)c4ccccc43)cc2)cc1]
86
-continued
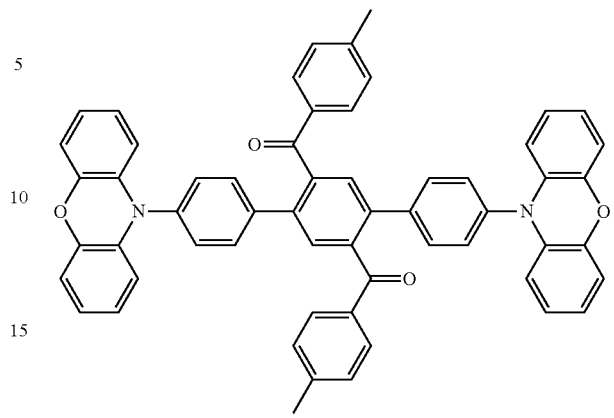
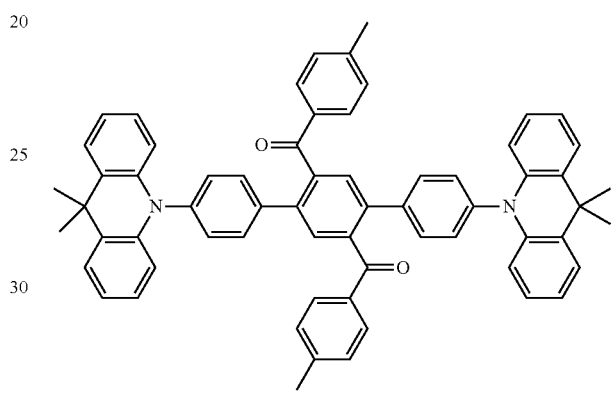
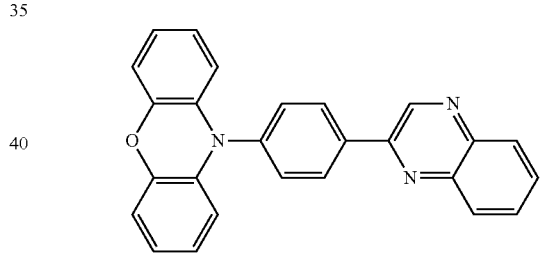
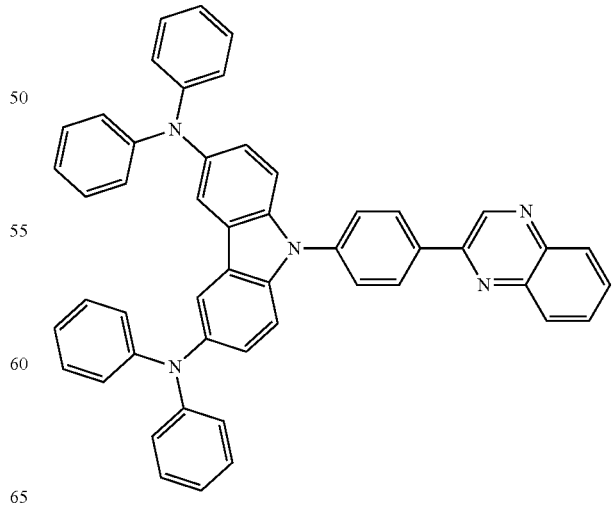

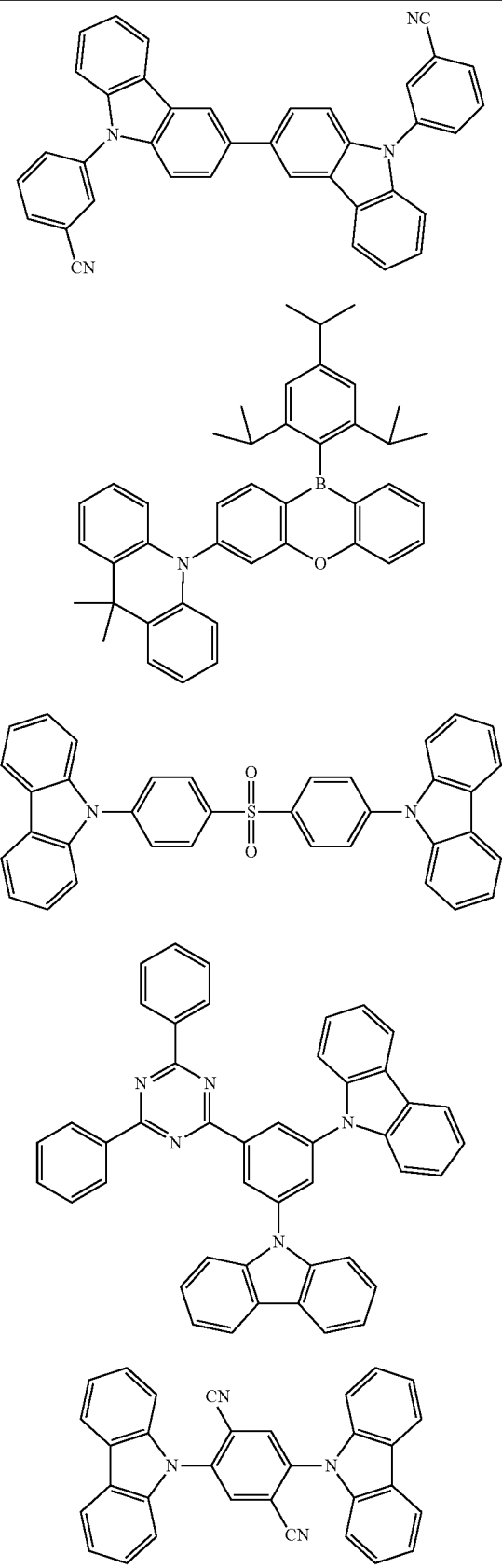
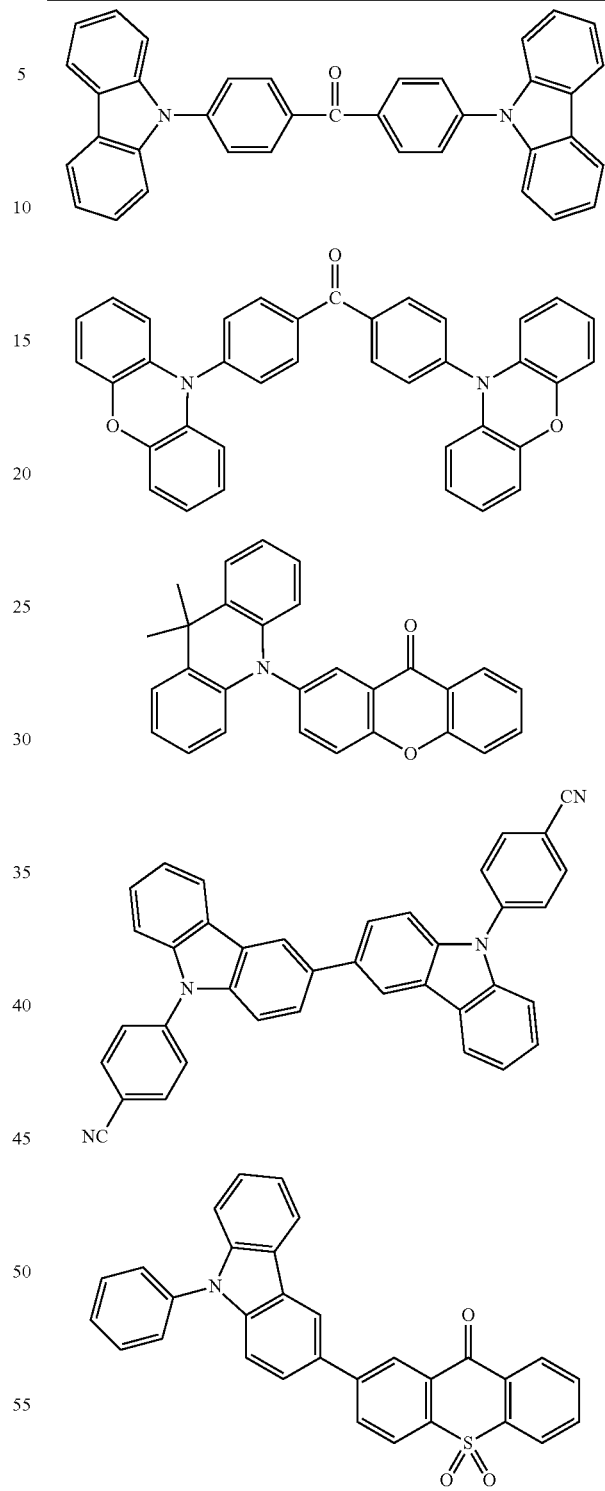

The publications of above mentioned organic functional materials are incorporated herein by reference for the purpose of disclosure.

In one embodiment, the fused ring compound is used for evaporated OLED device. For this purpose, the fused ring compound has a molecular weight of ≤1000 g/mol, further, the fused ring compound has a molecular weight of ≤900 g/mol, still further, the fused ring compound has a molecular weight of ≤850 g/mol, still further, the fused ring compound has a molecular weight of ≤800 g/mol, even further, the fused ring compound has a molecular weight of ≤700 g/mol.

Another purpose of the present disclosure is to provide material solutions for printing OLED.

For this purpose, the fused ring compound has a molecular weight of ≥700 g/mol, further, the fused ring compound has a molecular weight of ≥900 g/mol, still further, the fused ring compound has a molecular weight of ≥900 g/mol, still further, the fused ring compound has a molecular weight of ≥1000 g/mol, still further, the fused ring compound has a molecular weight of ≥1100 g/mol.

In other embodiments, at 25° C., the fused ring compound or the polymer has a solubility in toluene of ≥2 mg/ml, further ≥3 mg/ml, and still further ≥5 mg/ml.

The present disclosure also provides a formulation comprising the fused ring compound and an organic solvent, or comprising the polymer and an organic solvent.

In some embodiments, the fused ring compound can be used as singlet emitter material in the formulation.

In other embodiments, the formulation further comprises a host material.

In a preferred embodiment, the formulation further comprises a host material and a singlet emitter.

In another embodiment, the formulation further comprises at least two host materials.

In another embodiment, the formulation further comprises a host material and a thermally activated delayed fluorescent material.

In other embodiments, the formulation further comprises a hole transport material (HTM), and particularly, the HTM comprises a crosslinkable group.

In one embodiment, the formulation is a solution.

In another embodiment, the formulation is a suspension.

The formulation in the embodiment of the disclosure may include the fused ring compound or the polymer in an amount of 0.01 to 20 wt %, further 0.1 to 15 wt %, still further 0.2 to 10 wt %, and even further 0.25 to 5 wt %.

In some embodiments, the organic solvent is selected from the group consisting of aromatic or heteroaromatic, ester, aromatic ketone or aromatic ether, aliphatic ketone or aliphatic ether, alicyclic or olefinic compound, inorganic ester compound such as borate ester or a phosphate ester, and combinations thereof.

In other embodiments, the formulation comprises an aromatic or heteroaromatic solvent in an amount of at least 50 wt %, further at least 80 wt %, and particularly at least 90 wt %.

Examples of the aromatic or heteroaromatic solvent include, but are not limited to, 1-tetralone, 3-phenoxytoluene, acetophenone, 1-methoxynaphthalene, p-diisopropylbenzene, amylbenzene, tetrahydronaphthalene, cyclohexylbenzene, chloronaphthalene, 1,4-dimethylnaphthalene, 3-isopropylbiphenyl, p-methylisopropylbenzene, dipentylbenzene, o-diethylbenzene, m-diethylbenzene, p-diethylbenzene, 1,2,3,4-tetramethylbenzene, 1,2,3,5-tetramethylbenzene, 1,2,4,5-tetramethylbenzene, butylbenzene, dodecylbenzene, 1-methylnaphthalene, 1,2,4-trichlorobenzene, 1,3-dipropoxybenzene, 4,4-difluorodiphenylmethane, diphenyl ether, 1,2-dimethoxy-4-(1-propenyl)benzene, diphenylmethane, 2-phenylpyridine, 3-phenylpyridine, 2-phenoxymethyl ether, 2-phenoxytetrahydrofuran, ethyl-2-naphthyl ether, N-methyldiphenylamine, 4-isopropylbiphenyl, α,α-dichlorodiphenylmethane, 4-(3-phenylpropyl)pyridine, benzyl benzoate, 1,1-bis(3,4-dimethylphenyl)ethane, 2-isopropylnaphthalene, dibenzyl ether, and the like.

In other embodiments, the organic solvent is aliphatic, alicyclic or aromatic hydrocarbon, amine, thiol, amide, nitrile, ester, ether, polyether, alcohol, diol or polyol.

In other embodiments, the organic solvent is alcohol. Especially alcohol includes alkylcyclohexanol, particularly methylated aliphatic alcohol, naphthol, and the like.

The organic solvent may be a cycloalkane, such as decalin.

The organic solvent may be used alone or as a mixture of two or more organic solvents.

In certain embodiments, the organic solvent comprises, but not limited to, methanol, ethanol, 2-methoxyethanol, dichloromethane, trichloromethane, chlorobenzene, o-dichlorobenzene, tetrahydrofuran, anisole, morpholine, toluene, o-xylene, m-xylene, p-xylene, 1,4-dioxane, acetone, methyl ethyl ketone, 1,2-dichloroethane, 3-phenoxy toluene, 1,1,1-trichloroethane, 1,1,2,2-tetrachloroethane, ethyl acetate, butyl acetate, dimethylformamide, dimethylacetamide, dimethyl sulfoxide, tetrahydronaphthalene, decalin, indene, and/or mixtures thereof.

In some embodiments, the organic solvent is a solvent having Hansen solubility parameters in the following range:

$\delta_d$ (dispersion force) in the range of 17.0~23.2 $MPa^{1/2}$, especially in the range of 18.5~21.0 $MPa^{1/2}$;

$\delta_p$ (polarity force) in the range of 0.2~12.5 $MPa^{1/2}$, especially in the range of 2.0~6.0 $MPa^{1/2}$;

$\delta_h$ (hydrogen bonding force) in the range of 0.9~14.2 $MPa^{1/2}$, especially in the range of 2.0~6.0 $MPa^{1/2}$.

According to the formulation of the disclosure, wherein the boiling point parameter of the organic solvent must be taken into account when selecting the organic solvent. In the present disclosure, the boiling point of the organic solvent is ≥150° C., further ≥180° C., still further ≥200° C., still further ≥250° C., and even further ≥275° C. or 300° C. Boiling points in these ranges are beneficial for preventing the nozzle of the inkjet printing head from clogging. The organic solvent can be evaporated from the solvent system to form a film comprising the functional material.

In some embodiments, the formulation according to the present disclosure has:

1) a viscosity in the range of 1 cPs to 100 cPs at 25° C.; and/or 2) a surface tension in the range of 19 dyne/cm to 50 dyne/cm at 25° C.

According to the formulation of the present disclosure, the surface tension parameter of the organic solvent must be taken into account when selecting the organic solvent. The suitable surface tension parameters of the ink are suitable for the particular substrate and particular printing method. For example, for inkjet printing, in an embodiment, the surface tension of the organic solvent at 25° C. is in the range of about 19 dyne/cm to about 50 dyne/cm, further in the range of about 22 dyne/cm to 35 Dyne/cm, and still further in the range of about 25 dyne/cm to 33 dyne/cm.

In some embodiment, the surface tension of the ink according to the present disclosure at 25° C. is in the range of about 19 dyne/cm to 50 dyne/cm, further in the range of about 22 dyne/cm to 35 dyne/cm, and still further in the range of about 25 dyne/cm to 33 dyne/cm.

According to the formulation of the present disclosure, the viscosity parameters of the ink of the organic solvent must be taken into account when selecting the organic solvent. The viscosity can be adjusted by different methods, such as by the selection of appropriate organic solvent and the concentration of functional materials in the ink. In a preferred embodiment, the viscosity of the organic solvent is less than 100 cps, further less than 50 cps, and still further 1.5 to 20 cps. The viscosity herein refers to the viscosity during printing at the ambient temperature that is generally at 15-30° C., further 18-28° C., still further 20-25° C., especially 23-25° C. The formulation so formulated will be particularly suitable for inkjet printing.

In a further embodiment, the formulation according to the present disclosure has a viscosity in the range of about 1 cps to 100 cps, especially in the range of 1 cps to 50 cps, and particularly in the range of 1.5 cps to 20 Cps range at 25° C.

The ink obtained from the organic solvent satisfying the above-mentioned boiling point parameter, surface tension parameter and viscosity parameter can form a functional material film with uniform thickness and composition property.

Another object of the present disclosure is to provide an application of the fused ring compound or polymer described above in organic electronic devices.

The organic electronic devices can be selected from the group consisting of an organic light-emitting diode (OLED), an organic photovoltaic cell (OPV), an organic light-emitting electrochemical cell (OLEEC), an organic field effect transistor (OFET), an organic light-emitting field effect transistor, organic laser, an organic spintronic device, an organic sensor, and an organic plasmon emitting diode.

Another object of the present disclosure is to provide a method for preparing thee organic electronic device described above.

The specific technical solution is described below:

A method for preparing the organic electronic device, comprising: forming a functional layer by evaporating the fused ring compound or the mixture described above on a substrate; or forming a functional layer by co-evaporating the fused ring compound together with the second organic functional material on a substrate; or forming a functional layer by coating the formulation described above on a substrate via printing or coating. The printing or coating method can be selected from, but not limited to, inkjet printing, nozzle printing, typography, screen printing, dip coating, spin coating, blade coating, roller printing, torsion roller printing, lithography, flexographic printing, rotary printing, spray coating, brush coating, pad printing, slot die coating, etc.

The disclosure also relates to the use of the formulation as printing ink when preparing organic electronic devices, particularly by the preparation method of printing or coating.

Suitable printing or coating techniques include, but are not limited to, inkjet printing, typography, screen printing, dip coating, spin coating, blade coating, roller printing, torsion roller printing, lithography, flexographic printing, rotary printing, spray coating, brush coating, pad printing, slot die coating, etc., especially gravure printing, screen printing and inkjet printing. Gravure printing, inkjet printing will be applied in embodiments of the present disclosure. The solution or suspension may additionally comprise one or more components such as surface-active compound, lubricant, wetting agent, dispersant, hydrophobic agent, binder, etc., for adjusting viscosity and film forming property, enhancing adhesion, and the like. For more information about printing technologies and their relevant requirements on related solutions, such as solvents and concentration, viscosity, etc., please see Handbook of Print Media: Technologies and Production Methods, ISBN 3-540-67326-1, edited by Helmut Kipphan.

In a method for preparing the organic electronic device as described above, the functional layer has a thickness of 5 nm to 1000 nm.

The present disclosure further relates to an organic electronic device comprising the fused ring compound or the polymer as described above. The organic electronic device comprises at least one functional layer prepared from the fused ring compound or the polymer. Generally, the organic electronic device comprises at least a cathode, an anode, and a functional layer located between the cathode and the anode, wherein the functional layer comprises the fused ring compound or the polymer.

In some embodiment, the above-mentioned organic electronic device is an organic electroluminescent device, particularly an OLED, as shown in FIG. 1, comprising a substrate 101, an anode 102, and at least one light emitting layer 104 and a cathode 106.

The substrate 101 may be opaque or transparent. A transparent substrate can be used to make a transparent light emitting device. See, e.g., Bulovic et al. Nature 1996, 380, p 29 and Gu et al. ppl. Phys. Lett. 1996, 68, p 2606. The substrate can be rigid or elastic. The substrate can be plastic, metal, semiconductor wafer or glass. Particularly the substrate has a smooth surface. Substrate without surface defect is a particularly good choice. In a further embodiment, the substrate is flexible and may be selected from polymer film or plastic, with its glass transition temperature $T_g$ of greater than 150° C., further greater than 200° C., still further greater than 250° C., and even further greater than 300° C. Examples of suitable flexible substrates include poly(ethylene terephthalate) (PET) and polyethylene glycol (2,6-naphthalene) (PEN).

The anode 102 may comprise a conductive metal or a metal oxide, or a conductive polymer. The anode can easily inject holes into hole injection layer (HIL), hole transport layer (HTL) or light-emitting layer. In one embodiment, the absolute value of the difference between the work function of the anode and the HOMO energy level or valence band energy level of the emitter in the light-emitting layer or the p-type semiconductor material as HIL or HTL or electron blocking layer (EBL) is less than 0.5, further less than 0.3 eV, and even further less than 0.2 eV. Examples of anode materials comprise, but not limited to, Al, Cu, Au, Ag, Mg, Fe, Co, Ni, Mn, Pd, Pt, ITO, aluminum doped zinc oxide (AZO), and the like. Other suitable anode materials are known and can be readily selected by the ordinary skill in the art. The anode material may be deposited using any suitable technique, such as a suitable physical vapor deposition method, including radio frequency magnetron sputtering, vacuum thermal evaporation, e-beam, and the like. In certain embodiments, the anode is patterned. Patterned ITO conductive substrates are commercially available and can be used to prepare the device according to the present disclosure.

Cathode 106 may include a conductive metal or a metal oxide. The cathode can easily inject electrons into EIL or ETL or directly into light-emitting layer. In one embodiment, the absolute value of the difference between the work function of the cathode and the LUMO energy level or conduction band energy level of the emitter in the light-emitting layer or the n-type semiconductor material as electron injection layer (EIL) or electron transport layer (ETL) or hole blocking layer (HBL) is less than 0.5, further less than 0.3 eV, and still further less than 0.2 eV. In principle, all materials that can be used as cathodes for OLED can be used as cathode materials for the devices of the disclosure. Examples of the cathode materials comprise, but not limited to: Al, Au, Ag, Ca, Ba, Mg, LiF/Al, MgAg alloy, $BaF_2$/Al, Cu, Fe, Co, Ni, Mn, Pd, Pt, ITO, and the like. The cathode material may be deposited using any suitable technique, such as a suitable physical vapor deposition method, including radio frequency magnetron sputtering, vacuum thermal evaporation, e-beam, and the like.

OLED can also comprise other functional layers such as hole injection layer (HIL) or hole transport layer (HTL) 103, electron blocking layer (EBL), electron injection layer (EIL) or electron transport layer (ETL) 105, and hole blocking layer (HBL). Materials which are suitable for using in these functional layers are described in detail in WO2010135519A1, US20090134784A1 and WO2011110277A1, the entire contents of which are hereby incorporated herein by reference.

In one embodiment, the organic electroluminescent device according to the present disclosure has a light emitting layer 104 prepared by vacuum evaporation, with an evaporation source comprising the fused ring compound.

In another embodiment, the organic electroluminescent device according to the present disclosure has a light emitting layer 104 prepared by printing the formulation according to the present disclosure.

The light-emitting wavelength of the organic electroluminescent device according to the present disclosure is between 300 and 1000 nm, further between 350 and 900 nm, and still further between 400 and 800 nm.

The present disclosure also relates to the application of the organic electronic device according to the present disclosure in various electronic equipments, comprising but not limited to display equipment, lighting equipment, light source, and sensor, and the like.

The present disclosure also relates to electronic equipments comprising the organic electronic device according to the present disclosure, comprising but not limited to display equipment, illumination equipment, light source, sensor, and the like.

The present disclosure will be described below with reference to the embodiments, but the present disclosure is not limited to the following embodiments. It should be understood that the appended claims summarized the scope of the present disclosure. Those skilled in the art should realize that changes to the embodiments of the present disclosure that are made under the guidance of the concept of the present disclosure will be covered by the spirit and scope of the claims of the present disclosure.

Example 1: Synthesis of Compound 1

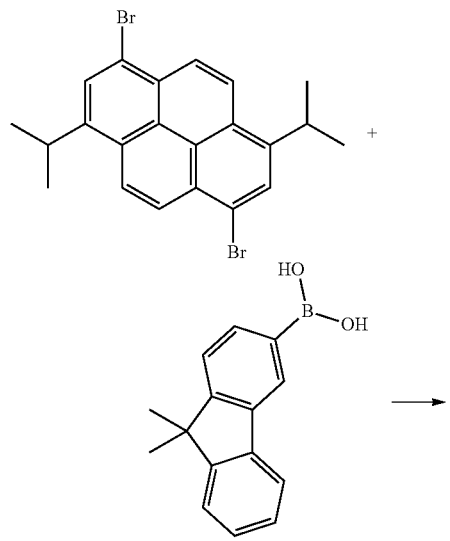

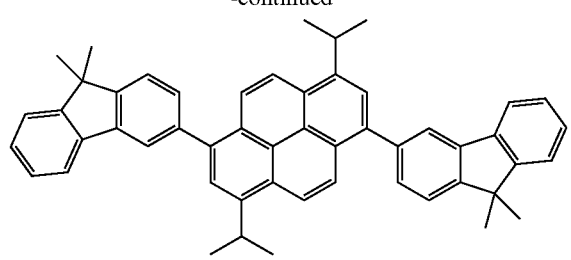

To a 250 mL three-necked flask equipped with a condenser, 1,6-dibromo-3,8-diisopropylpyrene (6.2 g, 14 mmol), (9,9-dimethylfluorene-3-yl) boric acid (6.7 g, 28 mmol), Pd(PPh$_3$)$_4$ (920 mg, 0.8 mmol), potassium carbonate (11 g, 80 mmol), 120 mL toluene and 40 mL water were added under a stream of nitrogen, and stirred at 90° C. overnight. After completion of the reaction, the solution was purified by column chromatography to give a pale-yellow solid powder (7.8 g, 83%).

Example 2: Synthesis of Compound 2

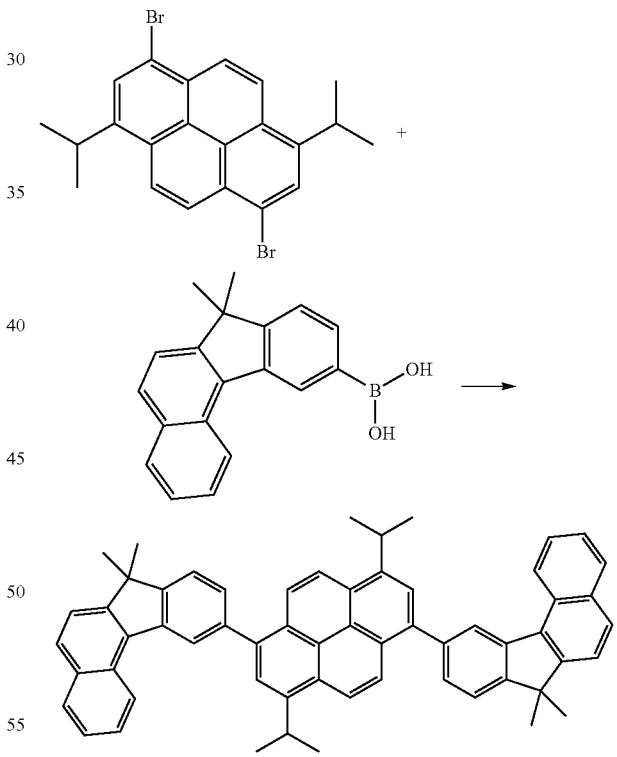

To a 500 mL three-necked flask equipped with a condenser, 1,6-dibromo-3,8-diisopropylpyrene (6.7 g, 15 mmol), (7,7-dimethyl-benzofluorene-10-yl) boric acid (8.7 g, 30 mmol), Pd(PPh$_3$)$_4$ (1.04 g, 0.9 mmol), potassium carbonate (8.6 g, 90 mmol), 140 mL toluene and 40 mL water were added under a stream of nitrogen, and stirred at 90° C. overnight. After completion of the reaction, the solution was purified by column chromatography to give a pale-yellow solid powder (8.8 g, 76%).

Example 3: Synthesis of Compound 3

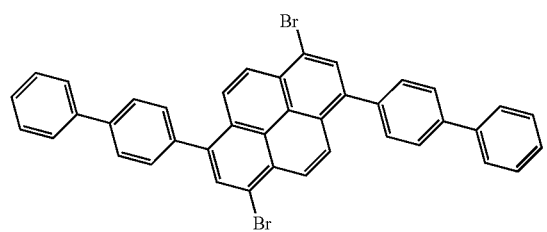

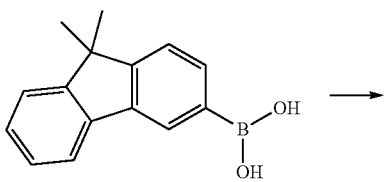

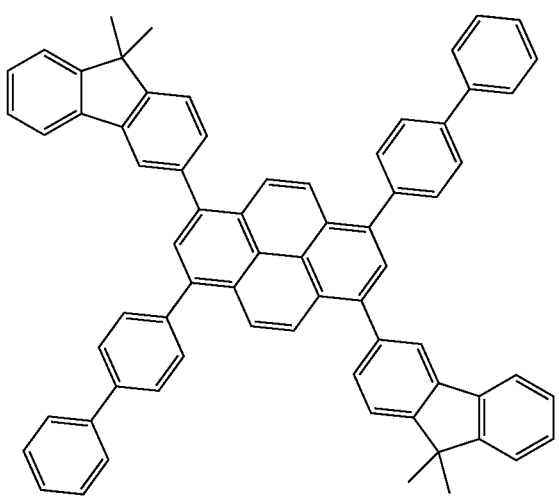

To a 250 mL three-necked flask equipped with a condenser, 1,6-bis([1,1'-biphenyl]-4-yl)-3,8-dibromopyrene (6.6 g, 10 mmol), (9,9-dimethylfluorene-3-yl) boric acid (4.7 g, 20 mmol), Pd(PPh$_3$)$_4$ (690 mg, 0.6 mmol), potassium carbonate (8.3 g, 60 mmol), 120 mL toluene and 40 mL water were added under a stream of nitrogen, and stirred at 90° C. overnight. After completion of the reaction, the solution was purified by column chromatography to give a pale-yellow solid powder (6.1 g, 69%).

Example 4: Synthesis of Compound 4

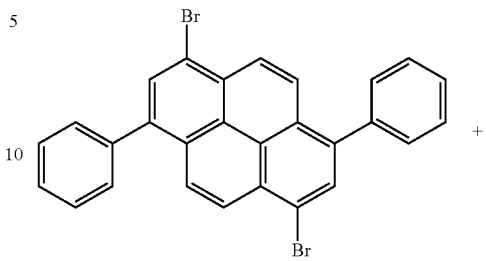

To a 500 mL three-necked flask equipped with a condenser, 1,6-dibromo-3,8-diphenylpyrene (9.2 g, 18 mmol), (7,7-dimethyl-benzofluorene-10-yl) boric acid (10.4 g, 36 mmol), Pd(PPh$_3$)$_4$ (1.25 g, 1.08 mmol), potassium carbonate (14.9 g, 108 mmol), 200 mL toluene and 50 mL water were added under a stream of nitrogen, and stirred at 90° C. overnight. After completion of the reaction, the solution was purified by column chromatography to give a pale-yellow solid powder (10.6 g, 70%).

Example 5: Synthesis of Compound 5

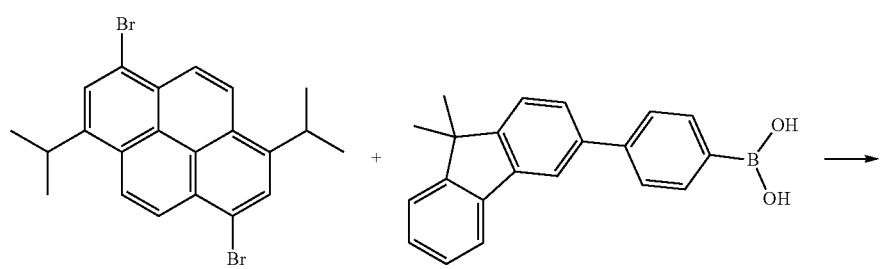

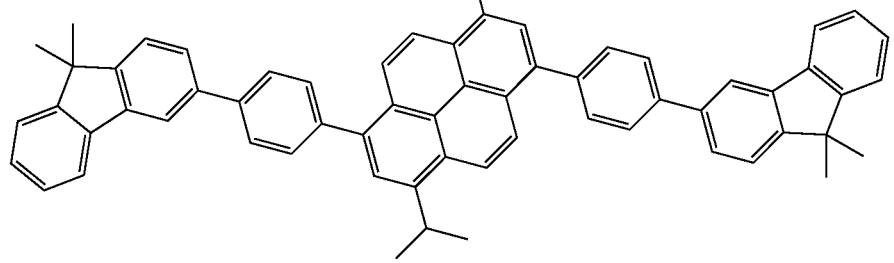

To a 500 mL three-necked flask equipped with a condenser, 1,6-dibromo-3,8-diisopropylpyrene (6.7 g, 15 mmol), (4-(9,9-dimethylfluorene-3-yl)phenyl) boric acid (9.4 g, 30 mmol), Pd(PPh$_3$)$_4$ (1.04 g, 0.9 mmol), potassium carbonate (8.6 g, 90 mmol), 150 mL toluene and 40 mL water were added under a stream of nitrogen, and stirred at 90° C. overnight. After completion of the reaction, the solution was purified by column chromatography to give a pale-yellow solid powder (10.0 g, 81%).

Example 6: Synthesis of Compound 6

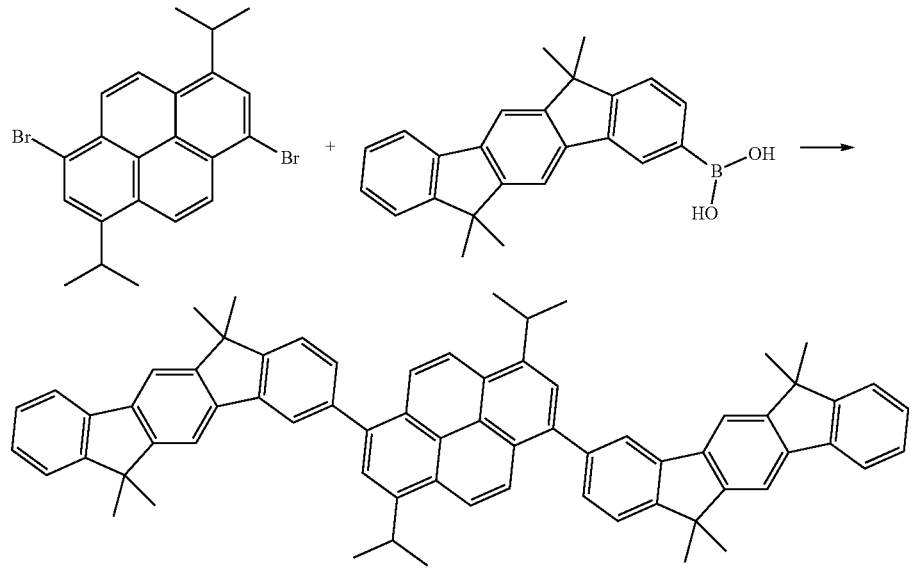

To a 250 mL three-necked flask equipped with a condenser, 1,6-dibromo-3,8-diisopropylpyrene (6.2 g, 14 mmol), (6,6,12,12-tetramethyl-indenofluorene)-3-yl boric acid (9.9 g, 28 mmol), Pd(PPh$_3$)$_4$ (920 mg, 0.8 mmol), potassium carbonate (11 g, 80 mmol), 120 mL toluene and 40 mL water were added under a stream of nitrogen, and stirred at 90° C. overnight. After completion of the reaction, the solution was purified by column chromatography to give a pale-yellow solid powder (8.1 g, 64%).

Example 7: Synthesis of Compound 7

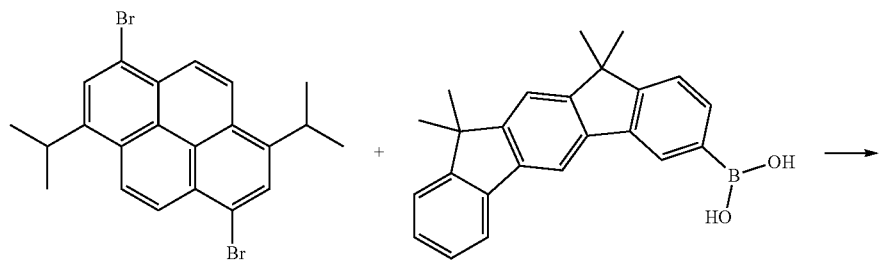

-continued

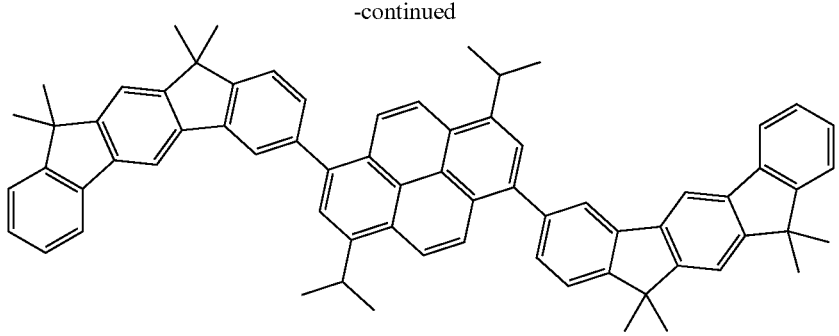

To a 250 mL three-necked flask equipped with a condenser, 1,6-dibromo-3,8-diisopropylpyrene (6.7 g, 15 mmol), (10,10,12,12-tetramethyl-indenofluorene)-3-yl boric acid (10.6 g, 30 mmol), Pd(PPh$_3$)$_4$ (1.04 g, 0.9 mmol), potassium carbonate (8.6 g, 90 mmol), 120 mL toluene and 40 mL water were added under a stream of nitrogen, and stirred at 90° C. overnight. After completion of the reaction, the solution was purified by column chromatography to give a pale-yellow solid powder (10.1 g, 75%).

Comparative Example 1: Synthesis of Comparative Compound 1

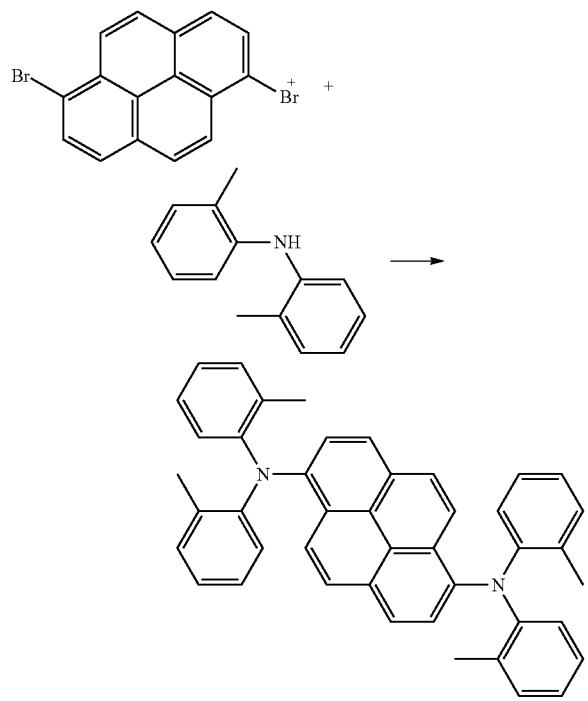

To a 500 mL three-necked flask equipped with a condenser, 1,6-dibromopyrene (7.2 g, 20 mmol), di-o-tolylamine (7.9 g, 40 mmol), Pd(dba)$_2$ (690 mg, 1.2 mmol), NaOtBu (11.5 g, 120 mmol), (tBu)$_3$P (730 mg, 3.6 mmol) and 150 mL anhydrous toluene were added under a stream of nitrogen, and stirred at 100° C. overnight. After completion of the reaction, the precipitated solid was filtered, washed with toluene and methanol to give a pale yellow solid powder (10.7 g, 90%).

Example 8: Preparation and Characterization of the OLED Devices

Materials used for each layer of the OLED device:
HIL: a triarylamine derivative;
HTL: a triarylamine derivative;
Host: an anthracene derivative:
Dopant: compound 1-compound 7, comparative compound 1.
OLED devices having ITO/HIL (50 nm)/HTL (35 nm)/Host: 5% Dopant (25 nm)/ETL (28 nm) /LiQ (1 nm)/Al (150 nm)/cathode are prepared as follows:
a. cleaning the conductive glass substrate by various solvents such as chloroform, ketone, and isopropanol when first used, and then treating the conductive glass substrate with ultraviolet ozone plasma;
b. preparing HIL (50 nm), HTL (35 nm), EML (25 nm), ETL (28 nm) by thermal evaporation in a high vacuum ($1 \times 10^{-6}$ mbar).
c. preparing cathode: LiQ/Al (1 nm/150 nm) by thermal evaporation in a high vacuum ($1 \times 10^{-6}$ mbar);
d. encapsulating the device with UV curable resin in a glove box filled with nitrogen gas.

The current-voltage (J-V) characteristics of each OLED device are characterized by a characterization equipment and important parameters such as efficiency, lifetime, and external quantum efficiency are recorded. After testing, it was found that the blue light-emitting device prepared by using compound 1 to compound 7 as the EML layer emitter has a better color coordinate than that prepared by comparative compound 1, for example, the device prepared by using compound 3 has a color coordinate of (0.149, 0.065); in addition, the blue light-emitting device prepared by using compound 1 to compound 7 as the EML layer emitter has luminous efficiency in the range of 6-8 cd/A, which is more excellent luminous efficiency. In terms of lifetime of the devices, the lifetime of the blue light-emitting device prepared by using compound 1 to compound 7 as the EML layer emitter is much better than that prepared by using comparative compound 1. For example, the device prepared by compound 3 has a T95 of greater than 1000 hours at 1000 nits.

The technical features of the above-described embodiments may be combined arbitrarily. To simplify the description, not all of the possible combinations of the technical features in the above embodiments are described. However, all of the combinations of these technical features should be considered as within the scope of the present disclosure, as long as such combinations do not contradict with each other.

The above-described embodiments merely represent several embodiments of the present disclosure, and the description thereof is more specific and detailed, but it should not be construed as limiting the scope of the present disclosure. It should be noted that, for those skilled in the art, several variations and improvements may be made without departing from the concept of the present disclosure, and these are all within the protection scope of the present disclosure. Therefore, the scope of protection of the present disclosure shall be subject to the appended claims.

What is claimed is:

1. A fused ring compound represented by general formula (I):

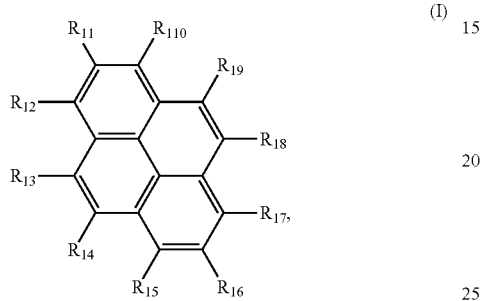

(I)

wherein
each of $R_{11}$, $R_{12}$, $R_{13}$, $R_{14}$, $R_{15}$, $R_{16}$, $R_{17}$, $R_{18}$, $R_{19}$ and $R_{110}$ is independently selected from the group consisting of H, a linear alkyl containing 1 to 20 C atoms, linear alkoxy containing 1 to 20 C atoms or linear thioalkoxy group containing 1 to 20 C atoms, a branched or cyclic alkyl containing 3 to 20 C atoms, branched or cyclic alkoxy containing 3 to 20 C atoms or branched or cyclic thioalkoxy group containing 3 to 20 C atoms, a substituted or unsubstituted silyl group, a substituted keto group containing 1 to 20 C atoms, an alkoxycarbonyl group containing 2 to 20 C atoms, an aryloxycarbonyl group containing 7 to 20 C atom, a cyano group (—CN), a carbamoyl group (—C(=O)NH$_2$), a haloformyl group, a formyl group (—C(=O)—H), an isocyano group, isocyanate, thiocyanate, isothiocyanate, a hydroxyl group, a nitro group, CF$_3$, Cl, Br, F, a crosslinkable group, a substituted or unsubstituted aromatic ring system containing 5 to 40 ring atoms or substituted or unsubstituted heteroaromatic ring system containing 5 to 40 ring atoms, an aryloxy group containing 5 to 40 ring atoms or heteroaryloxy group containing 5 to 40 ring atoms, or a combination of these groups; and
at least one of $R_{11}$, $R_{12}$, $R_{13}$, $R_{14}$, $R_{15}$, $R_{16}$, $R_{17}$, $R_{18}$, $R_{19}$ and $R_{110}$ has a structure represented by general formula (II):

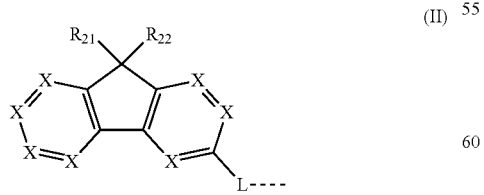

(II)

wherein
X is CR$_{23}$, and two or more Xs are the same or different;
each of $R_{21}$, $R_{22}$ and $R_{23}$ is independently selected from the group consisting of H, a linear alkyl containing 1 to 20 C atoms, linear alkoxy containing 1 to 20 C atoms or linear thioalkoxy group containing 1 to 20 C atoms, a branched or cyclic alkyl containing 3 to 20 C atoms, branched or cyclic alkoxy containing 3 to 20 C atoms or branched or cyclic thioalkoxy group containing 3 to 20 C atoms, a substituted or unsubstituted silyl group, a substituted keto group containing 1 to 20 C atoms, an alkoxycarbonyl group containing 2 to 20 C atoms, an aryloxycarbonyl group containing 7 to 20 C atom, a cyano group (—CN), a carbamoyl group (—C(=O)NH$_2$), a haloformyl group, a formyl group (—C(=O)—H), an isocyano group, isocyanate, thiocyanate, isothiocyanate, a hydroxyl group, a nitro group, CF$_3$, Cl, Br, F, a crosslinkable group, a substituted or unsubstituted aromatic ring system containing 5 to 40 ring atoms or substituted or unsubstituted heteroaromatic ring system containing 5 to 40 ring atoms, an aryloxy or heteroaryloxy group containing 5 to 40 ring atoms, or a combination of these groups;
L represents a single bond or a linking group, and the linking group is a substituted or unsubstituted aromatic ring system containing 5 to 40 ring atoms or substituted or unsubstituted heteroaromatic ring system containing 5 to 40 ring atoms, an aryloxy group containing 5 to 40 ring atoms or heteroaryloxy group containing 5 to 40 ring atoms, or a combination of these systems; and
L is linked to the fused ring of the general formula (I).

2. The fused ring compound according to claim 1, wherein $R_{11}$, $R_{13}$, $R_{14}$, $R_{16}$, $R_{18}$ and $R_{19}$ are all H, and at least one of $R_{12}$, $R_{15}$, $R_{17}$ and $R_{110}$ has one of the structures represented by general formulas (II-1)-(II-17):

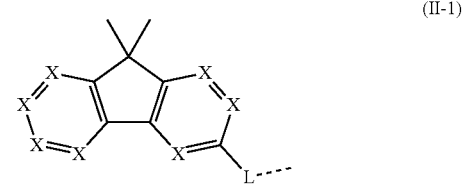

(II-1)

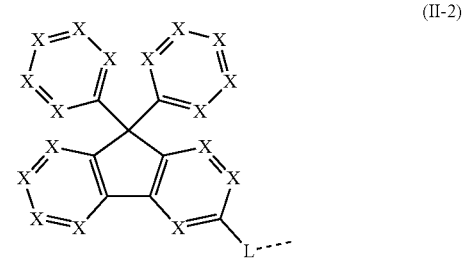

(II-2)

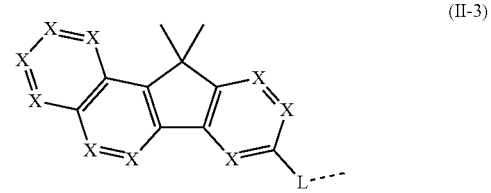

(II-3)

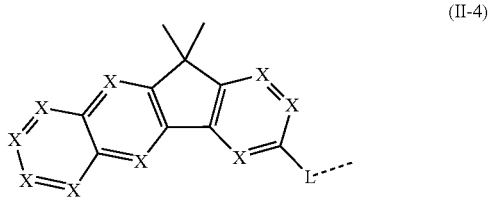

(II-4)

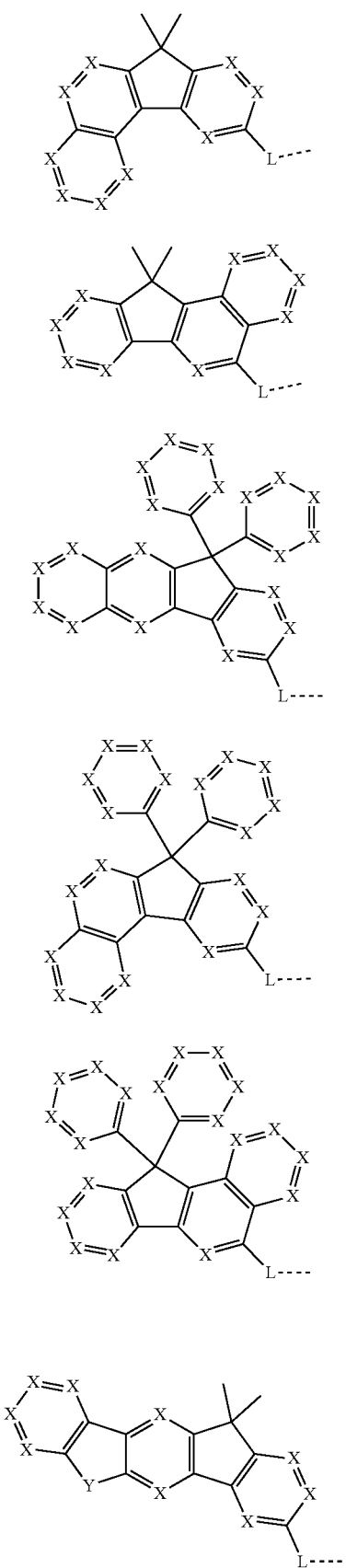
(II-5)
(II-6)
(II-7)
(II-8)
(II-9)
(II-10)
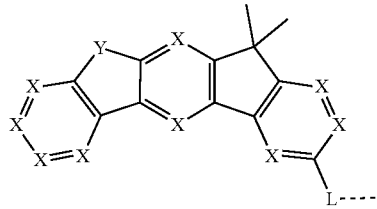
(II-11)
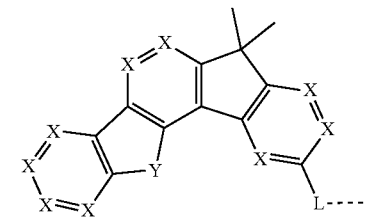
(II-12)
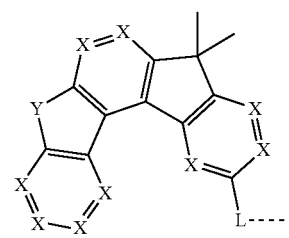
(II-13)
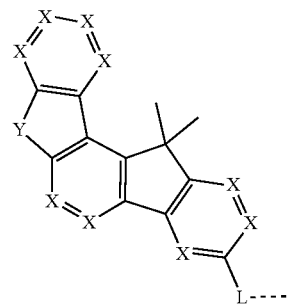
(II-14)
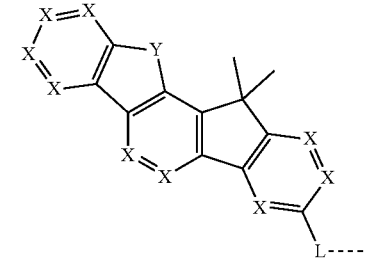
(II-15)
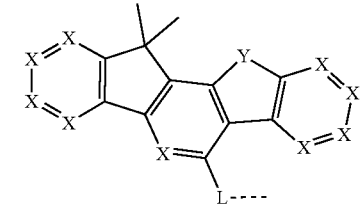
(II-16)

-continued (II-17)

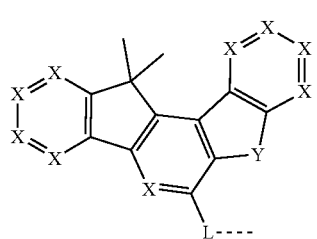

wherein
Y is selected from CR$_{25}$R$_{26}$, NR$_{27}$, O or S;
each of R$_{25}$, R$_{26}$ and R$_{27}$ is independently H, a linear alkyl containing 1 to 20 C atoms, alkoxy containing 1 to 20 C atoms or thioalkoxy group containing 1 to 20 C atoms, a branched or cyclic alkyl containing 3 to 20 C atoms, branched or cyclic alkoxy containing 3 to 20 C atoms or branched or cyclic thioalkoxy group containing 3 to 20 C atoms, a substituted or unsubstituted silyl group, a substituted keto group containing 1 to 20 C atoms, an alkoxycarbonyl group containing 2 to 20 C atoms, an aryloxycarbonyl group containing 7 to 20 C atom, a cyano group (—CN), a carbamoyl group (—C(=O)NH$_2$), a haloformyl group, a formyl group (—C(=O)—H), an isocyano group, isocyanate, thiocyanate, isothiocyanate, a hydroxyl group, a nitro group, CF$_3$, Cl, Br, F, a crosslinkable group, a substituted or unsubstituted aromatic ring system containing 5 to 40 ring atoms or substituted or unsubstituted heteroaromatic ring system containing 5 to 40 ring atoms, an aryloxy group containing 5 to 40 ring atoms or heteroaryloxy group containing 5 to 40 ring atoms, or a combination of these groups.

3. The fused ring compound according to claim 2, wherein at least one of R$_{12}$, R$_{15}$, R$_{17}$ and R$_{110}$ is one selected from structures represented by the general formulas (II-1)-(II-17), and the rest of R$_{12}$, R$_{15}$, R$_{17}$ and R$_{110}$ is selected from group consisting of H, D, methyl, ethyl, n-propyl, isopropyl, cyclopropyl, n-butyl, isobutyl, sec-butyl, tert-butyl, cyclobutyl, methylbutyl, n-pentyl, sec-pentyl, cyclopentyl, n-hexyl, cyclohexyl, n-heptyl, cycloheptyl, n-octyl, cyclooctyl, ethylhexyl, trifluoromethyl, pentafluoroethyl, trifluoroethyl, vinyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, octynyl, methoxy, trifluoromethoxy, ethoxy, n-propoxy, isopropoxy, n-butoxy, isobutoxy, sec-butoxy, tert-butoxy or methylbutoxy, trimethylsilane, and the following aromatic structures:

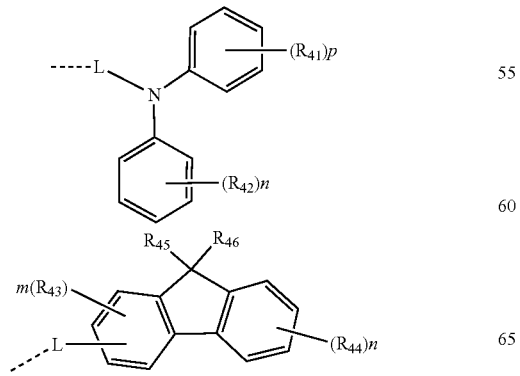

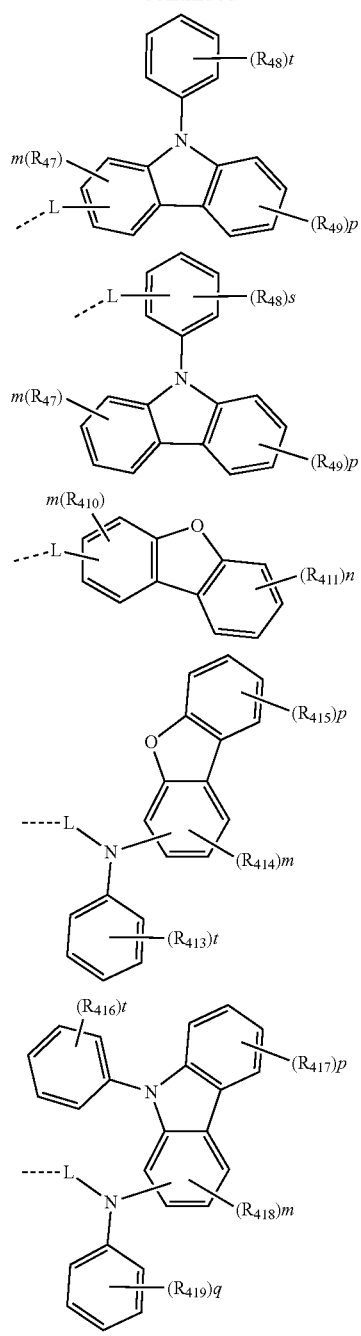

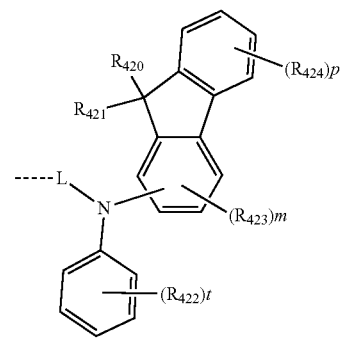

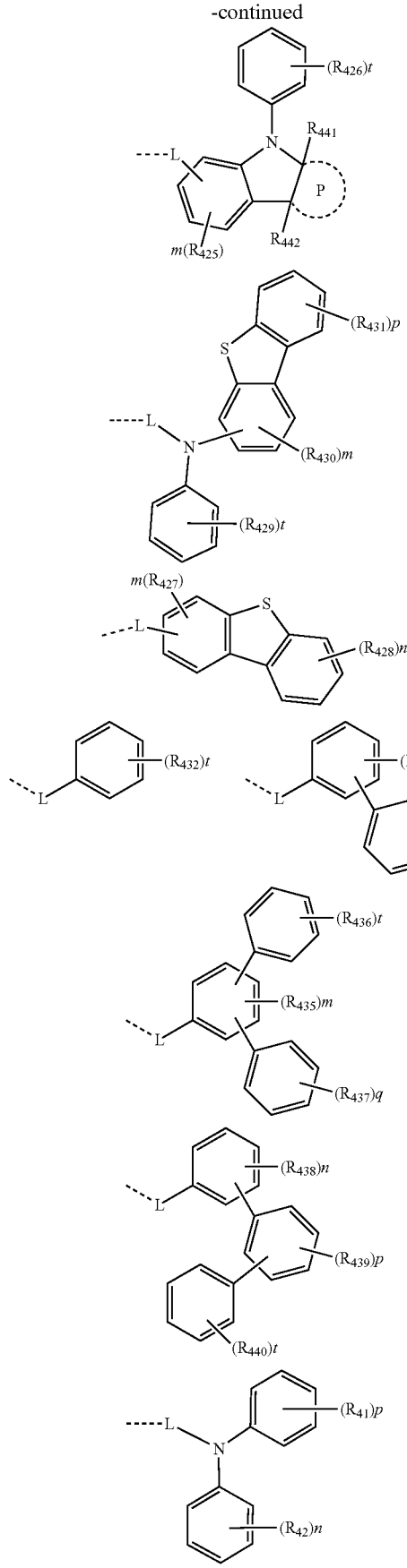
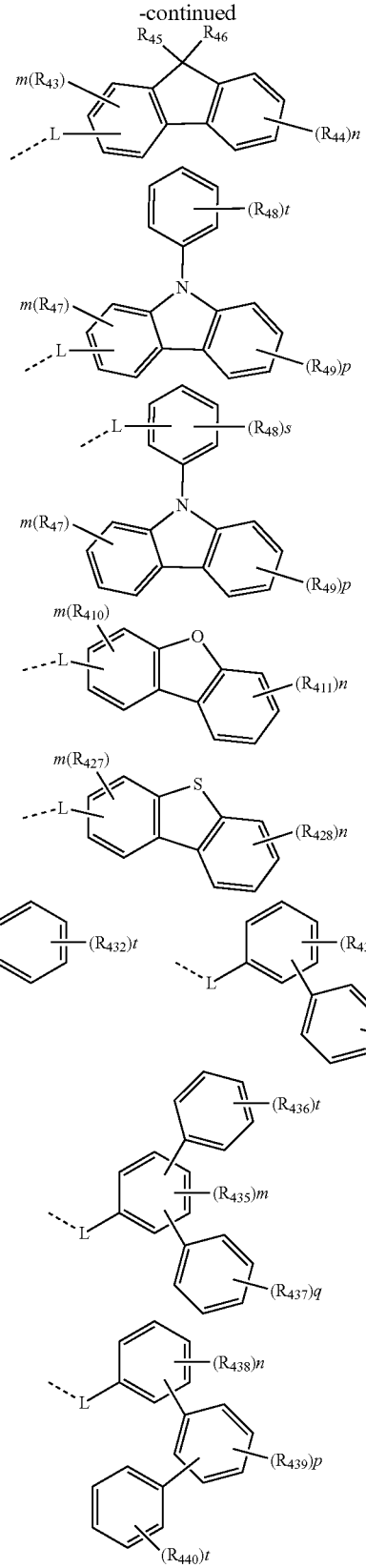
wherein
each of $R_{41}$-$R_{49}$ and $R_{410}$-$R_{440}$ is independently selected from the group consisting of H, a linear alkyl containing 1 to 20 C atoms, linear alkoxy containing 1 to 20 C atoms or linear thioalkoxy group containing 1 to 20 C atoms, a branched or cyclic alkyl containing 3 to 20 C atoms, branched or cyclic alkoxy containing 3 to 20 C atoms or branched or cyclic thioalkoxy group containing 3 to 20 C atoms, a substituted or unsubstituted silyl group, a substituted keto group containing 1 to 20 C atoms, an alkoxycarbonyl group containing 2 to 20 C atoms, an aryloxycarbonyl group containing 7 to 20 C atom, a cyano group (—CN), a carbamoyl group (—C(=O)NH$_2$), a haloformyl group, a formyl group (—C(=O)—H), an isocyano group, isocyanate, thiocyanate, isothiocyanate, a hydroxyl group, a nitro group, CF$_3$, Cl, Br, F, a crosslinkable group, a substituted or unsubstituted aromatic ring system containing 5 to 40 ring atoms or substituted or unsubstituted heteroaromatic ring system containing 5 to 40 ring atoms, an aryloxy group containing 5 to 40 ring atoms or heteroaryloxy group containing 5 to 40 ring atoms, or a combination of these groups;

m is an integer of 0 to 3, each of n, p and s is independently an integer of 0 to 4, and each of t and q is independently an integer of 0 to 5;

P is a saturated naphthene containing 3 to 8 C atoms;

L represents a single bond or a linking group, and the linking group can be a substituted or unsubstituted aromatic ring system containing 5 to 40 ring atoms or substituted or unsubstituted heteroaromatic ring system containing 5 to 40 ring atoms, an aryloxy group containing 5 to 40 ring atoms or heteroaryloxy group containing 5 to 40 ring atoms , or a combination of these systems;

L is linked to the fused ring of the general formula (I).

4. The fused ring compound according to claim 1, wherein L has a single bond or one or more combinations of the following structural formulas:

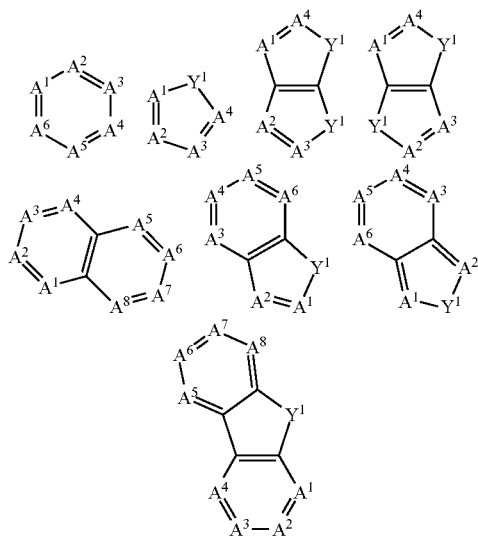

wherein
each of $A^1, A^2, A^3, A^4, A^5, A^6, A^7$ and $A^8$ is independently selected from CR$^3$ or N;
$Y^1$ is selected from CR$^4$R$^5$, SiR$^4$R$^5$, NR$^3$, C(=O), S or O;
$R^3$, $R^4$, and $R^5$ are selected from the group consisting of H, a linear alkyl containing 1 to 20 C atoms, linear alkoxy containing 1 to 20 C atoms or linear thioalkoxy group containing 1 to 20 C atoms, a branched or cyclic alkyl containing 3 to 20 C atoms, branched or cyclic alkoxy containing 3 to 20 C atoms or branched or cyclic thioalkoxy group containing 3 to 20 C atoms, an alkoxycarbonyl group containing 2 to 20 C atoms, an aryloxycarbonyl group containing 7 to 20 C atom, a cyano group (—CN), a carbamoyl group (—C(=O)NH$_2$), a haloformyl group, a formyl group (—C(=O)—H), an isocyano group, isocyanate, thiocyanate, isothiocyanate, a hydroxyl group, a nitro group, CF$_3$, Cl, Br, F, a crosslinkable group, a substituted or unsubstituted aromatic ring system containing 5 to 40 ring atoms or substituted or unsubstituted heteroaromatic ring system containing 5 to 40 ring atoms, an aryloxy group containing 5 to 40 ring atoms or heteroaryloxy group containing 5 to 40 ring atoms, or a combination of these groups, wherein one or more groups of R$^3$R$^4$and R$^5$ may form a monocyclic or polycyclic aliphatic or aromatic ring system with each other and/or with a ring bonded to said groups.

5. The fused ring compound according to claim 1, wherein at least part of H in the fused ring compound is substituted by deuterium.

6. A mixture, comprising the fused ring compound according to claim 1 and an organic solvent or a second organic functional material
wherein the second organic functional material is at least one selected from the group consisting of: a hole (also called electron hole) injection or transport material, a hole blocking material (HBM), an electron injection or transport material (EIM/ETM), an electron blocking material (EBM), a singlet emitter, a triplet emitter, a thermally activated delayed fluorescent material and an organic dye.

7. An organic electronic device comprising the fused ring compound according to claim 1.

8. The organic electronic device according to claim 7, wherein the organic electronic device is an organic light emitting diode, an organic photovoltaic cell, an organic light emitting cell, an organic field effect transistor, an organic light emitting field effect transistor, an organic laser, and an organic spintronic device, an organic sensor or an organic plasmon emitting diode.

9. The organic electronic device according to claim 7, wherein the organic electronic device is an organic electroluminescence device comprising a light emitting layer, and the light emitting layer comprises the fused ring compound.

10. The fused ring compound according to claim 2, wherein two of the four substitution positions of R12, R15, R17 and R110 are independently selected from structures represented by the general formulas (II-1)-(II-17).

11. The fused ring compound according to claim 10, wherein R15 and R110 are independently selected from structures represented by the general formulas (II-1)-(II-17).

12. The fused ring compound according to claim 1, wherein L is a single bond or selected from the following structural formulas:

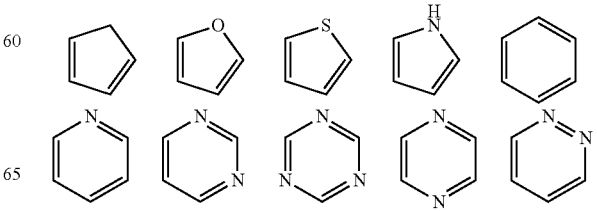

-continued

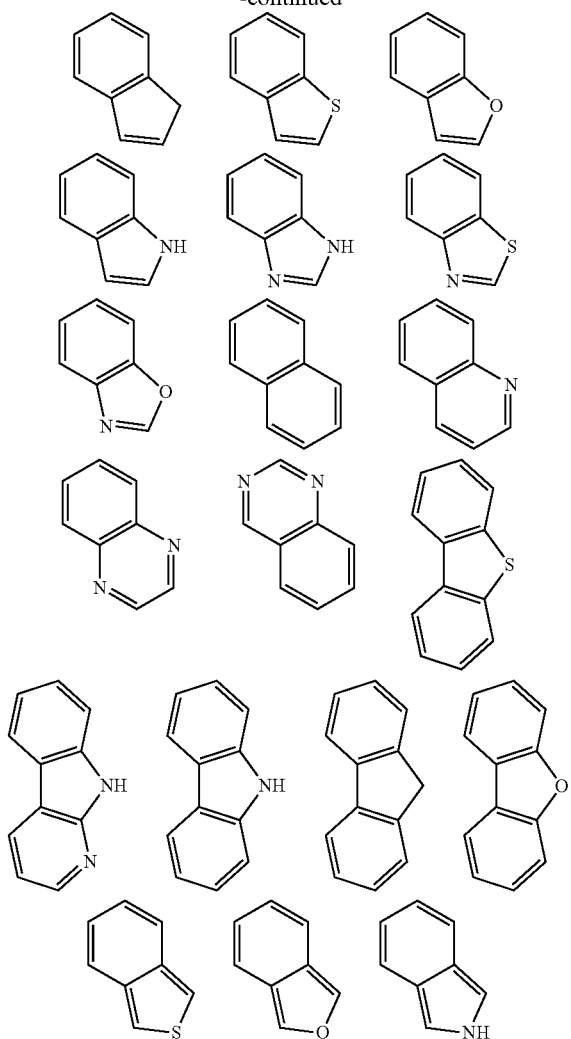

-continued

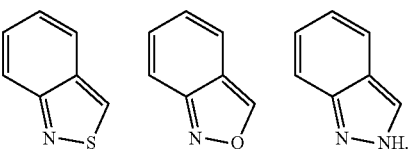

13. The fused ring compound according to claim 1, wherein L is a single bond.

14. The fused ring compound according to claim 1, wherein $R_{12}$ and $R_{17}$ are independently selected from the group consisting of a linear alkyl containing 1 to 20 C atoms, a branched or cyclic alkyl containing 3 to 20 C atoms, a substituted or unsubstituted aromatic ring system containing 5 to 40 ring atoms or substituted or unsubstituted heteroaromatic ring system containing 5 to 40 ring atoms, or a combination of these groups.

15. The fused ring compound according to claim 11, wherein $R_{12}$ and $R_{17}$ are independently selected from the group consisting of a linear alkyl containing 1 to 20 C atoms, a branched or cyclic alkyl containing 3 to 20 C atoms, a substituted or unsubstituted aromatic ring system containing 5 to 40 ring atoms or substituted or unsubstituted heteroaromatic ring system containing 5 to 40 ring atoms, or a combination of these groups.

16. A mixture according to claim 6, wherein the second organic functional material is a singlet emitter, a thermally activated delayed fluorescent material or a hole transport material.

17. A mixture according to claim 16, wherein the second organic functional material is a singlet emitter.

18. A mixture according to claim 17, wherein the fused ring compound is a guest material, and the fused ring compound of the mixture is present at a weight percentage≤15 wt %.

* * * * *